United States Patent
Roses et al.

(10) Patent No.: US 9,724,339 B2
(45) Date of Patent: *Aug. 8, 2017

(54) METHODS AND DRUG PRODUCTS FOR TREATING ALZHEIMER'S DISEASE

(71) Applicants: Takeda Pharmaceutical Company Limited, Osaka-shi, Osaka (JP); Zinfandel Pharmaceuticals, Inc., Durham, NC (US)

(72) Inventors: Allen D. Roses, Chapel Hill, NC (US); Rajneesh Taneja, Libertyville, IL (US)

(73) Assignees: Zinfandel Pharmaceuticals, Inc., Durham, NC (US); Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,511

(22) Filed: Jun. 15, 2015

(65) Prior Publication Data
US 2016/0000769 A1   Jan. 7, 2016

Related U.S. Application Data

(63) Continuation of application No. 13/346,081, filed on Jan. 9, 2012, now Pat. No. 9,102,666.

(60) Provisional application No. 61/431,370, filed on Jan. 10, 2011.

(51) Int. Cl.
*A61K 31/4439* (2006.01)
*C12Q 1/68* (2006.01)
*C07D 417/12* (2006.01)

(52) U.S. Cl.
CPC ........ *A61K 31/4439* (2013.01); *C07D 417/12* (2013.01); *C12Q 1/6883* (2013.01); *C12Q 2600/106* (2013.01); *C12Q 2600/118* (2013.01); *C12Q 2600/156* (2013.01); *C12Q 2600/158* (2013.01); *C12Q 2600/172* (2013.01); *Y10T 436/143333* (2015.01)

(58) Field of Classification Search
CPC .............. A61K 31/4439; C12Q 1/6883; C12Q 2600/158; C12Q 2600/172; C12Q 2600/118; C12Q 2600/156; C12Q 2600/106; C07D 417/12; Y10T 436/143333
See application file for complete search history.

(56) References Cited

U.S. PATENT DOCUMENTS

| | | | |
|---|---|---|---|
| 2,507,631 A | 5/1950 | Hartmann et al. |
| 4,687,777 A | 8/1987 | Meguro et al. |
| 5,002,953 A | 3/1991 | Hindley |
| 5,112,460 A | 5/1992 | Karger et al. |
| 5,171,750 A | 12/1992 | Brossi et al. |
| 5,326,770 A | 7/1994 | Wilkerson |
| 5,508,167 A | 4/1996 | Roses et al. |
| 5,595,883 A | 1/1997 | Appleyard et al. |
| 5,716,828 A | 2/1998 | Roses et al. |
| 5,716,975 A | 2/1998 | Bue-Valleskey et al. |
| 5,811,439 A | 9/1998 | Ogawa et al. |
| 5,904,824 A | 5/1999 | Oh |
| 5,965,569 A | 10/1999 | Camps Garcia et al. |
| 5,965,584 A | 10/1999 | Ikeda et al. |
| 5,990,126 A | 11/1999 | Park et al. |
| 6,027,896 A | 2/2000 | Roses et al. |
| 6,191,154 B1 | 2/2001 | Landreth et al. |
| 6,291,182 B1 | 9/2001 | Schork et al. |
| 6,303,633 B1 | 10/2001 | Chen et al. |
| 6,355,429 B1 | 3/2002 | Nygren et al. |
| 6,399,639 B1 | 6/2002 | Matsui et al. |
| 6,401,043 B1 | 6/2002 | Stanton, Jr. et al. |
| 6,432,985 B2 | 8/2002 | Alanine et al. |
| 6,532,467 B1 | 3/2003 | Brocklebank et al. |
| 6,559,188 B1 | 5/2003 | Gatlin et al. |
| 6,642,267 B2 | 11/2003 | Przewosny et al. |
| 6,673,780 B2 | 1/2004 | Dasseux et al. |
| 6,680,299 B2 | 1/2004 | Or et al. |
| 6,699,910 B2 | 3/2004 | Dasseux et al. |
| 6,703,422 B2 | 3/2004 | Dasseux et al. |
| 6,811,988 B2 | 11/2004 | Chojkier et al. |
| 6,828,462 B2 | 12/2004 | Henrich et al. |
| 6,838,452 B2 | 1/2005 | Harats et al. |
| 6,956,055 B2 | 10/2005 | Sundermann et al. |
| 6,964,868 B1 | 11/2005 | Williams et al. |
| 7,052,849 B2 | 5/2006 | Jackowski et al. |
| 7,122,373 B1 | 10/2006 | Williams et al. |
| 7,127,466 B2 | 10/2006 | Brocklebank et al. |
| 7,132,244 B2 | 11/2006 | Jackowski et al. |
| 7,135,297 B2 | 11/2006 | Jackowski et al. |
| 7,186,704 B2 | 3/2007 | Harats et al. |
| 7,304,093 B2 | 12/2007 | Dasseux et al. |
| 7,329,501 B2 | 2/2008 | Jackowski et al. |
| 7,504,388 B2 | 3/2009 | Harats et al. |
| 7,608,412 B2 | 10/2009 | Wooten et al. |

(Continued)

FOREIGN PATENT DOCUMENTS

| | | | |
|---|---|---|---|
| CN | 1257205 A | 6/2000 |
| CN | 1753675 A | 3/2006 |

(Continued)

OTHER PUBLICATIONS

Ahmad et al., "Myelin-associated Glycoprotein Protects Brain From NMDA-induced Acute Excitotoxicity: Critical Role of Myelination on Neuron Survival," Stroke, Apr. 2009, 40(4):e216-e217.

(Continued)

*Primary Examiner* — Sarah Pihonak
*Assistant Examiner* — Jason A Deck
(74) *Attorney, Agent, or Firm* — Foley & Lardner LLP

(57) ABSTRACT

Provided herein are drug products with low dose pioglitazone for use in the treatment (e.g., delay of onset) of cognitive impairment of the Alzheimer's type. Methods of manufacture thereof are also provided. Further provided are methods of treatment for Alzheimer's disease including administering a drug product with low dose pioglitazone. The methods may include determining whether the subject is at risk of developing Alzheimer's disease based upon the subject's age and TOMM40 523 genotype.

27 Claims, 9 Drawing Sheets

(56) References Cited

U.S. PATENT DOCUMENTS

| | | |
|---|---|---|
| 7,625,882 B2 | 12/2009 | Harats et al. |
| 7,833,513 B2 | 11/2010 | De la Monte et al. |
| 7,888,035 B2 | 2/2011 | Klass et al. |
| 7,893,291 B2 | 2/2011 | Harats et al. |
| 7,897,356 B2 | 3/2011 | Klass et al. |
| 7,902,176 B2 | 3/2011 | Harats et al. |
| 7,973,023 B2 | 7/2011 | Harats et al. |
| 8,005,623 B2 | 8/2011 | Hellerstein |
| 8,815,508 B2 | 8/2014 | Roses |
| 8,846,315 B2 | 9/2014 | Roses |
| 9,102,666 B2 | 8/2015 | Roses et al. |
| 2002/0077316 A1 | 6/2002 | Dasseux et al. |
| 2003/0022865 A1 | 1/2003 | Dasseux et al. |
| 2003/0078239 A1 | 4/2003 | Dasseux et al. |
| 2003/0096431 A1 | 5/2003 | Jackowski et al. |
| 2003/0100126 A1 | 5/2003 | Jackowski et al. |
| 2003/0220374 A1 | 11/2003 | Needleman |
| 2003/0225035 A1 | 12/2003 | Harats et al. |
| 2004/0060077 A1 | 3/2004 | Esmond et al. |
| 2004/0106677 A1 | 6/2004 | Harats et al. |
| 2004/0122091 A1 | 6/2004 | Dasseux et al. |
| 2004/0198814 A1 | 10/2004 | Dasseux et al. |
| 2004/0204502 A1 | 10/2004 | Dasseux et al. |
| 2004/0265849 A1 | 12/2004 | Cargill et al. |
| 2005/0004179 A1 | 1/2005 | Pedersen |
| 2005/0020694 A1 | 1/2005 | Dasseux et al. |
| 2005/0021236 A1 | 1/2005 | Aston et al. |
| 2005/0043242 A1 | 2/2005 | Esmond et al. |
| 2005/0272813 A1 | 12/2005 | Harats et al. |
| 2005/0277129 A1 | 12/2005 | Aerssens et al. |
| 2006/0020440 A1 | 1/2006 | Hellerstein |
| 2006/0194339 A1 | 8/2006 | Jackowski et al. |
| 2006/0205091 A1 | 9/2006 | Jackowski et al. |
| 2006/0211138 A1 | 9/2006 | Jackowski et al. |
| 2006/0211139 A1 | 9/2006 | Jackowski et al. |
| 2006/0211140 A1 | 9/2006 | Jackowski et al. |
| 2006/0211141 A1 | 9/2006 | Jackowski et al. |
| 2006/0211145 A1 | 9/2006 | Jackowski et al. |
| 2006/0211146 A1 | 9/2006 | Jackowski et al. |
| 2006/0228728 A1 | 10/2006 | Cox et al. |
| 2007/0010029 A1 | 1/2007 | Jackowski et al. |
| 2007/0099868 A1 | 5/2007 | Harats et al. |
| 2007/0105856 A1 | 5/2007 | Carpino et al. |
| 2007/0105859 A1 | 5/2007 | Isshiki et al. |
| 2007/0149615 A9 | 6/2007 | Dasseux et al. |
| 2007/0203083 A1 | 8/2007 | Mootha et al. |
| 2007/0238643 A1 | 10/2007 | Wooten et al. |
| 2008/0045582 A1 | 2/2008 | Zineh et al. |
| 2008/0051318 A1 | 2/2008 | Li et al. |
| 2008/0153088 A1 | 6/2008 | Sun et al. |
| 2008/0226719 A1 | 9/2008 | Roses et al. |
| 2008/0261865 A1 | 10/2008 | Harats et al. |
| 2008/0262047 A1 | 10/2008 | Roses et al. |
| 2008/0286876 A1 | 11/2008 | Stephanie |
| 2009/0042849 A1 | 2/2009 | Birnbaum |
| 2009/0143442 A1 | 6/2009 | Colca et al. |
| 2009/0209775 A1 | 8/2009 | Harats et al. |
| 2010/0048515 A1 | 2/2010 | Harats et al. |
| 2010/0092470 A1 | 4/2010 | Bhatt et al. |
| 2010/0105034 A1 | 4/2010 | Hutton et al. |
| 2010/0113290 A1 | 5/2010 | Klass et al. |
| 2010/0120842 A1 | 5/2010 | Barlow et al. |
| 2010/0136584 A1 | 6/2010 | Bhatt et al. |
| 2010/0184046 A1 | 7/2010 | Klass et al. |
| 2010/0203529 A1 | 8/2010 | Kuslich et al. |
| 2010/0256235 A1 | 10/2010 | Puder et al. |
| 2011/0082187 A1 | 4/2011 | Campbell et al. |
| 2011/0097350 A1 | 4/2011 | Harats et al. |
| 2011/0151460 A1 | 6/2011 | Klass et al. |
| 2011/0159506 A1 | 6/2011 | Klass et al. |
| 2011/0166185 A1 | 7/2011 | Roses |
| 2011/0189165 A1 | 8/2011 | Roses |
| 2011/0189212 A1 | 8/2011 | Harats et al. |
| 2011/0195394 A1 | 8/2011 | Selinfreund et al. |
| 2011/0195395 A1 | 8/2011 | Selinfreund et al. |
| 2011/0195396 A1 | 8/2011 | Selinfreund et al. |
| 2011/0195397 A1 | 8/2011 | Selinfreund et al. |
| 2011/0195398 A1 | 8/2011 | Selinfreund et al. |
| 2011/0195399 A1 | 8/2011 | Selinfreund et al. |
| 2011/0195400 A1 | 8/2011 | Selinfreund et al. |
| 2011/0195401 A1 | 8/2011 | Selinfreund et al. |
| 2011/0195402 A1 | 8/2011 | Selinfreund et al. |
| 2011/0195403 A1 | 8/2011 | Selinfreund et al. |
| 2011/0195404 A1 | 8/2011 | Selinfreund et al. |
| 2011/0195421 A1 | 8/2011 | Selinfreund et al. |
| 2011/0195422 A1 | 8/2011 | Selinfreund et al. |
| 2011/0195423 A1 | 8/2011 | Selinfreund et al. |
| 2011/0195424 A1 | 8/2011 | Selinfreund et al. |
| 2011/0195425 A1 | 8/2011 | Selinfreund et al. |
| 2011/0195427 A1 | 8/2011 | Selinfreund et al. |
| 2011/0195439 A1 | 8/2011 | Selinfreund et al. |
| 2011/0195440 A1 | 8/2011 | Selinfreund et al. |
| 2011/0195487 A1 | 8/2011 | Selinfreund et al. |
| 2011/0195488 A1 | 8/2011 | Selinfreund et al. |
| 2011/0195491 A1 | 8/2011 | Selinfreund et al. |
| 2011/0195508 A1 | 8/2011 | Selinfreund et al. |
| 2011/0195851 A1 | 8/2011 | Selinfreund et al. |
| 2011/0195855 A1 | 8/2011 | Selinfreund et al. |
| 2011/0195856 A1 | 8/2011 | Selinfreund et al. |
| 2011/0195857 A1 | 8/2011 | Selinfreund et al. |
| 2011/0195858 A1 | 8/2011 | Selinfreund et al. |
| 2011/0195859 A1 | 8/2011 | Selinfreund et al. |
| 2011/0195871 A1 | 8/2011 | Selinfreund et al. |
| 2011/0195872 A1 | 8/2011 | Selinfreund et al. |
| 2011/0195873 A1 | 8/2011 | Selinfreund et al. |
| 2011/0195874 A1 | 8/2011 | Selinfreund et al. |
| 2011/0196085 A1 | 8/2011 | Selinfreund et al. |
| 2011/0236317 A1 | 9/2011 | Cravo et al. |
| 2011/0237450 A1 | 9/2011 | Klass et al. |
| 2015/0073022 A1 | 3/2015 | Roses |
| 2015/0073025 A1 | 3/2015 | Roses |

FOREIGN PATENT DOCUMENTS

| | | |
|---|---|---|
| EP | 2172200 A1 | 4/2010 |
| JP | 2000-273040 A | 10/2000 |
| WO | WO 00/66102 A2 | 11/2000 |
| WO | WO 01/35941 A2 | 5/2001 |
| WO | WO 02/30860 A2 | 4/2002 |
| WO | WO 02/30882 A2 | 4/2002 |
| WO | WO 02/30884 A2 | 4/2002 |
| WO | WO 02/41827 A2 | 5/2002 |
| WO | WO 03/046001 A2 | 6/2003 |
| WO | WO 03/046005 A2 | 6/2003 |
| WO | WO 03/046573 A2 | 6/2003 |
| WO | WO 2004/005510 A1 | 1/2004 |
| WO | WO 2004/058258 A1 | 7/2004 |
| WO | WO 2004/106486 A2 | 12/2004 |
| WO | WO 2005/003766 A2 | 1/2005 |
| WO | WO 2005/047236 A1 | 5/2005 |
| WO | WO 2005/081943 A2 | 9/2005 |
| WO | WO 2006/054297 A2 | 5/2006 |
| WO | WO 2007/038112 A2 | 4/2007 |
| WO | WO 2007/038115 A2 | 4/2007 |
| WO | WO 2007/044522 A1 | 4/2007 |
| WO | WO 2007/109024 A2 | 9/2007 |
| WO | WO 2008/019187 A2 | 2/2008 |
| WO | WO 2008/036678 A2 | 3/2008 |
| WO | WO 2008/098318 A1 | 8/2008 |
| WO | WO 2008/147562 A2 | 12/2008 |
| WO | WO 2010/019550 A2 | 2/2010 |
| WO | WO 2010/033913 A1 | 3/2010 |
| WO | WO 2010/053788 A1 | 5/2010 |
| WO | WO 2010/056337 A2 | 5/2010 |
| WO | WO 2010/062706 A2 | 6/2010 |
| WO | WO 2010/066901 A2 | 6/2010 |
| WO | WO 2010/100653 A2 | 9/2010 |
| WO | WO 2010/123720 A1 | 10/2010 |

(56) References Cited

FOREIGN PATENT DOCUMENTS

| WO | WO 2011/109440 A1 | 9/2011 |
|---|---|---|
| WO | WO 2011/127219 A1 | 10/2011 |

OTHER PUBLICATIONS

Majima et al., "Safety and Efficacy of Low-dose Pioglitazone (7.5 mg/day) vs. Standard-dose Pioglitazone (15 mg/day) in Japanese Women with Type 2 Diabetes Mellitus," Endocrine Journal, 2006, 53(3):325-330.
Allen et al., "Reduced Hippocampal Functional Connectivity in Alzheimer Disease," Archives of Neurology, Oct. 2007, 64(10):1482-1487.
Bunsey et al., "Conservation of hippocampal memory function in rats and humans," Nature, Jan. 18, 1996, 379:255-257.
Roses et al., "New applications of disease genetics and pharmacogenetics to drug development," Current Opinion in Pharmacology, 2014, 14:81-89.
Zhou et al., "Aberrant Functional Connectivity Architecture in Alzheimer's Disease and Mild Cognitive Impairment: A Whole-Brian, Data-Driven Analysis," BioMed Research International, 2015, Article ID 495375, 9 pages.
Langer, Robert, "Drug delivery and targeting," Nature, Apr. 30, 1998, 392(Supp):5-10.
Watson et al., "Preserved Cognition in Patients with Early Alzheimer Disease and Amnestic Mild Cognitive Impairment During Treatment With Rosiglitazone," The American Journal of Geriatric Psychiatry, Nov. 2005, 13(11):950-958.
Deng et al., "Meta-analysis of the association of the LRP C766T polymorphism with the risk of Alzheimer's disease," Genetics, Dec. 31, 2006, 28(4):393-398, English abstract.
Hanyu et al., "The role of tumor necrosis factor-alpha in cognitive improvement after peroxisome proliferator-activator gamma agonist pioglitazone treatment in Alzheimer's disease," Journal of the American Geriatrics Society, May 2020, 58(5):1000-1001.
"AD, Risk, ApoE—Tomm40 No Tomfoolery," Alzheimer Research Forum, Nov. 15, 2009, http://www.alzforum.org/new/detailprint. asp?id=2285, 3 pages.
Abbatecola et al., "Rosiglitazone and Cognitive Stability in Older Individuals With Type 2 Diabetes and Mild Cognitive Impairment," Diabetes Care Aug. 2010, 33(8):1706-1711.
Abeid et al., "Apolipoprotein-E genotype and the risk of developing cholelithiasis following bariatric surgery: a clue to prevention of routine prophylactic cholecystectomy," Obesity Surgery, 2002, 12:354-357.
Abraham et al., "A genome-wide association study for late-onset Alzheimer's disease using DNA pooling," BMC Med Genomics, 2008, 1: 44.
Akuffo et al., "The discovery and early validation of novel plasma biomarkers in mild-to-moderate Alzheimer's disease pateitns responding to treatment with rosiglitazone," Biomarkers, 2008, 13(6), 618-636.
Albert et al., "The diagnosis of mild cognitive impairment due to Alzheimer's disease: Recommendations from the National Institute on Aging-Alzheimer's Association workgroups on diagnostic guidelines for Alzheimer's disease," Alzheimer's & Dementia, 2011, 7:270-279.
Andreotti et al., "Polymorphisms of genes in the lipid metabolism pathway and risk of biliary tract cancers and stones: a population-based case-control study in Shanghai, China," Cancer Epidemiol Biomarkers Prev, 2008, 17(3):525-534.
Bang et al., "Important link between dementia subtype and apolipoprotein E: a meta-analysis," Yonsei Med J, 2003, 44(3):401-413.
Bardel et al., "On the use of haplotype phylogeny to detect disease susceptibility loci," BMC Genetics, May 18, 2005, 6: 24-37.
Barnes et al. "Risk in drug trials," The Lancet, Dec. 2006, 368:2205-2206.

Baum et al., "Apolipoprotein E∈4 allele is associated with vascular dementia," Dement. Geriatr. Cogn. Disord., Aug. 22, 2006, 22: 301-305.
Beecham et al., "PCDH11X variation is not associated with late-onset Alzheimer disease susceptibility," Psychiatr. Genet., 2010, 20(6):321-324.
Bekris et al., "APOE mRNA and protein expression in postmortem brain are modulated by an extended haplotype structure," Am. J. Med. Genet. Part B, 2010, 153B: 409-417.
Bekris et al., "Multiple SNPs within and surrounding the apolipoprotein E gene influence cerebrospinal fluid apolipoprotein E protein levels," J. Alzheimers Dis., 2008, 13:255-266.
Bennet et al., "Association of apolipoprotein E genotypes with lipid levels and coronary risk," JAMA, Sep. 19, 2007, 298(11):1300-1311.
Bertram et al., "Systematic meta-analyses of Alzheimer disease genetic association studies: the AlzGene database," Nat. Genet., Jan. 2007, 39(1):17-23.
Blacker et al., "ApoE-4 and Age at Onset of Alzheimer's Disease: The NIMH Genetics Initiative," Neurology, 1997, 48:139-147.
Blagosklonny, Mikhail V., "Validation of anti-aging drugs by treating age-related diseases," Aging, Mar. 2009, 1(3):281-288. Electronic Publication: Mar. 28, 2009. Ref: 107 Journal code: 101508617.
Blalock et al., "Effects of Long-Term Pioglitaozne Treatment on Peripheral and Central Markers of Aging," PLoS One, Apr. 2010, 5(4):1-14.
Bojanowski et al., "An Apolipoprotein E variant may protect against age-related macular degeneration through cytokine regulation," Environ. Mol. Mutagen., 2006, 47:594-602.
Boland et al., "Apolipoprotein E Genotype and Gallbladder Disease Risk in a Large Population-Based Cohort," Annals of Epidemiology, Oct. 2006, 16(10):763-769.
Bright et al., "PPAR Regulation of Inflammatory Signaling in CNS Diseases," PPAR Research, 2008, 658520, 12 pages.
Brodbeck et al., "Rosiglitazone increases dendritic spine density and rescues spine loss caused by apolipoprotein E4 in primary cortical neurons," Proc. Natl. Acad. Sci. USA, 2008, 105(4):1343-1346.
Brookmeyer et al., "Forecasting the global burden of Alzheimer's disease," Alzheimer's & Dementia, The Journal of the Alzheimer's Association, 2007, 3(3):186-191.
Brookmeyer et al., "Projections of Alzheimer's Disease in the United States and the Public Health Impact of Delaying Disease Onset," American Journal of Public Health, Sep. 1998, 88(9):1337-1342.
Brune et al., "Polymorphism in the peroxisome proliferator-activated receptor α gene influences the risk for Alzheimer's disease," Journal of Neural Transmission, Sep. 2003, 110(9):1041-1050.
Bruno et al., "Cerebrospinal fluid cortisol concentrations in healthy elderly are affected by both APOE and TOMM40 variants," Psychoneuroendocrinology In Press, Epub ahead of print: Jul. 30, 2011, 6 pages.
Burt et al., "Apolipoprotein (apo) E4 enhances HIV-1 cell entry in vitro, and the APOE epsilon4/epsilon4 genotype accelerates HIV disease progression," Proc. Natl. Acad. Sci. USA, Jun. 24, 2008, 105(25):8718-8723.
Cacabelos R., Chapter 10, Pharmacogenomics in Alzheimer's disease, Methods in Molecular Biology, 2008, 448:213-357.
Cacabelos, R., "Molecular Pathology and Pharmacogenomics in Alzheimer's Disease: Polygenic-related Effects of Multifactorial Treatments on Cognition, Anxiety, and Depression," Methods Find. Exp. Clin. Pharmacol., 2007, 29(SupplA):1-91.
Camacho et al., "Peroxisome Proliferator-Activated Receptor γ Induces a Clearance Mechanism for the Amyloid-$β^2$ Peptide," The Journal of Neuroscience, Dec. 1, 2004, 24(48):10908-10917.
Carrasquillo et al., "Genetic variation in PCDH11X is associated with susceptibility to late-onset Alzheimer's disease," Nat. Genet., Feb. 2009, 41(2):192-198.
Caselli et al., "Longitudinal modeling of age-related memory decline and the APOE ∈4 effect," N. Engl. J. Med., Jul. 16, 2009, 361(3):255-263.

(56) References Cited

OTHER PUBLICATIONS

Caselli et al., "TOMM40, APOE and preclinical memory decline," Presented at International Conference on Alzheimer's Disease, Paris, France. Jul. 18, 2011, Alzheimer's and Dementia, 7: S293, O2-03-01.

Caselli et al., "TOMM40, APOE, and age of onset of Alzheimer's disease," Presented at International Conference on Alzheimer's Disease, Honolulu, Hawaii on Jul. 10-15. Published in Alzheimer's and Dementia 6: S202, P1-096, 2010.

Chang et al., "Lipid- and receptor-binding regions of apoliprotein E4 fragments act in concert to cause mitochondrial dysfunction and neurotoxicity," Proc. Natl. Acad. Sci. USA, Dec. 20, 2005, 102(51):18694-18699.

Chu et al., "TOMM40 poly-T repeat lengths, age of onset and psychosis risk in Alzheimer disease," Neurobiology of Aging, 2011, 32:2328.e1-2328.e9, In Press, Epub ahead of print: Aug. 4, 2011.

CINAPS Compound Dossier, Pioglitazone, Dec. 22, 2009, 21 pages.

Clement et al., "TCS: a computer program to estimate gene genealogies," Mol. Ecol., 2000, 9:1657-1659.

Cogswell et al., "Identification of miRNA Changes in Alzheimer's Disease Brain and CSF Yields Putative Biomarkers and Insights into Disease Pathways," Journal of Alzheimer's Disease, May 2008, 14(1):27-41.

Collino et al., "Modulation of the oxidative stress and inflammatory response by PPAR-γ agonists in the hippocampus of rats exposed to cerebral ischemia/reperfusion," European Journal of Pharmacology, 2006, 530:70-80.

Combs et al., "Inflammatory mechanisms in Alzheimer's disease: inhibition of γ-amyloid-stimulated proinflammatory responses and neurotoxicity by PPARγ agonists," Journal of Neuroscience, 2000, 20(2): 558-567.

Comment by Allen Roses http://www.alzforum.org/new/detail.asp?id=2873, Primary Papers: Association and Expression Analyses With Single-Nucleotide Polymorphisms in TOMM40 in Alzheimer Disease., Submitted Aug. 15, 2011, Posted Aug. 15, 2011.

Coon et al., "A high-density whole-genome association study reveals that APOE is the major susceptibility gene for sporadic late-onset Alzheimer's disease," J. Clin. Psychiatry, Apr. 2007, 68(4):613-618.

Corder et al., "Gene dose of apolipoprotein E type 4 allele and the risk of Alzheimer's disease in late onset families," Science, Aug. 13, 1993, 261:921-923.

Corder et al., "Protective effect of apolipoprotein E type 2 allele for late onset Alzheimer disease," Nat. Genet., Jun. 1994, 7:180-184.

Costa et al., "Multiplex allele-specific fluorescent PCR for haplotyping the IVS8 $(TG)_m(T)_n$ locus in the CFTR gene," Clin. Chem., 2008, 54(9):1564-1567.

Costello et al., "Agonists of peroxisome proliferator-activated receptor-[γ] attenuate the A[β]-mediated impairment of LTP in the hippocampus in vitro," Neuropharmacology, 2005, 49:359-366.

Cruchaga et al. for the Alzheimer's Disease Neuroimaging Initiative, "Association and Expression Analyses With Single-Nucleotide Polymorphisms in TOMM40 in Alzheimer Disease," Arch. Neurol., Aug. 2011, 68:1013-1019.

Das, Undurti N., "Acetylcholinesterase and butyrylcholinesterase as possible markers of low-grade systemic inflammation," Medical Science Monitor, 2007, 13(12):RA214-RA221.

de la Monte et al., "Alzheimer's Disease Is Type 3 Diabetes-Evidence Reviewed," Journal of Diabetes Science and Technology, Nov. 2008, 2(6):1101-1113.

de la Monte et al., "Nitrosamine exposure exacerbates high fat diet-mediated type2 diabetes mellitus, non-alcoholic steatohepatitis, and neurodegeneration with cognitive impairment," Molecular Nuerodegeneration, 2009, 4:54 (pp. 1-21).

Dean et al., "Plasma apolipoprotein E is decreased in schizophrenia spectrum and bipolar disorder," Psychiatry Research, 2008, 158:75-78.

Devi et al., "Accumulation of amyloid precursor protein in the mitochondrial import channels of human Alzheimer's disease brain is associated with mitochondrial dysfunction," J. Neurosci., Aug. 30, 2006, 26(35):9057-9068.

Devi et al., "Mitochondrial trafficking of APP and alpha synuclein: Relevance to mitochondrial dysfunction in Alzheimer's and Parkinson's diseases," Biochimica et Biophysica Acta (BBA)—Molecular Basis of Disease, 2010, 1802:11-19.

Doraiswamy et al., "Pharmacological strategies for the prevention of Alzheimer's disease," Expert Opinion on Pharmacotherapy, Jan. 2006, 7(1):1-10.

Dubois et al., "Research criteria for the diagnosis of Alzheimer's disease: revising the NINCDS-ADRDA criteria," Lancet Neurol., Aug. 2007, 6:734-746.

Dubois et al., "Revising the definition of Alzheimer's disease: a new lexicon," Lancet Neurol., Nov. 2010, 9:1118-1127.

Efron et al., "Bootstrap confidence levels for phylogenetic trees," Proc. Natl. Acad. Sci. USA, 1996, 93:13429-13434.

Elliott et al., "Genetic Loci associated with C-reactive protein levels and risk of coronary heart disease," JAMA, Jul. 1, 2009, 302(1):37-48.

Elosua et al., "Obesity Modulates the Association among APOE Genotype, Insulin, and Glucose in Men," Obesity, Dec. 2003, 11(12):1502-1508.

Escribano et al., "Rosiglitazone rescues memory impairment in Alzheimer's transgenic mice: mechanisms involving a reduced amyloid and tau pathology," Neuropsychopharmacology, 2010, 35:1593-1604.

Escribano et al., "Rosiglitazone reverses memory decline and hippocampal glucocorticoid receptor down-regulation in an Alzheimer's disease mouse model," Biochemical & Biophysical Research Communications, 2009, 379:406-410.

Farrer et al., "Effects of Age, Sex, and Ethnicity on the Association Between Apolipoprotein E Genotpye and Alzheimer Disease," JAMA, Oct. 22/29, 1997, 278(16):1349-1356.

Fu, P.C., "The Effect and Mechanism Research of Pioglitazone to the Memory Impairment of Ad Rats," Globe Thesis [online] Sep. 22, 2010 (retrieved on Sep. 4, 2012), 2 page abstract.

Gao et al., "An experimental study of pioglitazone in treating vascular dementia," Academic Journal of Xi'an Jiaotong University, Aug. 2010. 22(3):179-182.

Gemma et al., "Rosiglitazone improves contextual fear conditioning in aged rats," Neuroreport, Oct. 5, 2004, 15(14):2255-2259.

Green et al., "Presymptomatic Genetic Testing for Neurodegenerative Diseases," Virtual Mentor, Aug. 2004, 6(8):1-4.

Groman et al., "Variation in a repeat sequence determines whether a common variant of the cystic fibrosis transmembrane conductance regulator gene is pathogenic or benign," Am. J. Hum. Genet., 2004, 74(1):176-179.

Grossman et al., "Alzheimer's disease: diagnostics, prognostics and the road to prevention," The EPMA Journal, 2010, 1:293-303.

Grupe et al., "Evidence for novel susceptibility genes for late-onset Alzheimer's disease from a genome-wide association study of putative functional variants," Hum. Mol. Genet., 2007, 16(8):865-873.

Gupta et al., "Polymorphism in apolipoprotein E among migraineurs and tension-type headache subjects," J. Headache Pain, 2009, 10:115-120.

Hahn et al., "Population genetic and phylogenetic evidence for positive selection on regulatory mutations at the factor VII locus in humans," Genetics, Jun. 2004, 167:867-877.

Haines et al., "Whole-genome SNP linkage screen for dementia in the midwestern U.S. Amish," Alzheimer's and Dementia, 2008, 4: T586-T587, P3-225.

Hanyu et al., "Alzheimer's Disease," Nihon Rinsho, Feb. 2010, 68(2):330-334 (article in Japanese).

Hanyu et al., "Pioglitazone Improved Cognition in a Pilot Study on Patients with Alzheimer's Disease and Mild Cognitive Impairment with Diabetes Mellitus," J. Am. Geriart. Soc., Jan. 2009, 57(1):177-179.

Harikumar et al., "Resveratrol, A multitargeted agent for age-associated chronic diseases," Cell Cycle, Apr. 15, 2008, 7(8):1020-1035.

(56) References Cited

OTHER PUBLICATIONS

Harold et al., "Genome-wide association study identifies variants at CLU and PICALM associated with Alzheimer's disease," Nature Genetics, Oct. 2009, 41:1088-1093.

Harvie et al., "The effects of intermittent or continuous energy restriction on weight loss and metabolic disease risk markers: a randomized trial in young overweight women," International Journal of Obesity, May 2011, 35(5):714-727.

Hayden et al., "TOMM40 "523" Genotype Affects Age of Alzheimer's Disease Onset Differentially by Race," Presented at International Conference on Alzheimer's Disease, Paris, France. Alzheimer's and Dementia, 2011, 7:S186, P1-235.

Hegele, Robert A., "SNP Judgments and Freedom of Association," Arterioscler. Thromb. Vasc. Biol., 2002, 22;1058-1061.

Heneka et al., "Acute treatment with the PPARγ agonist pioglitazone and ibuprofen reduces glial inflammation and Aβ1-42 levels in APPV717I transgenic mice," Brain, 2005, 128:1442-1453.

Heneka, et al., "Peroxisome proliferator-activated receptor-γ ligands reduce neuronal inducible nitric oxide synthase expression and cell death in vivo," [Erratum appears in J Neurosci Nov. 15, 2000;20(22):1a] Journal of Neuroscience, Sep. 15, 2000, 20(18):6862-6867.

Hermann et al., "Current and Emerging Drug Treatment Options for Alzheimer's Disease," Drugs, 2011, 71(15):2031-2065.

Huang et al., "APOE-ε2 allele associated with higher prevalence of sporadic Parkinson disease," Neurology, 2004, 62:2198-2202.

Huang et al., "Apolipoprotein E and dementia in Parkinson disease: a meta-analysis," Arch. Neurol., Feb. 2006, 63:189-193.

Hubacek et al., "Apolipoprotein E Polymorphism in Hemodialyzed Patients and Healthy Controls," Biochemical Genetics, 2009, 47:688-693.

Humphries et al., "Dissection of the Mitochondrial Import and Assembly Pathway for Human Tom40," J. Biol Chem., Mar. 25, 2005, 280(12):11535-11543.

Hurley et al., "Strength Training as a Countermeasure to Aging Muscle and Chronic Disease," Sports Medicine, Apr. 1, 2011, 41(4):289-306.

Inestrosa et al., "Peroxisome proliferator-activated receptor γ is expressed in hippocampal neurons and its activation prevents β-amyloid neurodegeneration: role of Wnt signaling," Experimental Cell Research, 2005, 304:91-104.

James et al., "Pharmacogenomic effects of apolipoprotein E on intracerebral hemorrhage," Stroke, 2009, 40:632-639.

Johnson et al., "A comparative study of five technologically diverse CFTR testing platforms," J. Mol. Diagn., Jul. 2007, 9(3): 401-407.

Johnson et al., "The Effect of TOMM40 Poly-T length on Gray Matter Volume and Cognition in Middle-Aged Persons with APOE ε3/ε3 Genotype," Alzheimer's and Dementia, 2011, 7:456-465.

Johnson et al., "Tomm40 Is Associated With Gray Matter Volume In Middle-aged Persons With Apoe ε3/ε3 Genotype," Presented at International Conference of Alzheimer's disease, Honolulu, Hawaii. Alzheimer's and Dementia, 6: e16, O4-03-04.

Juppner, H., "Functional Properties of the PTH/PTHrP Receptor," Bone, Aug. 1995, 17(2)Supplement:39S-42S.

Kampman et al., "Apolipoprotein E polymorphism is associated with age of onset in schizophrenia," J. Hum. Genet., 2004, 49:355-359.

Kaur et al., "Exploring mechanism of pioglitazone-induced memory restorative effect in experimental dementia," Fundamental & Clinical Pharmacology, 2009 23:557-566.

Kenter et al., "Establishing risk of human experimentation with drugs: lessons from TGN1412," The Lancet, Oct. 14, 2006, 368:1387-1391.

Khachaturian et al., "Developing a national strategy to prevent dementia: Leon Thal Symposium 2009," Alzheimer's and Dementia, 2010, 6:89-97.

Khachaturian et al., "Creating a transatlantic research enterprise for preventing Alzheimer's disease," Alzheimer's & Dimentia, The Journal of the Alzheimer's Association, 2009, 5(4):361-366.

Kobler et al., "Identification of an 11T allele in the polypyrimidine tract of intron 8 of the CFTR gene," Genet. Med., Feb. 2006, 8(2):125-128.

Koutsis et al., "APOE genotypes in Greek multiple-sclerosis patients: no effect on the MS Severity Score," J. Neurol., 2007, 254:394-395.

Kumar et al., "Beneficial effects of pioglitazone on cognitive impairment in MPTP model of Parkinson's disease," Behavioural Brain Research, 2009, 197:398-403.

Label Actos-Pioglitazone FDA 1999. 42 pages.

Lai et al., "A 4-Mb high-density single nucleotide polymorphism-based map around human APOE," Genomics, 1998, 54:31-38.

Lambert et al., "Genome-wide association study identifies variants at CLU and CR1 associated with Alzheimer's disease," Nat. Genet., Oct. 2009, 41(10):1094-1099.

Landreth et al., "PPARγ Agonists as Therapeutics for the Treatment of Alzheimer's Disease," Neurotherapeutics, Jul. 2008, 5(3):481-489.

Landreth G, "PPARγ agonists as new therapeutic agents for the treatment of Alzheimer's disease," Experimental Neurology, 2006, 199:245-248.

Landreth, G., "Therapeutic use of agonists of the nuclear receptor PPARgamma in Alzheimer's disease," Curr. Alzheimer Res., Apr. 2007, 4(2):159-164, abstract.

Larkin et al., "Clustal W and Clustal X version 2.0," Bioinformatics, 2007, 23(21): 2947-2948.

Leiva et al., "Relationship between Apolipoprotein E polymorphism and nephropathy in type-2 diabetic patients," Diabetes Res. Clin. Pract., 2007, 78:196-201.

Lencel et al., "Inflammaging: The driving force in osteoporosis?" Medical Hypotheses, Mar. 2011, 76(3):317-321.

Lescai et al., "An APOE Haplotype Associated with Decreased ε4 Expression Increases the Risk of Late Onset Alzheimer's Disease," Journal of Alzheimer's Disease, 2011, 24:235-245.

Lewis et al., "Methodological problems in genetic association studies of longevity—The apolipoprotein E gene as an example," Int. J. Epidemiol., 2004, 33:962-970.

Li et al., "Candidate single-nucleotide polymorphisms from a genomewide association study of Alzheimer disease," Arch. Neurol., 2008, 65(1):45-53.

Li et al., "Infection induces a positive acute phase apolipoprotein E response from a negative acute phase gene: role of hepatic LDL receptors," J. Lipid Res., 2008, 49:1782-1793.

Librado et al., "DnaSP v5: a software for comprehensive analysis of DNA polymorphism data," Bioinformatics, 2009, 25(11):1451-1452.

Linnertz, Colton et al., "Characterization of the Poly-T Variant in the TOMM40 Gene in Diverse Pupulations," PLOS One, Feb. 16, 2012, 7(2):e30994, 6 pages.

Liu et al., "Effect of pioglitazone on insulin resistance in fructose-drinking rats correlates with AGEs/RAGE inhibition and block of NAPDH oxidase and NF kappa B activation," European Journal of Pharmacology, 2010, 629:153-158.

Lo et al., "Modulating effect of apolipoprotein E polymorphisms on secondary brain insult and outcome after childhood brain trauma," Childs Nerv. Syst., 2009, 25:47-54.

Lutz et al., "Frequencies of the Alzheimer's disease associated TOMM40 polyT allele in different ethnic groups," Presented at the American Society of Human Genetics 60th Annual Meeting, Washington, DC on Nov. 3, 2010, 1 page poster.

Lutz et al., "Genetic variation at a single locus and age of onset for Alzheimer's disease," Alzheimer's and Dementia, 2010, 6: 125-131.

Lutz et al., "The importance of being connected," J. Alzheimers Dis., 2011, 24:247-251.

Mahley et al. "Apolipoprotein E4: a causative factor and therapeutic target in neuropathology, including Alzheimer's disease," Proc. Natl. Acad. Sci. USA, 2006, 103(15):5644-5651.

Martin et al., "Analysis of Association at Single Nucleotide Polymorphisms in the APOE Region," Genomics, 2000, 63:7-12.

Martin et al., "SNPing Away at Complex Diseases: Analysis of Single-Nucleotide Polymorphisms around APOE in Alzheimer Disease," The American Journal of Human Genetics, 2000, 67:383-394.

(56) References Cited

OTHER PUBLICATIONS

Martinez et al., "Apolipoprotein E4 is probably responsible for the chromosome 19 linkage peak for Parkinson's disease," Am. J. Med. Genet. B Neuropsychiatr. Genet., 2005, 136B: 72-74.
Masterman et al., "The telltale scan: APOE ϵ4 in multiple sclerosis," Lancet Neurology, Jun. 2004, 3:331.
Miglio et al., "PPARγ stimulation promotes mitochondrial biogenesis and prevents glucose deprivation-induced neuronal cell loss," Neurochemistry International, 2009, 55:496-504.
Miglio et al., "PPARγ stimulation promotes neurite outgrowth in SH-SY5Y human neuroblastoma cells," Neuroscience Letters, 2009, 454:134-138.
Morales-Garcia et al., "Peroxisome proliferator-activated receptor γ ligands regulate neural stem cell proliferation and differentiation in vitro and in vivo," GLIA, 2011, 59:293-307.
Moreno et al., "The Apolipoprotein E Gene Promoter (-219G/T) Polymorphism Determines Insulin Sensitivity in Response to Dietary Fat in Healthy Young Adults," J. Nutr., 2005, 135:2535-2540.
Morine et al., "Bi-directional gene set enrichment and canonical correlation analysis identify key diet-sensitive pathways and biomarkers of metabolic syndrome," BMC Bioinformatics, 2010, 11:499 (pp. 1-13).
Myllykangas et al., "APOE ϵ3-haplotype modulates Alzheimer β-amyloid deposition in the brain," American Journal of Medical Genetics, 2002, 114:288-291.
Nicodemus et al., "Comprehensive association analysis of APOE regulatory region polymorphisms in Alzheimer disease," Neurogenetics, 2004, 5:201-208.
Nicolakakis et al., "Complete rescue of cerebrovascular function in aged Alzheimer's disease transgenic mice by antioxidants and pioglitazone, a peroxisome proliferator-activated receptor γ agonist," Journal of Neuroscience, 2008, 28:9287-9296.
Nicolakakis et al., "Intact memory in TGF-β1 transgenic mice featuring chronic cerebrovascular deficit: recovery with pioglitazone," J. Cereb. Blood Flow Metab., 2011, 31:200-211.
Norata et al., "Effects of PCSK9 variants on common carotid artery intima media thickness and relation to ApoE alleles," Atherosclerosis, 2010 [Epub Jun. 27, 2009], 208: 177-182.
North et al., "Further investigation of linkage disequilibrium SNPs and their ability to identify associated susceptibility loci," Ann. Hum. Genet., 2004, 68:240-248.
Notice of Oppositions dated Oct. 15, 2014, in Chilean Patent Application No. 1947-2013, and Oppositions filed by Laboratorios Andromaco S.A. and Laboratorios Recalcine S.A.
Oda et al., "Apolipoprotein E polymorphism and renal disease," Kidney Int. Suppl., 1999, 71:S25-S27.
Office Action dated Apr. 16, 2013, in U.S. Appl. No. 13/058,724.
O'Keefe et al., "Alcohol and Cardiovascular Health," Journal of the American College of Cardiology, Sep. 11, 2007, 50(11):1009-1014.
Paternoster et al., "Association between apolipoprotein E genotype and carotid intima-media thickness may suggest a specific effect on large artery atherothrombotic stroke," Stroke, 2008, 39:48-54.
Pathan et al., "Chronic administration of pioglitazone attenuates intracerebroventricular streptozotocin induced-memory impairment in rats," Life Sci., 2006, 79:2209-2216.
Peck et al., "The genetics of primary haemorrhagic stroke, subarachnoid haemorrhage and ruptured intracranial aneurysms in adults," PLoS One, Nov. 2008, 3(11):e3691,1-12.
Pedersen et al., "Rosiglitazone attenuates learning and memory deficits in Tg2576 Alzheimer mice," Experimental Neurology, 2006, 199:265-273.
Pericak-Vance et al., "Linkage studies in familial Alzheimer disease: evidence for chromosome 19 linkage," Am. J. Hum. Genet., 1991, 48:1034-1050.
Pomara et al., "TOMM40 poly-T Variants and Cerebrospinal Fluid Amyloid Beta Levels in the Elderly," Neurochem. Res., 2011, 36:1124-1128.
Pomara et al., "Translocase of Outer Mitochondrial Membrane 40 Homolog (TOMM40) Poly-T Length Modulates Lorazepam-Related Cognitive Toxicity in Healthy APOE e4-Negative Elderly," Journal of Clinical Psychopharmacology, 2011, 31:544-546.
Ponce-Lopez et al., "Lithium, phenserine, memantine and pioglitazone reverse memory deficit and restore phosphor-GSK3β decreased in hippocampus in intracerebroventricular streptozotocin induced memory deficit model," Brain Research, Oct. 1, 2011, 1426:73-85.
Potkin et al., "Hippocampal atrophy as a quantitative trait in a genome-wide association study identifying novel susceptibility genes for Alzheimer's disease," PLoS ONE, Aug. 2009, 4(8):e6501, 1-15.
Rabiner et al., "Effects of 12 months of treatment with the PPARγ agonist rosiglitazone on brain glucose metabolism in Alzheimer's Disease: A $^{18}$F-FDG PET study," Presented at Alzheimer's Association International Conference on Alzheimer's Disease, Published in Alzheimers & Dementia 5: p. 207, p. 1-112.
Rannala et al. "Using linked markers to infer the age of a mutation," Hum. Mutat., 2001, 18(2):87-100.
Rasgon et al., "Insulin resistance and hippocampal volume in women at risk for Alzheimer's disease," Neurobiology of Aging, Nov. 2011, 32(11):1942-1948.
Reference SNP (refSNP) cluster report: rs10524523, printed on Apr. 10, 2013 from www.ncbi.nlm.nih.gov, 2 pages.
RefSNP Cluster Report rs10524523 [online] Jan. 24, 2006, 2 pages.
RefSNP Cluster Report rs10602329 [online] May 6, 2008, 2 pages.
Risner et al., "Efficacy of rosiglitazone in a genetically defined population with mild-to-moderate Alzheimer's disease," Pharmacogenomics J., 2006, 6(4):246-254.
Rodriguez-Rivera et al., "Rosiglitazone reversal of Tg2576 cognitive deficits is independent of peripheral gluco-regulatory status," Behavioural Brain Research, 2011, 216:255-261.
Roses AD et al., "Haplotypes Within the APOE LD Region May Have Pharmacogenetic Effects Predicting Efficacy of Alzheimer's Patients Receiving Rosiglitazone," Presented at IX International Meeting on Human Genome Variation and Complex Genome Analysis, Barcelona, Spain, Sep. 7, 2007.
Roses AD, "Alzheimer's disease—what is upstream from the amyloid cascade? Whole genome insights into new targets for therapy," Genome Medicine Seminar, Duke University, Jan. 2, 2008.
Roses AD, "An Inherited Variable Poly-T Repeat Genotype in TOMM40 in Alzheimer's Disease," Arch. Neurol., 2010, 67:536-541.
Roses AD, "NIA Workshop: The Role of ApoE and normal brain aging and Alzheimer's disease: Genetic basis for an APOE4-independent susceptibility locus related to mitochondrial metabolism," Aug. 13, 2008, 35 pages.
Roses AD, "On the discovery of the genetic association of Apolipoprotein E genotypes and common late-onset Alzheimer disease," Journal of Alzheimer's Disease, 2006, 9:361-366.
Roses et al., "A TOMM40 variable-length polymorphism predicts the age of late-onset Alzheimer's disease," Pharmacogenomics J., 2010 [Epub Dec. 22, 2009], 10: 375-384.
Roses et al., "APOEϵ3 and Tomm-40 Haplotypes Determine Inheritance of Alzheimer's Disease Independently of APOEϵ4 Risk," Presented at International Conference on Alzheimer's Disease, Vienna, Austria on Sunday, Jul. 12, 2009, 3:00 PM-3:15 PM Published in Alzheimer's & Dementia 5: e1, O1-06-01.
Roses et al., "Cis-acting human ApoE tissue expression element is associated with human pattern of intraneuronal ApoE in transgenic mice," Neurobiol. of Aging, 1998, 19(1S):S53-S58.
Roses et al., "Complex disease-associated pharmacogenetics: drug efficacy, drug safety, and confirmation of a pathogenetic hypothesis. (Alzheimer's disease)," Pharmacogenomics Journal, 2007, 7(1):10-28.
Roses et al., "TOMM40 "523" polyT allele frequencies in different ethnic groups," Presented at International Conference on Alzheimer's Disease, Honolulu, Hawaii on Jul. 10-15. Published in Alzheimer's and Dementia 4: e41, P4-067.
Roses, Allen D., "The Medical and Economic Roles of Pipeline Pharmacogenetics: Alzheimer's Disease as a Model of Efficacy and HLA-B*5701 as a Model of Safety," Neuropsychopharmacology, 2009, 34(1):6-17.

(56) References Cited

OTHER PUBLICATIONS

Salam et al., "Novel PPAR-γ agonists identified from a natural product library: a virtual screening, induced-fit docking and biological assay study," Chem. Biol. Drug Des., 2008, 71(1):57-70.

Sanderson MJ, "Phylogenetic signal in the eukaryotic tree of life," Science, Jul. 4, 2008, 321:121-123.

Sato et al., "Efficacy of PPAR-γ agonist pioglitazone in mild Alzheimer disease," Neurobiology of Aging, 2011, 32:1616-1633.

Sato et al., "Efficacy of PPAR-γ agonist pioglitazone in mild Alzheimer disease," Neurobiology of Aging, 2011, epub Nov. 17, 2009, 32:1626-1633.

Saunders et al., "Association of apolipoprotein E allele e4 with late-onset familial and sporadic Alzheimer's disease," Neurology, Aug. 1993, 43:1467-1472.

Schapira AH, "Mitochondrial disease," Lancet, Jul. 1, 2006, 368(9529):70-82.

Schellenberg GD, "Genetic dissection of Alzheimer disease, a heterogeneous disorder," Proc. Natl. Acad. Sci. USA, Sep. 1995, 92(19):8552-8559.

Schmitz et al., "Robust association of the APOE e4 allele with premature myocardial infarction especially in patients without hypercholesterolaemia: the Aachen study," European Journal of Clinical Investigation, 2007, 37:106-108.

Seltman et al., "Evolutionary-based association analysis using haplotype data," Genet. Epidemiol., 2003, 25(1):48-58.

Shadlen et al., "Research agenda for understanding Alzheimer disease in diverse populations: work group on cultural diversity, Alzheimer's association," Alzheimer Dis. Assoc. Disord., 2002, 16(Suppl2):S96-S100.

Shankaran et al., "Measurement of Brain Microglial Proliferation Rates In Vivo: A Biomarker for Discovering Novel Anti-Neoruinflammatory Agents," FASEB Journal, Mar. 6, 2006, 20(4, Part 1):A686-A687, 435.2. Meeting Info.: Experimental Biology 2006 Meeting. San Francisco, CA, USA. Apr. 1-5, 2006.

Sheline et al., "APOE4 Allele Disrupts Resting State fMRI Connectivity in the Absence of Amyloid Plaques or Decreased CSF Aβ42," The Journal of Neuroscience, Dec. 15, 2010, 30(50):17035-17040.

Shen et al., "Whole genome association study of brain-wide imaging phenotypes for identifying quantitative trait loci in MCI and AD: A study of the ADNI cohort," NeuroImage, 2010, 1051-1063.

Stone et al., "ApoE genotyping as a progression-rate biomarker in phase II disease-modification trials for Alzheimer's disease," Pharmacogenomics Journal, 2010, 10(3):161-164.

Sun et al., "Genetic variability in inflammation pathways and prostate cancer risk," Urol. Oncol., 2007, 25(3):250-259.

Sun et al., "Interactions of sequence variants in interleukin-1 receptor-associated kinase4 and the toll-like receptor 6-1-10 gene cluster increase prostate cancer risk," Cancer Epidemiol. Biomarkers Prev., Mar. 2006, 15(3):480-485.

Sun et al., "Sequence variants in Toll-like receptor gene cluster (TLR6-TLR1-TLR10) and prostate cancer risk," J. Natl. Cancer Inst., Apr. 6, 2005, 97(7):525-532.

Takei et al., "Genetic association study on in and around the APOE in late-onset Alzheimer disease in Japanese," Genomics, 2009, 93(5):441-448.

Templeton et al., "Tree Scanning: A Method for Using Haplotype Trees in Phenotype/Genotype Association Studies," Genetics, Jan. 2005, 169:441-453.

Tsukuda et al., "Cognitive Deficit in Amyloid-β-Injected Mice Was Improved by Pretreatment with a Low Dose of Telmisartan Party Because of Peroxisome Proliferator-Activated Receptor-γ Activation," Hypertension, Oct. 2009, 54(4):782-787.

Tzeng JY, "Evolutionary-based grouping of haplotypes in association analysis," Genet. Epidemiol., 2005, 28(3):220-231.

Tzimopoulou et al., "A Multi-Center Randomized Proof-of-Concept Clinical Trial Applying [$^{18}$F]FDG-PET Evaluation of Metabolic Therapy with Rosiglitazone XR in Mild to Moderate Alzheimer's Disease," Journal of Alzheimer's Disease, 2010, 22:1241-1256.

Vellas et al., "Endpoints for trials in Alzheimer's disease: a European task force consensus," Lancet Neurol., May 2008, 7:436-450.

Wada et al., "Peroxisome Proliferator-activated Receptor γ-mediated Regulation of Neural Stem Cell Proliferation and Differentiation," Journal of Biological Chemistry, May 5, 2006; 281(18):12673-12681.

Wallace DC, "Mitochondrial diseases in man and mouse," Science, Mar. 5, 1999, 283(5407):1482-1488.

Waring et al., "Genome-wide association studies in Alzheimer disease," Arch. Neruol., Mar. 2008, 65(3):329-334.

Washida et al., "Nonhypotensive Dose of Telmisartan Attenuates Cognitive Impairment Partially Due to Peroxisome Proliferator-Activated Receptor-γ Activation in Mice With Chronic Cerebral Hypoperfusion," Stroke, Aug. 2010, 41(8):1798-1806.

Watson et al., "Insulin resistance, inflammation, and cognition in Alzheimer's Disease: Lessons for multiple sclerosis," Journal of the Neurological Sciences, Jun. 15, 2006, 245(1-2):21-33.

Watson et al., "Pioglitazone modulates plasma levels of β-amyloid in glucose intolerant older adults," Alzheimer's and Dementia, 2007, 3: S164, P-206.

Watson et al., "The Role of Insulin Resistance in the Pathogenesis of Alzheimer's Disease: Implications for Treatment," CNS Drugs, 2003, 17(1): 27-45.

Welsh, EM [Editor]. (2006) Frontiers in Alzheimer's Disease Research, Table of Contents, Publisher: Nova Science Publishers, Inc.

Wijsman et al., "Genome-Wide Association of Familial Late-Onset Alzheimer's Disease Replicates BIN1 and CLU and Nominates CUGBP2 in Interaction with APOE," PLoS Genet., 2011, 7(2): e1001308, 1-19.

World Alzheimer Report 2009, Alzheimer's Disease International, Prince M and Jackson J, eds., pp. 1-93.

Yu et al., "Comprehensive analysis of APOE and selected proximate markers for late-onset Alzheimer disease: Patterns of linkage disequilibrium and disease/marker association," Genomics, Jun. 2007, 89(6):655-665.

Zhang et al., "Mining biomarkers in human sera using proteomic tools," Proteomics, Jan. 2004, 4(1):244-256.

Chiang et al., "Hippocampal atrophy rates and CSF biomarkers in elderly APOE2 normal subjects," Neurology, Nov. 30, 2010, 75(22)1978-1981.

METHODS AND DRUG PRODUCTS FOR TREATING ALZHEIMER'S DISEASE

RELATED APPLICATIONS

This application is a Continuation of U.S. application Ser. No. 13/346,081, which claims the benefit under 35 U.S.C. §119(e) of U.S. Provisional Patent Application No. 61/431,370, filed Jan. 10, 2011.

FIELD OF THE INVENTION

The present invention relates to a method and drug product for treating a subject who is at risk to develop Alzheimer's disease.

BACKGROUND

Alzheimer's disease is a neurodegenerative disease and the most common cause of dementia. This disease manifests as a gradual but progressive decline in memory, thinking skills and behavior that is accelerated relative to normal aging (Reitz et al. 2011 Nat Rev Neurol 7: 137-152). Eventually, patients are unable to recognize familiar people or carry out the simplest task. Alzheimer's disease is, at this time, the sixth leading cause of death in the United States (US).

There are two predominant forms of the disease: Familial Alzheimer's disease is typically caused by dominant mutations in one of three genes (APP, PSEN1 or PSEN2). This form of the disease is a rare and devastating illness with onset occurring in mid-life. The second and far more common form of the disease is Sporadic or Late onset Alzheimer's disease (hereinafter "Alzheimer's disease" or "AD"). Onset of Alzheimer's disease typically occurs after the age of 62 years.

As the world population and human longevity increase, so do the numbers of people affected by Alzheimer's disease globally. The estimated worldwide costs of dementia, of which Alzheimer's disease accounts for up to 80% of cases, was US$604 billion in 2010, which was greater than 1% of US GDP (Wimo and Prince 2010 World Alzheimer Report 2010: The Global Economic Impact of Dementia 1-93). The cost of caring for Alzheimer patients in the US is expected to increase from US$172 million in 2010, to US$1.07 trillion in 2050 (Alzheimer's Association. "Changing the Trajectory of Alzheimer's Disease: A National Imperative (2010)").

At this time, the few drugs that are approved for treatment of this disease provide some symptomatic relief, but this is typically of relatively short duration, and the therapies do not alter the course of disease progression (Alzheimer's Association. "Changing the Trajectory of Alzheimer's Disease: A National Imperative (2010)"). Therapies that delay the onset of the disease, reduce the rate of disease progression, or that can do both are urgently needed. Therapies that can achieve either of these goals will reduce the number of individuals with disease, or reduce the number of individuals with the more advanced and debilitating stages of disease (Brookmeyer et al. 2007 Alzheimers Dement 3: 186-191). It is projected that if the onset of Alzheimer's disease is delayed by 5 years due to availability of a breakthrough therapy in 2015, 43% of the 13.5 million Americans expected to have the condition in 2050 would not have the disease, and there will be fewer people with advanced disease.

The principal risk factor for Alzheimer's disease is age, and prevalence of the disease increases with age (approximately 10% of individuals over 65 and approximately 50% of individuals over 85). The incidence of the disease doubles every 5 years after 65 years of age, with the diagnosis of about 1275 new cases per year per 100,000 persons older than 65 years of age (Querfurth et al., 2010 NEJM 362:4). Both men and women are affected by Alzheimer's disease, but women generally represent a higher percentage of cases overall (roughly 60% to 40%), possibly due to greater longevity. People suffering from Alzheimer's disease tend to live approximately 3 to 9 years after diagnosis, on average.

The epsilon 4 allele of APOE has previously been associated with increased risk of developing Alzheimer's disease. (Pericak-Vance et al. 1991 Am J Hum Genet 48: 1034-1050; Martin et al. 2000 Am J Hum Genet 67: 383-394; U.S. Pat. Nos. 6,027,896 and 5,716,828 to Roses et al.) The relationship is copy number dependent (Yoshizawa et al. 1994 Ann Neurol 36: 656-659). That is to say, a carrier of two APOE4 alleles is more likely to develop late-onset Alzheimer's disease (LOAD) than a carrier of only one APOE4 allele, and at an earlier age (Corder et al. 1993 Science 261, 921-3).

Nevertheless, APOE4 alleles only account for roughly 50% of the inherited risk of late onset Alzheimer's disease. One explanation is that APOE4 is merely serving as a surrogate marker for something in linkage disequilibrium nearby. Alternatively, considering the recent discovery of a mechanistic role for APOE4 in mitochondrial toxicity, the negative effects of APOE4 may be abrogated or exacerbated by another gene product that may be encoded nearby (Chang et al. 2005 Proc Natl Acad Sci USA 102: 18694-18699).

The symptoms of Alzheimer's disease are primarily marked by cognitive deficits including memory impairment, language dysfunction, and visuospatial skills; functional impairment that may span occupational and social issues (e.g., activities of daily living); and behavioral symptoms including depression, anxiety, aggression and psychosis may also appear as the disease progresses in severity.

At this time, unambiguous diagnosis of Alzheimer's disease requires clinical findings of cognitive deficits consistent with AD and post-mortem identification of brain pathologies consistent with AD. The term AD dementia is used to describe dementia that is due to the pathophysiologies of Alzheimer's disease. The term "probable Alzheimer's disease" is used in life when a subject demonstrates clinical characteristics of Alzheimer's disease and when other possible biological causes of dementia (e.g. Parkinson's disease or stroke) are excluded.

There are currently a variety of art-accepted methods for diagnosing probable Alzheimer's disease. Typically, these methods are used in combination. These methods include determining an individual's ability to carry out daily activities and identifying changes in behavior and personality. Dementia of the AD type is also typically characterized by an amnestic presentation (memory deficit) or language, visuospatial or executive function deficits. Cognitive ability/impairment may be determined by art-accepted methods, including, but not limited to, validated instruments that assess global cognition (e.g., the Modified Mini Mental State Examination (3MS-E)), and specific domains such as visual and verbal memory (e.g., the Brief Visuospatial Memory Test (Revised) (BVMT-R) and the Hopkins Verbal Learning Test (Revised) (HVLT-R), respectively), language (e.g., the Generative Verbal Fluency Test (GVFT)) and executive function and attention (e.g., the Digit Span Test (DST)). Dementia due to AD is also defined by insidious onset and a history of worsening cognitive performance.

The criteria for 'probable Alzheimer's disease' were recently updated by a National Institute of Aging-Alzheimer's Association workgroup (McKhann et al. 2011 Alzheimers Dement 7: 263-269). This workgroup recommended that, for people who first exhibit the core clinical characteristics of Alzheimer's disease dementia, evidence of biomarkers associated with the disease may enhance the certainty of the diagnosis.

In view of the fact that more than 4.5 million people in the United States alone suffer from Alzheimer's disease (and this number will continue to grow as the population ages), the cruel and unforgiving degenerative and debilitative nature of Alzheimer's disease as it develops, and the high costs associated with the care for people suffering from Alzheimer's disease, there is a real and immediate need for an effective medical therapy that can delay the onset of Alzheimer's disease.

BRIEF SUMMARY OF THE INVENTION

Provided herein are compositions including low dose pioglitazone, which compositions are useful in treating mild cognitive impairment (e.g., cognitive impairment of the Alzheimer's type). In some embodiments, treating includes delaying the onset of mild cognitive impairment. In some embodiments, treating includes delaying the onset of mild cognitive impairment in a cognitively normal subject. In some embodiments, the delaying includes delaying the onset of impairment in episodic memory.

In some embodiments, treating includes delaying the onset of mild cognitive impairment in a human subject at increased risk of developing cognitive impairment within the next 5-7 years, said risk based upon the subject's age, or based upon the subject's age and TOMM40 rs10524523 genotype.

In some embodiments, low dose pioglitazone is administered in unit dosage form, e.g., having from 0.5, 1, 1.5 or 2, to 6, 8, 10 or 12 milligrams of pioglitazone or a pharmaceutically acceptable salt thereof.

Also provided is the use of low dose pioglitazone in the manufacture of a pharmaceutical formulation for the treatment of mild cognitive impairment (e.g., cognitive impairment of the Alzheimer's type). In some embodiments, the pharmaceutical formulation is a tablet. In some embodiments, the pharmaceutical formulation is a capsule. In some embodiments, the pharmaceutical formulation is a caplet. In some embodiments, the pharmaceutical formulation is a liquid. In some embodiments, the pharmaceutical formulation is a solid or semi-solid.

Also provided is a composition including low dose pioglitazone for use in the treatment of cognitive decline.

Further provided are methods for treating mild cognitive impairment (e.g., cognitive impairment of the Alzheimer's type) in a human subject in need thereof, comprising administering to the subject low dose pioglitazone. In some embodiments, the treating includes delaying the onset of mild cognitive impairment. In some embodiments, treating includes delaying the onset of mild cognitive impairment in a cognitively normal subject. In some embodiments, the delaying includes delaying the onset of impairment in episodic memory.

In some embodiments, the subject is at increased risk in developing cognitive impairment of the Alzheimer's type within the next 5-7 years, said risk based upon the subject's age, or based upon the subject's age and rs10524523 ('523) genotype.

In some embodiments, the subject is at least 50, 55, 60, 62, 68, or 70 years old.

In some embodiments, the subject is a Caucasian subject. In some embodiments, the subject is a non-Caucasian subject.

In some embodiments, the subject does not have one or two APOE2 alleles.

In some embodiments, low dose pioglitazone is administered in unit dosage form, e.g., having from 0.5, 1, 1.5 or 2, to 6, 8, 10 or 12 milligrams of pioglitazone. In some embodiments, the administering is once daily.

In some embodiments, pioglitazone is provided as or administered at a dosage that provides an AUC of from about 0.15 μg·h/mL to about 3.6 μg·h/mL. In some embodiments, pioglitazone is provided as or administered at a dosage that provides an AUC of from 0.12 μg·h/mL to 4.5 μg·h/mL. In some embodiments, pioglitazone is provided as or administered at a dosage that provides an AUC of from 0.12 μg·h/mL to 3.4 μg·h/mL.

Also provided are methods of treating cognitive decline in a human subject in need thereof, including administering to said subject low dose pioglitazone.

Still further provided are methods of determining increased risk in developing cognitive impairment of the Alzheimer's type in a human subject at a predetermined age or age range, including:

detecting from a biological sample of said subject the '523 genotype of said subject, wherein each allele of '523 is assigned as:
    (a) short (S, less than 19 T residues);
    (b) long (L, 19-29 residues); or
    (c) very long (VL, 30 or more residues); and
determining from said '523 genotype whether said subject is at increased risk in developing cognitive impairment of the Alzheimer's type at said predetermined age or age range, wherein:
    (1) age greater than about 62 and L,L or L,VL indicates increased risk;
    (2) age greater than about 62 and VL,VL does not indicate increased risk;
    (3) age greater than about 74 and S,L indicates increased risk;
    (4) age greater than about 77 and S,S indicates increased risk; and
    (5) age greater than about 76 and S,VL indicates increased risk.

In some embodiments, the determining further includes detecting from a biological sample of said subject the APOE genotype of said subject, wherein the presence of an APOE2 allele in said genotype indicates the subject is not at increased risk.

Also provided are methods of determining whether to administer low dose pioglitazone to a human subject for treatment of cognitive impairment of the Alzheimer's type, including:

detecting from a biological sample of said subject the '523 genotype of the subject, wherein each allele is assigned as:
    (a) short (S, less than 19 T residues);
    (b) long (L, 19-29 residues); or
    (c) very long (VL, 30 or more residues); and
determining from said '523 genotype and from the age of said human subject whether to administer low dose pioglitazone to said subject for treatment of cognitive impairment of the Alzheimer's type, wherein:

(1) age greater than about 62 and L,L or L,VL indicates treatment;
(2) age greater than about 62 and VL,VL does not indicate treatment;
(3) age greater than about 74 and S,L indicates treatment;
(4) age greater than about 77 and S,S indicates treatment; and
(5) age greater than about 76 and S,VL indicates treatment.

In some embodiments, the determining further includes detecting from a biological sample of said subject the APOE genotype of said subject, wherein the presence of an APOE2 allele in said genotype does not indicate treatment.

In some embodiments of any of the above methods or compositions, the subject has normal cognition.

Still further provided are methods of delaying the onset of Alzheimer's disease, wherein the method comprises (a) detecting a variant to the TOMM40 gene in a subject who is at-risk to develop Alzheimer's disease, and (b) administering a drug product that contains an effective low dose pioglitazone or pioglitazone salt to the at-risk subject detected with the TOMM40 variant to delay the onset of Alzheimer's disease. For example, the present invention contemplates (a) detecting a variant of the TOMM40 gene, such as a long poly-T allele (greater than 19 Thymidine residues), in a subject who is at-risk to develop Alzheimer's disease, and (b) administering an effective amount of low dose pioglitazone or pioglitazone salt drug product of the at-risk subject detected with the long poly-T allele variant of the TOMM40 gene, who may for example be in a normal cognitive stage, to delay the onset of Alzheimer's disease.

Also provided are methods of delaying the onset of one or more stages that progress to Alzheimer's disease, such as the mild cognitive impairment stage, the amnestic mild cognitive impairment stage, the preclinical Alzheimer's disease stage and/or the prodromal Alzheimer's disease stage, in a subject at-risk to develop Alzheimer's disease, wherein the method comprises: (a) detecting in a subject who is at-risk to develop Alzheimer's disease a variant to the TOMM40 gene, such as a long poly-T allele (greater than 19 Thymidine residues); and (b) administering a drug product that contains an effective amount of low dose pioglitazone or pioglitazone salt to the at-risk subject in whom the TOMM40 variant has be detected to delay the onset of one or more of the stages that progress to Alzheimer's disease, including any cognitive impairment or other stage, to delay the onset of Alzheimer's disease in the at-risk subject. It should be understood that, in accordance with this method of the present invention, the at-risk subject, at time of detection of the TOMM40 variant and/or treatment, may be in a normal cognitive stage or in any one of the stages that progress to Alzheimer's disease.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF THE INVENTION

Figure 1:
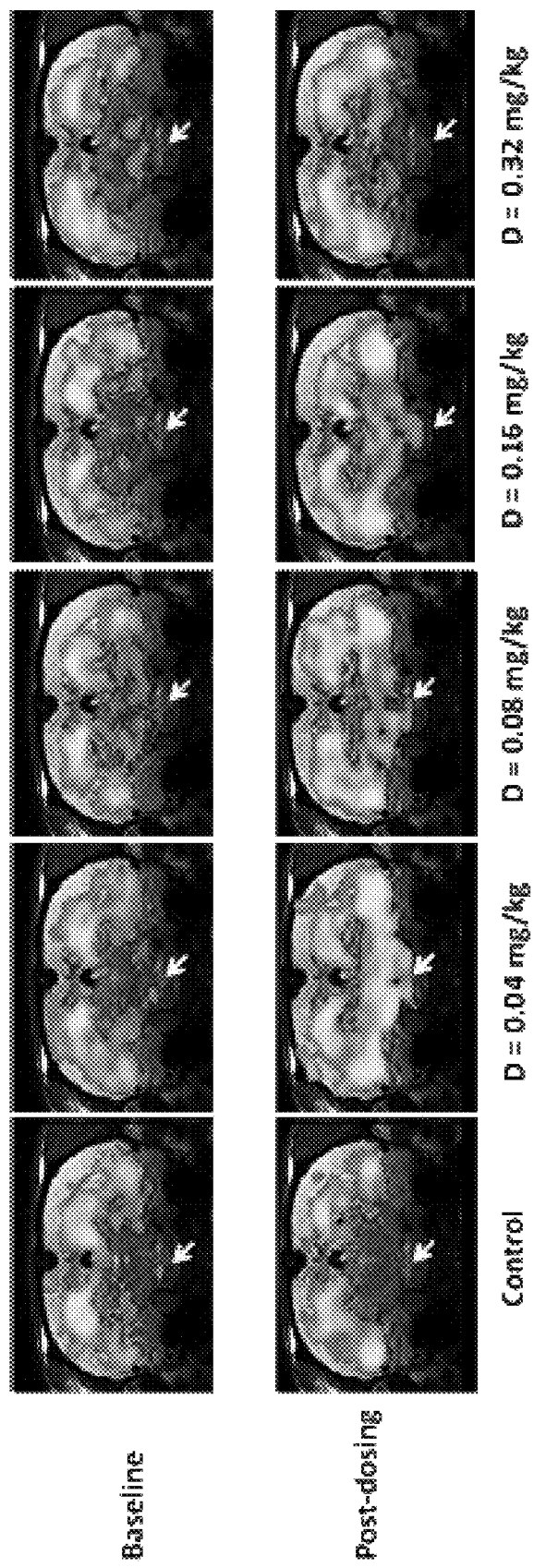
FIG. 1 presents fMRI images of rat brain at multiple doses of PIO relative to vehicle control. The top panel shows the group-averaged fMRI signal at baseline; the bottom panel illustrates the group-averaged fMRI signal at treatment day 7. This analysis shows that pioglitazone HCl at doses as low as 0.04 mg/kg/day induces change in metabolism in deep subcortical structure of the rat brain.

By way of illustrating and providing a more complete appreciation of the present invention and many of the attendant advantages thereof, the following detailed description and examples are given concerning the novel methods and compositions.

In one aspect, the present invention relates to a pharmaceutical composition, i.e., a drug product, comprising low dose pioglitazone or a pharmaceutically acceptable salt thereof and a pharmaceutically acceptable vehicle for administration to a subject, such as a human patient in need of treatment to delay the onset of or otherwise treat Alzheimer's disease in such a patient. While the present invention may be embodied in many different forms, several specific embodiments are discussed herein with the understanding that the present disclosure is to be considered only as an exemplification of the principles of the invention, and it is not intended to limit the invention to the embodiments described or illustrated.

I. Definitions

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Singular word forms are intended to include plural word forms and are likewise used herein interchangeably where appropriate and fall within each meaning, unless expressly stated otherwise.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about".

All parts, percentages, ratios, etc. herein are by weight unless indicated otherwise.

As used herein, "bioequivalence" or "bioequivalent", refers to low dose pioglitazone formulations or drug products which are pharmaceutically equivalent, and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which pioglitazone becomes available from such formulations at the site of pioglitazone action when administered at the same molar dose under similar conditions, e.g., the rate at which pioglitazone can leave such a formulation and the rate at which pioglitazone can be absorbed and/or become available at the site of action to affect Alzheimer's disease. In other words, there is a high degree of similarity in the bioavailabilities of two pioglitazone pharmaceutical products (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the United States Food and Drug Administration (FDA), (b) the Code of Federal Regulations ("C.F.R."), Title 21, (c) Health Canada, (d) European Medicines Agency (EMEA), and/or (e) the Japanese Ministry of Health and Welfare. Thus, it should be understood that the present invention contemplates low dose pioglitazone formulations or drug products that may be bioequivalent to other low dose pioglitazone formulations or drug products of the present invention. By way of example, a first low dose pioglitazone formulation or drug product is bioequivalent to a second low dose pioglitazone formulation or drug product, in accordance with the present invention, when the measurement of at least one pharmacokinetic parameter(s), such as a Cmax, Tmax, AUC, etc., of the first low dose pioglitazone formulation or drug product varies by no more than about ±25%, when compared to the measurement of the same pharmacokinetic parameter for the second low dose pioglitazone formulation or drug product.

As used herein, "bioavailability" or "bioavailable" means generally the rate and extent of absorption of pioglitazone into the systemic circulation and, more specifically, the rate or measurements intended to reflect the rate and extent to which pioglitazone becomes available at the site of action or is absorbed from a drug product and becomes available at the site of action. In other words, and by way of example, the extent and rate of pioglitazone absorption from a lower dosage strength formulation of the present invention as reflected by a time-concentration curve of pioglitazone in systemic circulation.

By way of further example, bioavailability is a measurement of the extent of a therapeutically active drug that reaches the systemic circulation and is available at the site of action. It is expressed as the letter F.

With respect to absolute bioavailability, absolute bioavailability compares the bioavailability (estimated as area under the curve, or AUC) of the active drug in systemic circulation following non-intravenous administration (i.e., after oral, rectal, transdermal, subcutaneous administration), with the bioavailability of the same drug following intravenous administration. It is the fraction of the drug absorbed through non-intravenous administration compared with the corresponding intravenous administration of the same drug. The comparison must be dose normalized if different doses are used; consequently, each AUC is corrected by dividing the corresponding dose administered.

In order to determine absolute bioavailability of a drug, a pharmacokinetic study must be done to obtain a plasma drug concentration vs time plot for the drug after both intravenous (IV) and non-intravenous administration. The absolute bioavailability is the dose-corrected area under curve (AUC) non-intravenous divided by AUC intravenous. For example, the formula for calculating F for a drug administered by the oral route (po) is given below.

$$F = \frac{[AUC]_{po} * \text{dose}_{IV}}{[AUC]_{IV} * \text{dose}_{po}}$$

Therefore, a drug given by the intravenous route will have an absolute bioavailability of 1 (F=1) while drugs given by other routes usually have an absolute bioavailability of less than one.

With respect to relative bioavailability, this measures the bioavailability (estimated as area under the curve, or AUC) of a certain drug when compared with another formulation of the same drug, usually an established standard, or through administration via a different route. When the standard consists of intravenously administered drug, this is known as absolute bioavailability.

$$\text{relative bioavailability} = \frac{[AUC]_A * \text{dose}_B}{[AUC]_B * \text{dose}_A}$$

As used herein, the terms "pharmaceutical equivalence" or "pharmaceutically equivalent" refer to low dose pioglitazone formulations or drug products of the present invention that contain the same amount of pioglitazone, in the same dosage forms, but not necessarily containing the same inactive ingredients, for the same route of administration and meeting the same or comparable compendial or other applicable standards of identity, strength, quality, and purity, including potency and, where applicable, content uniformity and/or stability. Thus, it should be understood that the present invention contemplates low dose pioglitazone formulations or drug products that may be pharmaceutically equivalent to other low dose pioglitazone formulations or drug products used in accordance with the present invention.

As used herein, the terms "therapeutic equivalence or therapeutically equivalent" mean those low dose pioglitazone formulations or drug products which (a) will produce the same clinical effect and safety profile when utilizing pioglitazone drug product to delay onset of Alzheimer's disease in accordance with the present invention and (b) are pharmaceutical equivalents, e.g., they contain pioglitazone in the same dosage form, they have the same route of administration; and they have the same pioglitazone strength. In other words, therapeutic equivalence means that a chemical equivalent of a lower dosage strength pioglitazone formulation of the present invention (i.e., containing the same amount of pioglitazone in the same dosage form when administered to the same individuals in the same dosage regimen) will provide essentially the same efficacy and toxicity.

"Alzheimer's disease", "Alzheimer disease", or "AD" as used herein is a disease in which cognitive function is impaired gradually over time, and includes a symptomatic pre-dementia phase with presentation of mild cognitive impairment (MCI), and a dementia phase, where there is a significant impairment in social or occupational functioning. See Albert et al. 2011 Alzheimer's & Dementia 7: 270-279; McKhann et al. 2011 Alzheimer's & Dementia 7: 263-269.

Though a number of biomarkers are reported to coincide with Alzheimer's disease, none are recognized as validated or qualified biomarkers for the diagnosis or prognosis of Alzheimer's disease by the US Food and Drug Administration. From a clinical standpoint, the hallmark feature that is consistently present and needed for the diagnosis of Alzheimer's disease is cognitive impairment.

Indications of cognitive impairment may include, but are not limited to, difficulty with mental functions such as language, memory (e.g., episodic), perception, emotional behavior or personality, cognitive skills (e.g., calculation, abstract thinking, judgment). The determination may be obtained from the patient, from an informant who knows the patient well, from a skilled clinician observing the patient, or a combination thereof.

"Mild cognitive impairment" or "MCI" refers to a reduction in cognitive ability that is greater than anticipated considering a person's age or education in one or more cognitive domains. The cognitive domains include memory, executive functions (e.g., problem-solving, planning or reasoning), attention (e.g., simple and divided attention), visuospatial skill, and language (e.g., naming, fluency, expressive speech, comprehension). Symptoms of MCI may include difficulties identifying the right word or name; difficulty remembering names when introduced to new people; noticeably greater difficulty performing tasks in social or work settings; forgetting material that one has just read; losing or misplacing a valuable object; increasing trouble with planning or organizing; difficulty mastering new skills; concentration deficits; and increased anxiety. Mild cognitive impairment is a phase at which symptoms are sufficient to meet the currently accepted criteria of MCI, but where symptoms do not meet dementia diagnostic criteria. People with MCI, however, may remain functionally intact and independent. If formal, standardized cognitive tests are administered, people with MCI generally score 1 to 1.5 standard deviations below the age and education-adjusted mean for their peers. It should be noted that not all MCI leads to dementia, nor to Alzheimer's disease.

"Cognitive Impairment of the Alzheimer's Type" or "CIAT" as used herein refers to cognitive impairment consistent with features wherein Alzheimer's is the likely cause, and thus may be considered a subset of MCI. The designations, "Cognitive Impairment of the Alzheimer's Type", "Mild Cognitive Impairment due to Alzheimer's disease (MCI due to AD)" or "amnestic Mild Cognitive Impairment (aMCI)" refer to the symptomatic, pre-dementia phase of Alzheimer's disease. CIAT or MCI due to AD is determined following use of neuropsychological tests and clinician assessment of the cognitive function of the individual. Typically, episodic memory is impaired in person with MCI that progresses to AD (aMCI). However, there are atypical forms of MCI—MCI with nonamnestic presentation—that also progress to Alzheimer's disease. Progressive decline in cognitive function provides additional evidence that a person suffers MCI due to AD.

There are a number of neuropsychological assessments, particularly those that test episodic memory (i.e., the ability to learn and retain new information), that are useful in diagnosing MCI due to AD, or those patients with MCI who are likely to progress to AD within a few years. Tests of episodic memory may assess immediate and/or delayed recall, such as word-list learning tests. In addition, an alternative etiology for the cognitive impairment, such as degenerative (e.g., Parkinsonism), vascular events including microinfarcts, depressive, traumatic, medical comorbidities, should be ruled out. A number of biomarkers have been proposed for use in research and may also be useful in supporting the clinical diagnosis of MCI due to AD by confirming the presence of pathologies consistent with AD or to monitor progression of the disease, if desired. See, e.g., Albert et al. 2011 Alzheimer's & Dementia 7: 270-279.

In accordance with the present invention, cognitive impairment may be determined by any art-accepted method of cognitive assessment, including, but not limited to, an assessment of global cognition (e.g., the Modified Mini Mental State Examination (3MS-E)), and specific domains such as visual and verbal memory (e.g., the Brief Visuospatial Memory Test (Revised) (BVMT-R) and the Hopkins Verbal Learning Test (Revised) (HVLT-R), respectively), language (e.g., the Generative Verbal Fluency Test (GVFT)) and executive function and attention (e.g., the Digit Span Test (DST)).

Physiological changes may or may not also be detected. "Physiological changes" means, for example, the occurrence of at least one of altered functional connectivity, brain atrophy, decreased synaptic activity in the brain, increased amyloid accumulation in the brain, decreased mitochondrial function or increased mitochondrial dysfunction in the brain, neuronal formation of neurofibrillary tangles in the brain, and a change corresponding to any other symptom of Alzheimer's disease. Physiological changes that can be indicative of Alzheimer's disease include, but are not limited to, hypometabolism in the brain, altered functional connectivity, increased beta amyloid in the brain and or CSF and tau and phospho-tau in the CSF.

As used herein, "onset" means the occurrence in a subject of clinical symptoms associated or consistent with a diagnosis Alzheimer's disease or a phase that progresses to Alzheimer's dementia, such as CIAT, as defined herein.

As used herein, "delay" in the onset or progression of a phase consistent with Alzheimer's disease means an increase in time from a first time point to onset or worsening of a phase consistent with Alzheimer's disease, such as cognitive impairment of the Alzheimer type. For example, a delay in the onset of Alzheimer's disease means that the onset of Alzheimer's disease, as defined herein, in a subject at risk to develop Alzheimer's disease is delayed from happening at its natural time frame by at least six months, 1 year, 1½ years, 2, years, 2½ years, 3 years, 3½ years, 4 years, 4½ years, 5 years, 5½ years, 6 years, 6½ years, 7 years, 7½ years or 8 years or more, and preferably from 3 years to 8 years and more preferably for 5 years after a normal cognitive subject has been determined to be at high risk to develop Alzheimer's disease. By way of further example, a delay in the progression of cognitive impairment that may progress to Alzheimer's disease or a delay in the progression of dementia means that the rate of cognitive decline is slowed relative to its natural time frame. These determinations are performed by using appropriate statistical analysis.

A "first time point" includes, for example, the initiation of low dose pioglitazone treatment as taught herein.

In some embodiments, a delay in the onset of cognitive impairment consistent with Alzheimer's disease can be determined by, for example, performing any of the cognitive assessments described herein or by meeting accepted diagnostic criteria for cognitive impairment of the Alzheimer's type. In addition to the assessment of cognitive performance, changes in other biomarkers that are consistent with Alzheimer's disease pathologies may also be measured, if desired, including the rate of brain atrophy, for example measured by magnetic resonance imaging (MRI) or measurement of the changes in functional connections between brain regions, assessment of brain metabolism or neuronal activity, amyloid accumulation in the brain, brain physiology as measured by BOLD-fMRI signal, mitochondrial function in the brain, mitochondrial proliferation in the brain, diseased neurons, neurofibrillary tangles in the brain, amyloid in the CSF and Tau or phospho-Tau in the CSF, etc.

"Diagnosis" or "prognosis" as used herein refer to the use of information (e.g., genetic information or data from other molecular tests, biological or chemical information from biological samples, signs and symptoms, physical exam findings, cognitive performance results, etc.) to anticipate the most likely outcomes, timeframes, and/or responses to a particular treatment for a given disease, disorder, or condition, based on comparisons with a plurality of individuals sharing common nucleotide sequences, symptoms, signs, family histories, or other data relevant to consideration of a patient's health status, or the confirmation of a subject's affliction, e.g., with mild cognitive impairment (MCI) (e.g., cognitive impairment of the Alzheimer's type).

"Biological sample," as used herein, refers to a material containing, for example, a nucleic acid, protein or other biological or chemical material of interest. Biological samples containing nucleic acid such as DNA include hair, skin, cheek swab, and biological fluids such as blood, serum, plasma, sputum, lymphatic fluid, semen, vaginal mucus, feces, urine, spinal fluid, and the like. Isolation of DNA from such samples is well known to those skilled in the art.

A "subject" according to some embodiments is an individual whose genotype(s) or haplotype(s) are to be determined and recorded in conjunction with the individual's condition (i.e., disease or disorder status) and/or response to a candidate drug or treatment.

"Subject," as used herein, is preferably, but not necessarily limited to, a human subject. The subject may be male or female and may be of any race or ethnicity, including, but not limited to, Caucasian, African-American, African, Asian, Hispanic, Indian, etc. The subject may be of any age, including newborn, neonate, infant, child, adolescent, adult, and geriatric. Subject as used herein may also include an animal, particularly a mammal such as a canine, feline, bovine, caprine, equine, ovine, porcine, rodent (e.g., a rat and mouse), a lagomorph, a primate (including non-human primate), etc., that may be treated in accordance with the methods of the present invention or screened for veterinary medicine or pharmaceutical drug development purposes. A subject according to some embodiments of the present invention include a patient, human or otherwise, in need of therapeutic treatment to delay onset of Alzheimer's disease.

"Gene," as used herein, means a segment of DNA that contains information for the regulated biosynthesis of an RNA product, including promoters, exons, introns, and other untranslated regions that control expression.

A "genetic risk factor," as used herein, means a genetic marker that is associated with increased susceptibility to a condition, disease, or disorder. It may also refer to a genetic marker that is associated with a particular response to a selected drug or treatment of interest. "Associated with" as used herein means the occurrence together of two or more characteristics more often than would be expected by chance alone. An example of associated with involves a feature on the surface of white blood cells called HLA (HLA stands for human leukocyte antigen). A particular HLA type, HLA type B-27, is associated with an increased risk for a number of diseases including ankylosing spondylitis. Ankylosing spondylitis is 87 times more likely to occur in people with HLA B-27 than in the general population.

A "prognostic" marker may be used to predict the probable course of a condition or disease, including, but not limited to, prediction of the probable age of onset of the condition or disease, course and/or rate of progression of the condition or disease, etc. It could include genotype and/or other variables, including age of the subject.

A subject "at increased risk of developing a condition" due to a genetic risk factor is one who is predisposed to the condition, has genetic susceptibility for the condition, and/or is more likely to develop the condition than subjects in which the genetic risk factor is absent. A subject "at increased risk" may also be a subject who is susceptible to developing the disease at an earlier age.

As used herein, a subject "at-risk of developing Alzheimer's disease" includes an individual that is more likely to develop Alzheimer's disease based on one or more of: age; rs10524523 genotype; APOE genotype, etc.

"Polymorphism," as used herein, refers to the existence of two or more different nucleotide sequences at a particular locus in the DNA of the genome. Polymorphisms can serve as genetic markers and may also be referred to as genetic variants. Polymorphisms include nucleotide substitutions, insertions, deletions and microsatellites, and may, but need not, result in detectable differences in gene expression or protein function. A polymorphic site is a nucleotide position within a locus at which the nucleotide sequence varies from a reference sequence in at least one individual in a population.

A "deletion/insertion polymorphism" or "DIP," as used herein, is an insertion of one or more nucleotides in one version of a sequence relative to another. If it is known which of the alleles represent minor alleles, the term "deletion" is used when the minor allele has a deletion of one or more nucleotides, and the term "insertion" is used when the minor allele has an additional one or more nucleotides. The term "deletion/insertion polymorphism" is also used when there are multiple forms or lengths and it is not apparent which is the minor allele. For example, for the poly-T polymorphisms described herein, multiple lengths of polymorphisms are observed.

"Haplotype," as used herein, refers to a genetic variant or combination of variants carried on at least one chromosome in an individual. A haplotype often includes multiple contiguous polymorphic loci. All parts of a haplotype, as used herein, occur on the same copy of a chromosome or haploid DNA molecule. Absent evidence to the contrary, a haplotype is presumed to represent a combination of multiple loci that are likely to be transmitted together during meiosis. Each human carries a pair of haplotypes for any given genetic locus, consisting of sequences inherited on the homologous chromosomes from two parents. These haplotypes may be identical or may represent two different genetic variants for the given locus. Haplotyping is a process for determining one or more haplotypes in an individual. Haplotyping may include use of family pedigrees, molecular techniques and/or statistical inference.

A "variant" or "genetic variant" as used herein, refers to a specific isoform of a haplotype found in a population, the specific form differing from other forms of the same haplotype in at least one, and frequently more than one, variant sites or nucleotides within the region of interest in the gene. The sequences at these variant sites that differ between different alleles of a gene are termed "gene sequence variants," "alleles," or "variants." The term "alternative form" refers to an allele that can be distinguished from other alleles by having at least one, and frequently more than one, variant sites within the gene sequence. "Variants" include isoforms having single nucleotide polymorphisms (SNPs) and deletion/insertion polymorphisms (DIPs). Reference to the presence of a variant means a particular variant, i.e., particular nucleotides at particular polymorphic sites, rather than just the presence of any variance in the gene.

"Isoform," as used herein, means a particular form of a gene, mRNA, cDNA or the protein encoded thereby, distinguished from other forms by its particular sequence and/or structure. For example, the ApoE 4 isoform of apolipoprotein E as opposed to the ApoE 2 or ApoE 3 isoforms.

The term "genotype" in the context of this invention refers to the particular allelic form of a gene, which can be defined by the particular nucleotide(s) present in a nucleic acid sequence at a particular site(s). Genotype may also indicate the pair of alleles present at one or more polymorphic loci. For diploid organisms, such as humans, two haplotypes make up a genotype. Genotyping is any process for determining a genotype of an individual, e.g., by nucleic acid amplification, DNA sequencing, antibody binding, or other chemical analysis (e.g., to determine the length). The resulting genotype may be unphased, meaning that the sequences found are not known to be derived from one parental chromosome or the other.

"Treat," "treating," or "treatment" as used herein refers to any type of measure that imparts a benefit to a patient afflicted with or at risk for developing a disease, including improvement in the condition of the patient (e.g., in one or more symptoms), delay in the onset or progression of the disease, etc. Treatment may include any drug, drug product, method, procedure, lifestyle change, or other adjustment introduced in attempt to effect a change in a particular aspect of a subject's health (i.e., directed to a particular disease, disorder, or condition).

"Drug" or "drug substance," as used herein, refers to an active ingredient, such as a chemical entity or biological entity, or combinations of chemical entities and/or biological entities, suitable to be administered to a subject to (a) delay the onset or progression of Alzheimer's disease. In accordance with the present invention, the drug or drug substance is pioglitazone or a pharmaceutically acceptable salt thereof.

The term "drug product," as used herein, is synonymous with the terms "medicine," "medicament," "therapeutic intervention," or "pharmaceutical product." Most preferably, a drug product is approved by a government agency for use in accordance with the methods of the present invention. A drug product, in accordance with the present invention, contains low dose pioglitazone.

"Disease," "disorder," and "condition" are commonly recognized in the art and designate the presence of signs and/or symptoms in an individual or patient that are generally recognized as abnormal and/or undesirable. Diseases or conditions may be diagnosed and categorized based on pathological changes. The disease or condition may be selected from the types of diseases listed in standard texts, such as Harrison's Principles of Internal Medicine, 1997, or Robbins Pathologic Basis of Disease, 1998.

"Mitochondrial dysfunction," as used herein, means any detrimental abnormalities of the mitochondria within a cell or cells. AD and stages that advance to AD are presently known in the art to be associated with mitochondrial dysfunction. This mitochondrial dysfunction causes cell damage and death by compromising ATP production, disrupting calcium homeostasis and increasing oxidative stress. Furthermore, mitochondrial damage can lead to apoptotic cell death by causing the release of cytochrome c and other pro-apoptotic factors into the cytoplasm (for review, see Wallace 1999 Science 283: 1482-1488; Schapira 2006 The Lancet 368: 70-82). Regarding a specific example found herein, and not wishing to be bound by theory, the ApoE 3 and ApoE 4 isoforms are hypothesized to cause mitochondrial dysfunction through interactions with TOMM40. Some TOMM40 variants may act synergistically with ApoE 3 isoform to accelerate mitochondrial decline. In addition, in some embodiments the ApoE 2 isoform is thought to be protective against mitochondrial dysfunction.

As used herein, the "short" TOMM40 rs10524523 allele has less than 19 thymidine (T) residues, and the "long" TOMM40 rs10524523 allele has 19 or greater T residues. In some embodiments, the long allele may indicate a higher risk of onset of late onset Alzheimer's disease within a set period of time (e.g., over a 5-7 year period).

The rs10524523 ("523") allele, an intronic polyT tract in the TOMM40 gene, is highly polymorphic with respect to length (i.e., number of T residues), and variable sizes are associated with age-of-onset distributions of late-onset AD. Measurements of the number of T residues at each of the 2 copies of the 523 polyT, 1 on each chromosome, that are carried by each individual comprise the 523 genotype and can be assessed by standard procedures, such as Sanger sequencing or electrophoretic assay.

Categorical designations of each 523 polyT are assigned according to homopolymer length: Short (S, homopolymer length less than 19 T residues), Long (L, length greater than or equal to 19, but shorter than 30) and Very Long (VL, length greater than 29 T residues). Six different 523 genotypes, using the categorical designations, are thus possible: (S,S), (VL, VL), (S,L), (VL,L), (S,VL), (L,L). See also U.S. Patent Application Publication No. 2011/0166185 to Roses, which is incorporated by reference herein.

APOE genotype is a well established risk factor for age of onset of AD. APOE ε4 alleles are strongly linked to the 523 long (L) allele and, therefore, individuals who have the 523 L,L genotype usually (e.g., 98% for Caucasian) possess the APOE ε4/ε4 genotype. However, the 523 short (S) and 523 very long (VL) alleles can be linked to either APOE ε2 or APOE ε3 alleles. APOE ε2 alleles are associated with a later age of onset of AD relative to people who carry the ε3 allele (5-8 years later, comparing APOE ε2/ε3 individuals with APOE ε3/ε3). Therefore, in some embodiments, APOE may be included in the determination in order to assign all people carrying the APOE ε2 allele to the low-risk group at the appropriate age range. The 523 genotype provides higher resolution for age of onset of cognitive impairment for individuals who carry the APOE ε3 allele in APOE (ε/3/ε3) and the APOE (ε3/ε4) genotypes.

In some embodiments, a subject with two copies of the long TOMM40 rs10524523 allele is at greater risk of developing AD as compared to a subject with one copy of the long TOMM40 rs10524523 allele, or two copies of the short TOMM40 rs10524523 allele. In some embodiments, a subject with one copy of the long TOMM40 rs10524523 allele is at greater risk of developing AD as compared to a subject with two copies of the short TOMM40 rs10524523 allele. Determination of the risk of developing AD or the onset of a stage or symptom thereof based upon TOMM40 genotype should be performed in accordance with other risk factors such as age, and may also include APOE status in some embodiments. In some embodiments, a cognitively normal subject older than 62 years of age with two copies of the very long TOMM40 rs10524523 allele is at decreased risk of developing AD relative to a subject with one or two copies of the long allele of rs10524523.

Detection of a genetic variant of TOMM40 may be performed as described in WO 2010/019550 or US 2011/0166185, each herein incorporated by reference in its entirety.

As used herein, a "subject at risk of developing Alzheimer's disease" means one who is predisposed to Alzheimer's disease, has genetic susceptibility for Alzheimer's disease and/or is more likely to develop Alzheimer's disease at a predetermined age than subjects in which the genetic risk factor is absent.

As used herein, "increased risk" means likely to develop AD within a short time, e.g., 5-7 years from a time point of, for example, the initiation of treatment according to some embodiments described herein, or the time of determination of a predisposition to or symptom of Alzheimer's disease (for example by analysis of any one of brain atrophy, decreased synaptic activity in the brain, increased amyloid accumulation in the brain, decreased mitochondrial function in the brain, decreased proliferation in the brain, diseased neurons, the formation of neurofibrillar tangles in the brain, amyloid in the CSF and Tau and/or phospho-Tau in the CSF).

"Increased risk" may also mean an individual is likely to develop AD at a younger age than a control subject, that is that an individual with at least one copy of the long rs10524523 allele is at greater risk of developing AD at an earlier age than an individual with no copies of the long rs10524523 allele according to some embodiments.

Figure 2:
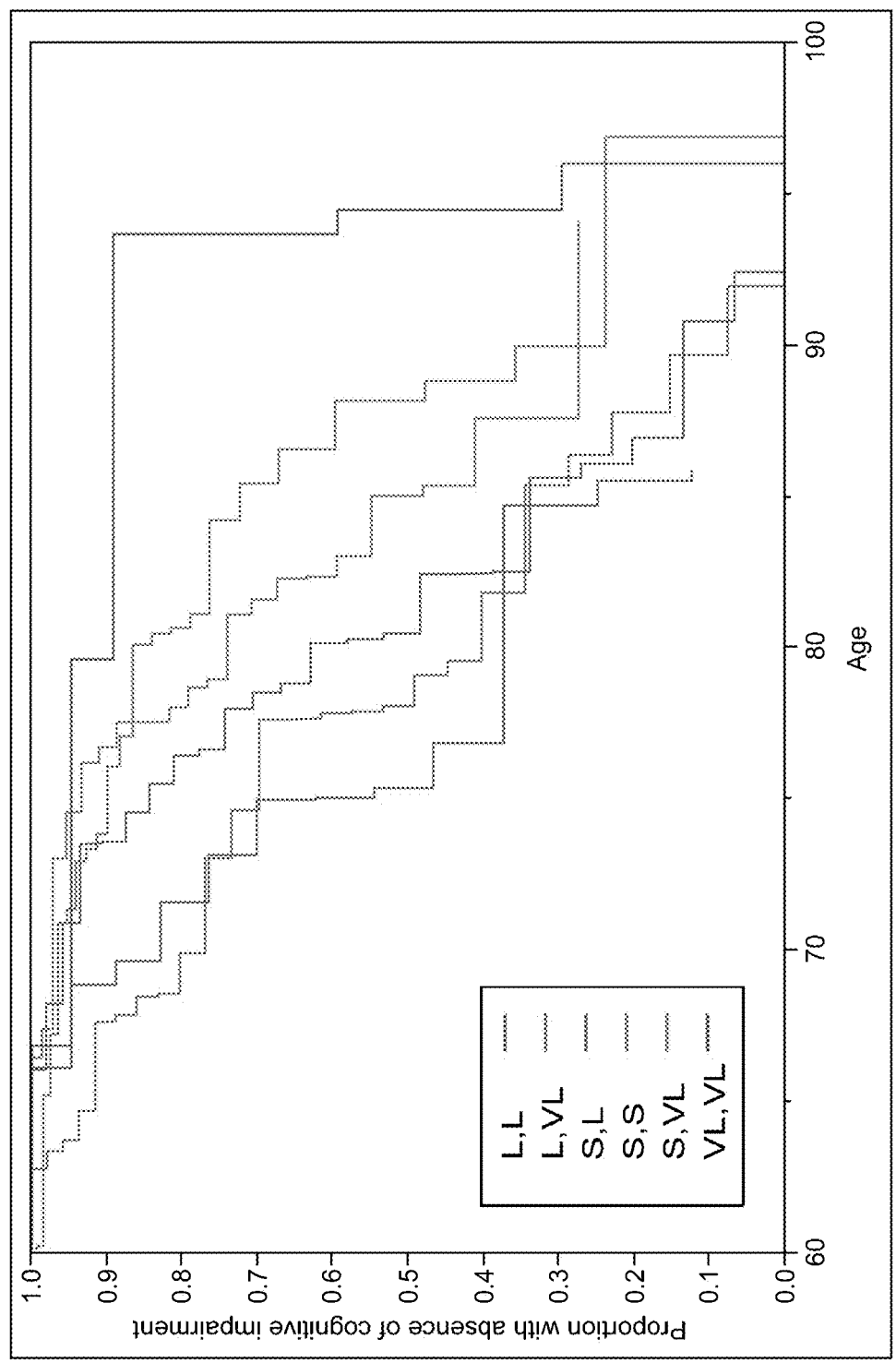
FIG. 2 presents a graph of the age at onset of cognitive impairment of the Alzheimer type for each of the TOMM40 523 genotypes. The Y axis shows the percent survival without cognitive impairment, while the X axis represents age. Data obtained from the Duke Bryan ADRC cohort N=438 subjects, 106 diagnosed with cognitive impairment, 332 cognitively normal. N for each genotype: L,L:23; L,VL: 54; S,L:72; S,S:100; S,VL:138; VL,VL:51.

The age at which a subject is deemed to be at increased risk of developing AD may be determined by graphing one or more factors (e.g., TOMM40 523 genotype) against age and determining the point at which the risk changes are largest related to a change in age (see FIG. 2). This point may be "about" a particular age, meaning that the age may vary by 0.5, 1, 2, 3, 4 or 5 years from that point, which variation may result from, e.g., further optimization or higher data resolution of the graphs upon receipt of additional data.

A method of "administration" useful according to the invention includes, but is not limited to, administration by, for example, ingestion via the oral route, intranasal, rectal, inhalation, topical or injection, such as intravenous, subcutaneous, intramuscular, intraperitoneal, intracranial and spinal injection. Additional methods of administration are provided herein below in the section entitled "Dosage and Administration."

As used herein, "diagnosing" or "identifying a patient or subject having Alzheimer's disease" refers to a process of determining if an individual is afflicted with Alzheimer's disease or a stage that progresses to Alzheimer's disease, as defined herein. A diagnosis of Alzheimer's disease may be based on, for example, National Institute of Neurological and Communicative Disorders and Stroke-Alzheimer's Disease and Related Disorders Association criteria.

"Low dose pioglitazone" refers to pioglitazone or a pharmaceutically acceptable salt thereof in an amount in the range of from 0.5 mg to 12 mg, such as 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9 mg, 9.25 mg, 9.5 mg, 9.75 mg, 10 mg, 10.25 mg, 10.5 mg, 10.75 mg, 11 mg, 11.25 mg, 11.5 mg, 11.75 mg or 12 mg. Alternatively, in some embodiments of the present invention, low dose pioglitazone means a low dose amount of pioglitazone or a pharmaceutically acceptable salt thereof that provides a pioglitazone AUC in a subject in a range of from about 0.15 μg·h/mL to about 3.6 μg·h/mL (±25%). For example, low dose pioglitazone AUC may be in a range of from 0.12, 0.37, or 1.12 to 3.4 or 4.5 μg·h/mL.

As used herein, "control subject" means a subject that has not been diagnosed with Alzheimer's disease and/or does not exhibit any detectable symptoms associated with Alzheimer's disease. A "control subject" also means a subject that is not at risk of developing Alzheimer's disease, as defined herein.

As used herein, a "subject that is not at risk of developing Alzheimer's disease" means, for example, a subject that does not have a TOMM40 rs10524523 genotype that indicates, together with age and possibly other factors such as APOE status, that the subject is not more likely than the general population or a stratified portion thereof to develop AD or a stage or symptom thereof.

As used herein, the term "pharmaceutically acceptable salt" refers to those salts which are, within the scope of sound medical judgment, suitable for use with pioglitazone when in contact with the tissues of subjects, e.g., animals, including mammals, humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts which are salts of an amino group formed with inorganic acids, such as hydrochloric acid, hydrobromic acid, phosphoric acid, sulfuric acid and perchloric acid, or with organic acids, such as acetic acid, maleic acid, tartaric acid, citric acid, succinic acid or malonic acid, or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

II. Alzheimer'S Disease

Symptoms of Alzheimer's Disease

Common symptoms of Alzheimer's disease include, but are not limited to, memory loss, difficulty performing familiar tasks, problems with language, disorientation to time and place, poor or decreased judgment, problems with abstract thinking, misplacing things, change in mood or behavior, changes in personality and loss of initiative. These symptoms appear gradually over time and usually (but not always) begin with episodic memory problems, followed by other cognitive deficits that adversely affect a person's normal functioning (i.e., activities of daily living). Behavioral/personality changes usually occur later in the disease process, as a person becomes more moderately and severely affected. Some examples of these characteristic symptoms are described below.

Memory Loss

This includes forgetting recently learned information and is one of the most common early signs of dementia. A person begins to forget more often and is unable to recall the information later. This includes forgetting names or appointments occasionally.

Difficulty Performing Familiar Tasks

People with dementia often find it hard to plan or complete everyday tasks. Individuals may lose track of the steps involved in preparing a meal, placing a telephone call or playing a game. This includes occasionally forgetting why you came into a room or what you planned to say.

Problems with Language

People with Alzheimer's disease often forget simple words or substitute unusual words, making their speech or writing hard to understand. They may be unable to find the toothbrush, for example, and instead ask for "the thing for my mouth." This includes forgetting names or appointments occasionally.

Disorientation to Time and Place

People with Alzheimer's disease can become lost in their own neighborhood, forget where they are and how they got there, and not know how to get home. This includes forgetting the day of the week or where you were going. In some patients, confusion and sometimes accompanying agitation and behavioral issues manifest more in the late afternoon or early evening, a symptom referred to as "sundowning."

Poor or Decreased Judgment

Those with Alzheimer's may dress inappropriately, wearing several layers on a warm day or little clothing in the cold. They may show poor judgment, like giving away large sums of money to telemarketers. This includes making a questionable or debatable decision from time to time.

Problems with Abstract Thinking

Someone with Alzheimer's disease may have unusual difficulty performing complex mental tasks, like forgetting what numbers are for and how they should be used. This includes finding it challenging to balance a checkbook.

Misplacing Things

A person with Alzheimer's disease may put things in unusual places: an iron in the freezer a wristwatch in the sugar bowl. This includes misplacing keys or wallet temporarily.

Change in Mood or Behavior

Someone with Alzheimer's disease may show rapid mood swings—from calm to tears to anger—for no apparent reason. This includes occasionally feeling sad or moody.

Changes in Personality

Personalities of people with dementia can change dramatically. They may become extremely confused, suspicious, fearful or dependent on a family member. People's personalities do change somewhat with age.

Loss of Initiative

A person with Alzheimer's disease may become very passive, sitting in front of the TV for hours, sleeping more than usual or not wanting to do usual activities. This includes feeling weary of work or social obligations.

Diagnosis and Staging of Alzheimer's Disease

The clinical diagnosis of Alzheimer's disease is a process that typically involves a variety of steps (including medical history, physical and mental status examinations, and laboratory tests) and tools. Of the latter, since 1984, the diagnostic criteria established by the National Institute of Neurological Disorders and Stroke (NINDS)/Alzheimer's Disease and related Disorders Association (ADRDA) have been, along with the DSM-IV criteria, the primary standards used in clinical practice and research. Both require the presence of memory dysfunction and cognitive impairment, although while the DSM criteria stipulate that the latter adversely affects normal functioning, the NINCDS/ADRDA criteria do not. A feature of both sets of criteria is that they do not consider an antemortem diagnosis of AD as definitive, since until recently there was no methodology to assess brain pathology for characteristic AD features until after a patient's death. The NINCDS/ADRDA criteria therefore considered the antemortem diagnosis to be either "possible" or "probable", depending on the strength of the clinical evidence, including the ruling out of multiple differential diagnoses.

Until recently, the deterioration of a subject to Alzheimer's disease has been characterized by multiple clinical stages. The term "stage" is used herein in a general sense to describe how a subject's abilities change from normal function, e.g., normal cognitive state, to Alzheimer's disease. It should be noted that stages are general guides, symptoms can vary greatly in and/or between the stages, and that not every subject will experience the same symptoms in a given stage or progress to Alzheimer's disease at the same rate. For example, a seven-stage framework was developed by Barry Reisberg, M.D., clinical director of the New York University School of Medicine's Silberstein Aging and Dementia Research Center, which includes: Stage 1: No impairment; Stage 2: Very mild decline; Stage 3: Mild decline; Stage 4: Moderate decline; Stage 5: Moderately severe decline; Stage 6: Severe decline; and Stage 7: Very severe decline. In the clinical research arena, AD has been often defined somewhat loosely as "mild", "moderate", or "severe" based on scores from psychometric instruments such as the Mini-Mental State Examination, where, for example, mild AD could be considered 18-26, moderate 11-17, and severe anything 10 or below (on a 30-point scale where higher scores indicate greater cognitive function).

In 2007, Dubois et al proposed that the NINCDS/ADRDA criteria for AD diagnosis be revised to incorporate learnings from the growth in the field's understanding of the disease process and the development of new methods to assess antemortem biomarkers of AD, including brain imaging (Dubois et al. 2007 Lancet Neurol 6: 734-746). In this proposal, even with the presence of supportive features, the antemortem diagnosis is still considered "probable" AD, while a "definite" AD diagnosis was reserved for histopathological confirmation or genetic evidence (mutation on chromosome 1, 14, or 21).

In 2011, a workgroup representing the National Institute on Aging/Alzheimer's Association Research Roundtable proposed similar revisions to the NINCDS/ADRDA criteria and proposed criteria to establish a diagnosis of MCI and MCI due to AD (Albert et al. 2011 Alzheimers Dement 7: 270-279; McKhann et al. 2011 Alzheimers Dement 7: 263-269). This workgroup updated criteria for all cause dementia and dementia due to AD. The workgroup retained the designations of probable AD dementia, possible AD dementia, and probable or possible AD dementia with evidence of the AD pathophysiological process. The first two designations were intended for use in all clinical settings, whereas the last designation was determined to be appropriate for research purposes. The workgroup recognized that the Alzheimer's disease progression is a continuum and that distinguishing between MCI and dementia is a clinical assessment of whether there is significant interference with daily activities.

"Preclinical AD" refers to a stage at which symptoms are sufficient to meet the currently accepted criteria of Preclinical AD (see Dubois et al., supra). Generally speaking, preclinical AD is the long, presymptomatic phase during which time the pathophysiological processes of AD are beginning. There may be very subtle cognitive symptoms years before subjects meet the clinical criteria of MCI (Sperling et al. 2011 Alzheimers Dement 7: 280-292).

"Prodromal AD" refers to a stage at which symptoms meet the currently accepted criteria of Prodromal AD (see Dubois et al. supra.). In accordance with the present invention, prodromal AD is a symptomatic predementia stage that generally includes MCI but not dementia, and is characterized by symptoms not yet severe enough to meet full Alzheimer's disease diagnostic criteria. The Prodromal AD stage is also referred to herein as the progressive MCI stage.

III. Pioglitazone

Pioglitazone is a thiazolidinedione agent having the following chemical structure:

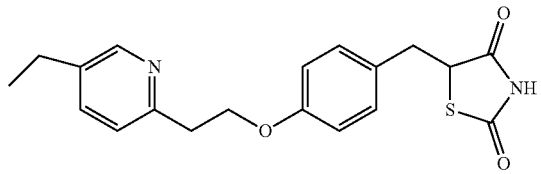 [SMILES: CCc1ccc(CCOc2ccc(CC3SC(=O)NC3=O)cc2)nc1]

Pioglitazone HCl is a potent agonist for peroxisome proliferator-activated receptor gamma (PPARγ). PPAR receptors are found in tissues such as adipose tissue, skeletal muscle and liver.

While not wishing to be bound by theory, it is thought that the PPARγ agonist pioglitazone protects against or ameliorates at least some of the pathological mechanisms involved in Alzheimer's disease (AD), such as the decrease in metabolic activity seen in the preclinical stage.

The pathophysiological changes corresponding to the clinical manifestation of AD may begin years, or even decades, before the first cognitive symptoms appear, developing slowly over a preclinical phase. In some embodiments, administration of low dose pioglitazone as taught herein may protect against or ameliorate these changes, leading to a delay in the onset cognitive impairment of the Alzheimer's type.

In some embodiments, pioglitazone is administered in an amount effective to protect or increase neuronal mitochondrial function, or to expand the mitochondrial reservoir, for treating, such as delaying or preventing, cognitive impairment (e.g., cognitive impairment of the Alzheimer's type). In some embodiments, treatment is initiated before significant pathological damage has accrued and/or cognitive impairment is detected or diagnosed.

Mitochondrial dysfunction is thought to play a significant role in the cerebral hypometabolism observed in AD. Brain metabolic activity, primarily due to mitochondrial activity, decreases and non-pathological brain atrophy occurs during healthy aging (Curiati et al. 2011 Am J Neuroradiol 32: 560-565), but metabolic decline and atrophy occur at a significantly higher rate in prodromal and symptomatic early onset (Familial) AD, in mild cognitive impairment (MCI), and in late onset Alzheimer's disease (Reiman et al. 1996 N Engl J Med 334: 752-758; Mosconi et al. 2004 Psychiatry Research: Neuroimaging 130: 141-151; Mosconi et al. 2005 J Neurol Neurosurg Psychiatry 76: 15-23; Mosconi et al. 2006 J Nucl Med 47: 1778-1786; Chételat et al. 2008 Brain 131: 60-71; Mosconi et al. 2008 Annals of the New York Academy of Sciences 1147: 180-195; Mosconi et al. 2009 Neurology 72: 513-520; Mosconi et al. 2009 Eur J Nucl Med Mol Imaging 36: 811-822; Villain et al. 2010 Brain 133: 3301-3314). Mitochondrial enzyme activity has also been found to be reduced in autopsied hippocampus of AD patients, and in platelets and fibroblasts, relative to cognitively normal subjects (Mancuso et al. 2010 Adv Exp Med Biol 685: 34-44).

The hypothesis that perturbation of mitochondrial function is a very early event in AD etiology, occurring possibly decades ahead of clinical symptoms, is well-supported (Castellani et al. 2002 Journal of Neuroscience Research 70: 357-360; Bubber et al. 2005 Annals of Neurology 57: 695-703; Beal 2007 Mitochondrial Biology: New Perspectives 287: 183-192; discussion 192-186; Liang et al. 2008 Physiological Genomics 33: 240-256; Liang et al. 2008 PNAS 105: 4441-4446; Jack et al. 2009 Brain 132: 1355-1365; Moreira et al. 2010 Biochimica et Biophysica Acta (BBA)—Molecular Basis of Disease 1802: 2-10; Swerdlow et al. 2010 J Alzheimers Dis 20 Suppl 2: S265-279; Cunnane et al. 2011 Nutrition 27: 3-20). There are changes in expression, in multiple brain regions, of genes involved in mitochondrial function in young individuals who are at increased risk of developing AD due to carriage of APOEϵ4 (Conejero-Goldberg et al. 2011 Molecular Psychiatry 16: 836-847), and relatively decreased metabolic activity has been measured, biochemically, following death and with imaging techniques during life, in brains of cognitively normal people who are determined to be at increased risk of developing late onset AD because of family history of the disease or carriage of at least one APOEϵ4 allele (Small et al. 1995 JAMA 273: 942-947; Reiman et al. 2005 PNAS 102: 8299-8302; Mosconi et al. 2008 Annals of the New York Academy of Sciences 1147: 180-195; Langbaum et al. 2010 Arch Neurol 67: 462-468; Mosconi et al. 2011 Journal of Alzheimer's Disease).

The human brain consumes more energy per gram of tissue than any other organ, accounting for approximately a fifth of the body's total energy expenditures. Glucose is the primary fuel for brain metabolism, with the majority of cellular energy production occurring in mitochondria. Neuronal mitochondria generate adenosine triphosphate (ATP) to power neurotransmitter release and uptake at synapses, to maintain ion gradients, to power mitochondrial and axonal transport. Mitochondria also regulate calcium homeostasis and apoptosis, while dysfunctional mitochondria produce increased levels of toxic reactive oxygen species (Mattson et al. 2008 Neuron 60: 748-766). Some studies suggest that neurons also utilize lactate produced by the oxidation of glucose in adjacent astrocytes (Pancani et al. 2011 Cell Calcium 50: 548-558). Lactate is ultimately reduced to pyruvate in neurons and then, like glucose, feeds into the oxidative phosphorylation pathway in mitochondria to produce ATP.

In some embodiments, changes in brain metabolic activity upon administering may be measured to determine the optimal dosages and/or forms of administration for pioglitazone. Brain metabolic activity may be measured using specialized techniques known in the art, including functional Magnetic Resonance Imaging (fMRI), the most common implementation being Blood Oxygen Level Dependent (BOLD) fMRI, and [$^{18}$F]-fluorodeoxyglucose-Positron Emission Tomography (FDG-PET) (Jack et al. 2000 Neurology 55: 484-490; Whitwell et al. 2007 Brain 130: 1777-1786). BOLD fMRI measures the ratio of deoxyhemoglobin to oxyhemoglobin; small increases in regional neural activity result in increased regional demand for oxygen delivery via the cerebral vasculature, resulting in an increased fMRI signal in the area. Thus, BOLD provides an indirect, but sensitive, measure of neural activity. A quantitative measure of glucose uptake, the cerebral metabolic rate of glucose (CMRglu), may be calculated with FDG-PET.

Cunnane et al., reviewing a substantial body of literature on FDG-PET studies of MCI and AD, concluded that the global cerebral metabolic rate of glucose (CMRg) is reduced by approximately 20-25% in AD patients after correction for brain atrophy (Cunnane et al., supra). The most consistent FDG-PET findings in AD are reduced CMRglu in entorhinal cortex and hippocampus—two regions that are earliest affected by AD—progressing to posterior cingulate cortex, temporoparietal areas, precuneus and prefrontal cortex as the disease advances (During et al. 2011 Neurological Sciences 32: 559-569; Filippi and Agosta 2011 Journal of Alzheimers Disease 24: 455-474). Reduced cerebral glucose metabolism may also be apparent before a diagnosis of AD, at very early stages of cognitive decline, as well as in AD-sensitive brain regions in MCI, with the magnitude and extent of hypometabolism worsening as cognition declines (Caselli et al. 2008 Arch Neurol 65: 1231-1236; Nishi et al. 2010 J Neuroimaging 20: 29-36; Chetelat et al. 2008, supra).

A longitudinal study demonstrated that, for people who progressed from normal cognition to a clinical diagnosis of amnestic MCI, there was a correlation between decline in cognition and reduction in metabolism in brain regions known to be preferentially affected by AD. This decline in the AD-sensitive regions of the brain was not evidenced in a similar group of people who maintained stable cognition over the study (Caselli et al. 2008, supra; Chetelat et al. 2008, supra). In addition, young adult and middle-age individuals who are cognitively normal but at risk for AD (e.g., with family history of AD, a carrier of APOEϵ4, or individuals with presymptomatic early-onset, familial AD), have reduced glucose metabolism in brain regions sensitive to AD pathology relative to those without these risk factors (Small, et al. 1995, supra; Reiman et al. 1996, supra; Reiman et al. 2005, supra; Mosconi et al. 2006, supra; Langbaum et al. 2010, supra; Small et al. 2000 PNAS 97: 6037-6042; Reiman et al. 2004 PNAS 101: 284-289). Thus, reduced metabolism in regions of the brain affected by AD may be one of the earliest pathophysiological changes and/or indicators of future disease in those at risk of developing the disease, and may also be correlated with disease progression.

As known in the art, fMRI, using Blood Oxygen Level dependent (BOLD) contrast, can be used to visualize and measure neuronal activity during tasks, e.g., cognitive tasks, and to visualize the resting state activity of the brain, including the default mode network (DMN), which is a network of brain regions that is active during the awake resting state but deactivated during a task (Pihlajamäki and Sperling 2008 Future Neurology 3: 409-421; Huettel and Larry 2009 Encyclopedia of Neuroscience 273-281). Neuronal activity increases metabolism and regional demand for glucose and oxygen, which stimulates blood flow to the active regions of the brain. This is the hemodynamic response (the product of local cerebral blood flow, the cerebral metabolic rate of oxygen and cerebral blood volume) that is visualized by BOLD fMRI is a widely accepted indicator of neuronal activity and reflects energy consumption (Pihlajamäki and Sperling 2008, supra; Wise and Preston 2010 Drug Discovery Today 15: 973-980; Reitz et al. 2011 Nat Rev Neurol 7: 137-152).

BOLD fMRI reveals that task-evoked brain activity is compromised in those at risk of AD, and further diminishes as AD progresses (Filippi and Agosta 2011, supra). Some of the tasks used may challenge the higher order cognitive functions that are compromised early in the disease process, including episodic and working memory. The BOLD fMRI signal changes earliest in the medialtemporal lobe (MTL), including the hippocampus, and connected neural networks that are required for encoding or retrieving memories (Pihlajamäki and Sperling 2008, supra). Reduced neural activity is also evident in the MTL, particularly in regions of the hippocampus, of young and old cognitively normal individuals who are at increased risk of developing AD (Pihlajamäki and Sperling 2008, supra; Filippi and Agosta 2011, supra; Wu et al. 2009 J Cell Physiol 220: 58-71; Jones et al. 2011 Neurology 77: 1524-1531), and the magnitude of the BOLD fMRI signal in the posteromedial cortical region is associated with verbal episodic memory performance in cognitively normal older subjects, and is decreased as subjects progress from cognitive impairment to AD dementia (Pihlajamaki et al. 2010 Alzheimer Disease & Associated Disorders 24: 28-36). In addition to changes in task-evoked brain activity in preclinical, prodromal and AD dementia, fMRI and FDG-PET studies of the brain in its resting state indicate that the functional connectivity between specific regions of the brain are increasingly altered as MCI and AD progress (Reiman et al. 1996, supra; Filippi and Agosta 2011, supra; Jin et al. 2012 Magnetic Resonance Imaging 30: 48-61). BOLD-fMRI has proven to be a particularly useful method for measuring functional connectivity in human brain and in brains of other species, e.g., the rat. Biswal et al. recognized as early as 1995 that there was temporal correlation of low frequency fluctuations of blood flow and oxygenation, measured by fMRI, in regions of the brain that were functionally related (Biswal et al. 1995 Magn Reson Med 34: 537-541). These spatio-temporally coordinated fluctuations occur even when the brain is not engaged in a task, i.e., when the brain is at rest, and are thought to reflect spontaneous neuronal activity or background brain processes (Damoiseaux et al. 2011 Neurobiology of Aging; Yamasaki et al. 2012 Neurology Research International 2012). In AD, altered functional connectivity has been noted between brain regions or systems required for higher-order cognitive processes, including in the DMN and the systems involved in attention (Yamasaki et al. 2012, supra). Decreased resting connectivity in the DMN in specific brain regions—e.g., between the posterior cingulate cortex and temporal cortex or hippocampus and between the subcortical region, the thalamus, and a number of cortical regions—has been reported for AD and MCI patients (Wang et al. 2011 European Journal of Radiology). By contrast, there is increased resting state functional connectivity in frontal regions and between regions of the DMN and frontal parts of the brain in AD and MCI (Wang et al. 2006 NeuroImage 31: 496-504; Zhang et al. 2009 Behav Brain Res 197: 103-108).

Heretofore the ability to predict which people are more likely to develop these pathophysiological changes, which may lead to cognitive impairment, and ultimately Alzheimer's dementia, has not been feasible. The TOMM40 rs10524523 genotype along with age and possibly other factors are useful as a prognostic biomarker to determine which subjects are at risk for developing cognitive impairment of the Alzheimer's type and provide the opportunity to intervene in the early phase of this progressive and devastating disease.

PPARγ is a ligand-activated, nuclear transcription factor that impinges on many pathways implicated in the etiology of AD (Landreth et al. 2008 Neurotherapeutics 5: 481-489). Its biological actions include the modulation of inflammatory gene expression and the regulation of glucose and lipid metabolism, both of which are abnormal in AD. PPARγ also has direct effects on mitochondrial function and ATP production. Many thought leaders in AD research believe that mitochondrial dysfunction plays a significant role in the cerebral hypometabolism observed in AD.

The PPARγ receptor is activated by endogenous ligands and by a number of pharmacological agents including drugs of the thiazolidinedione (TZD) class.

Pioglitazone is marketed for the treatment of type 2 diabetes (Actos™), and treats the insulin resistance that is the hallmark by type 2 diabetes by increasing the sensitivity of tissues, particularly the liver, muscle and adipose tissue, to the effects of insulin (Olefsky 2000 The Journal of Clinical Investigation 106: 467-472). T2DM and insulin resistance are risk factors for developing AD, and diabetic patients carrying APOEε4 are at particular risk (Irie et al. 2008 Arch Neurol 65: 89-93; Rönnemaa et al. 2008 Neurology 71: 1065-1071; Bruehl et al. 2009 Journal of Clinical and Experimental Neuropsychology 32: 487-493). Brains from autopsied AD patients have markedly lower levels of insulin, insulin receptor and IRS-1 mRNA than control brains, consistent with an insulin resistance or diabetic phenotype leading some to characterize AD as type 3 diabetes (Steen et al. 2005 J Alzheimers Dis 7: 63-80. Insulin receptors are found throughout the human brain, and are at particularly high concentrations in the hypothalamus, cerebellum, and cortex, and PPARγ and its coactivator, retinoid X receptor (RXR), are also expressed in the brain, including in the hippocampus and cortex (Inestrosa et al. 2005 Experimental Cell Research 304: 91-104; Gofflot et al. 2007 Cell 131: 405-418; Morales-Garcia et al. 2011 GLIA 59: 293-307). PPARγ receptor is expressed in astrocytes and neurons, and the level of the protein is reduced by ~40% in postmortem brain lysates from AD patients.

Pioglitazone improves neuronal insulin resistance (Liu et al. 2010 European Journal of Pharmacology 629: 153-158), and concentrations as low as 1 nM significantly reduce cell death due to glucose deprivation, possibly because pioglitazone affords protection from hypoglycemia by increasing mitochondrial content and/or modulating mitochondrial structure. The drug also increases expression of NRF1, TFAM1 (transcription factors required for mitochondrial biogenesis), and UCP-2 (required for mitochondrial remodeling) (Miglio et al. 2009 Neurochemistry International 55: 496-504).

Beneficial effects of pioglitazone have been reported in transgenic mouse models of AD, and mouse and rat models of neurodegeneration or brain injury. The reported beneficial effects upon treatment with pioglitazone include the reduction of brain amyloid plaque burden in transgenic mouse models of AD, improved brain glucose utilization and cerebrovascular function, reduced brain inflammation, decreased oxidative stress, improvement of pathology-related memory and learning deficits, and increased neurogenesis in adult animals (Heneka et al. 2000 Journal of Neuroscience 20: 6862-6867; Yan et al. 2003 Journal of Neuroscience 23: 7504-7509; Heneka et al. 2005 Brain 128: 1442-1453; Pathan et al. 2006 Life Sci 79: 2209-2216; Nicolakakis et al. 2008 Journal of Neuroscience 28: 9287-9296; Kaur et al. 2009 Fundamental & Clinical Pharmacology 23: 557-566; Roberts et al. 2009 Experimental Neurology 216: 459-470; Glatz et al. 2010 Journal of Hypertension 28: 1488-1497; Nicolakakis and Hamel 2011 J Cereb Blood Flow Metab 31: 1354-1370; Morales-Garcia et al. 2011, supra; Zhang, Xu et al. 2011, supra). Pioglitazone also improved cognition and hyperinsulinemia, and improved regional cerebral blood flow in small placebo-controlled clinical trials of diabetic patients with AD or mild cognitive impairment (Hanyu et al. 2009 Journal of the American Geriatrics Society 57: 177-179; Hanyu et al. 2010 J Am Geriatr Soc 58: 1000-1001; Sato et al. 2010 Neurobiology of Aging 32: 1626-1633).

The marketed 15 mg, 30 mg and 45 mg dosage of pioglitazone is appropriate for dosing for type 2 diabetes and is safe and efficacious for the treatment of this disease. Diabetes-level doses of pioglitazone have been used in small clinical studies of Alzheimer's disease (Hanyu et al. 2009 Journal of the American Geriatrics Society 57: 177-179; Hanyu et al. 2010 J Am Geriatr Soc 58: 1000-1001; Sato et al. 2010 Neurobiology of Aging 32: 1626-1633). In addition, in a recent clinical trial for Alzheimer's treatment using a different thiazolidinedione—rosiglitazone—the type 2 diabetes dosage of the drug was used (Risner et al. 2006 Pharmacogenomics Journal 6: 246-254; Gold et al. 2010 Dementia and Geriatric Cognitive Disorders 30: 131-146).

However, it would be preferred to limit exposure to drug if the required pharmacodynamic effect and efficacy may be sufficiently achieved at a lower dose for the intended patient population. In this manner, the frequency of rare or uncommon adverse events may be further reduced, thereby improving the safety.

As taught herein, and as demonstrated by the BOLD study results presented in the Examples below, it has been surprisingly found that dosages significantly lower than those used for the treatment of type II diabetes (i.e., low dose pioglitazone) result in a change in brain metabolism and thus may be effective in the treatment of Alzheimer's disease, including the delay of onset of cognitive decline (e.g., cognitive impairment of the Alzheimer type).

V. Formulations and Modes of Administration

The invention provides for a number of drug product formulations of low dose pioglitazone useful according to the methods of the present invention, including but not limited to a low strength (LS) formulation, an orally disintegrating tablet (ODT) formulation, a liquid formulation, a suspension formulation, a nasal formulation, an orally immediate, modified, controlled or extended release formulation, a transdermal formulation a rectal formulation, a topical formulation or an injectable formulation.

(a) Low Strength (LS) Formulation

The invention provides for LS formulations of low dose pioglitazone, for example as described in U.S. Ser. No. 12/452,587 and U.S. Patent Publication No. 2010/0166853, herein incorporated by reference in its entirety). The coated preparation of the present invention comprises a core comprising a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5, and a coating layer comprising pioglitazone or a salt thereof.

The coated preparation of the present invention may be a single preparation having a core and a coating layer, or a collection of preparations each having a core and a coating layer. In addition, the coated preparation of the present invention may be a capsule produced by mixing a collection of preparations each having a core and a coating layer with additives as necessary and filling a capsule with the mixture.

Furthermore, the coated preparation of the present invention may be a tablet or caplet produced by mixing a collection of preparations each having a core and a coating layer with additives and compression-molding the mixture.

The core of the coated preparation of the present invention may consist only of a pharmaceutically acceptable organic acid with water solubility at 20° C. of not less than 10 mg/mL and $pK_{a1}$ at 25° C. of not more than 5. Alternatively, it may consist of a composition of a pharmaceutically acceptable organic acid with water solubility at 20° C. of not less than 10 mg/mL and $pK_{a1}$ at 25° C. of not more than 5 and, for example, the below-mentioned additive and the like.

The organic acid contained in the core of the coated preparation of the present invention is a pharmaceutically acceptable organic acid with water solubility at 20° C. of not less than 10 mg/mL and $pK_{a1}$ at 25° C. of not more than 5. The water solubility at 20° C. is preferably not less than 50 mg/mL, more preferably not less than 100 mg/mL. The water solubility at 20° C. is preferably not more than 2000 mg/mL. $pK_{a1}$ at 25° C. is preferably not more than 5, more preferably not more than 4. The $pK_{a1}$ is preferably not less than 1. Preferred is an organic acid with water solubility at 20° C. of not less than 300 mg/mL and $pK_{a1}$ at 25° C. of not more than 4.

Specific examples of organic acid include one or more of citric acid, tartaric acid, malic acid and ascorbic acid, and the like. The organic acid may be any of hydrate and acidic salt. In addition, the organic acid is preferably in the form of a crystal, since the mechanical strength and chemical stability of the core containing the crystalline organic acid are not degraded during the production step of the preparation of the present invention, and in view of the acidity.

In the present specification, citric acid includes citric acid monohydrate and anhydrous citric acid.

As the organic acid, citric acid, tartaric acid and malic acid are preferable, and citric acid (particularly anhydrous citric acid) is more preferable as a pharmaceutical additive.

The average particle size of the organic acid is generally 100-1500 μm, preferably 300-800 μm. The average particle size is measured, for example, using a laser diffraction particle distribution measurement apparatus (e.g., SYNPATEC HELOS-RODOS particle distribution measurement apparatus).

While the average particle size of the core varies depending on the kind of coated preparation of the present invention, it is generally 100-1500 μm, preferably 300-800 μm.

The core of the coated preparation of the present invention can be covered with a coating layer comprising pioglitazone or a salt thereof.

While the content of the organic acid in the core of the coated preparation of the present invention varies depending on the kind of organic acid and the like, it is generally 20-95 parts by weight, preferably 40-80 parts by weight, per 100 parts by weight of the coated preparation.

With regard to pioglitazone or a salt thereof used for the coated preparation of the present invention, examples of the salt of pioglitazone include pharmacologically acceptable salts such as salts with inorganic acid, salts with organic acid, salts with acidic amino acid and the like.

Preferable examples of the salts with inorganic acid include salts with hydrochloric acid, hydrobromic acid, nitric acid, sulfuric acid, phosphoric acid and the like.

Preferable examples of the salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with acidic amino acid include salts with aspartic acid, glutamic acid and the like.

In addition, pioglitazone may be any of anhydride or hydrates, and the pioglitazone may be further labeled with an isotope (e.g., $^3H$, $^{14}C$, $^{35}S$, $^{125}I$) and the like.

Pioglitazone or a pharmaceutically acceptable salt thereof is preferably pioglitazone hydrochloride.

Pioglitazone or a pharmaceutically acceptable salt thereof may be diluted with a diluent and the like that are generally known in the art.

In the coated preparation of the present invention, the median particle size of pioglitazone and a salt thereof to be used as a starting material is preferably 0.5 to 50 μm.

By adopting such a median size, a coated preparation of pioglitazone or a pharmaceutically acceptable salt thereof, which has superior dissolution, can be obtained.

The above-mentioned preferable median size is applied to pioglitazone or a pharmaceutically acceptable salt thereof used as the starting material. The starting material may comprise a pulverized product obtained by pulverization during the process of producing coated preparation, or a mixed pulverized product obtained by pulverization together with an excipient (e.g., crystalline cellulose) or the like. The median size of pioglitazone or a pharmaceutically acceptable salt thereof may change beyond the above range during a production process of the coated preparation of the present invention, or a preservation process of the coated preparation after production, by coagulation of pioglitazone or salt thereof. The pulverization is performed using a preparation forming machine such as a mortar, a jet mill, a hammer mill, a screen mill (P-3; Showa Kagaku Kikai Kosakusho Co., Ltd.) or the like.

As used herein, the median size means a particle size that divides into crude particles and fine particles by 50% based on the weight distribution or number distribution. The median size can be measured, for example, by laser diffraction particle size distribution measurement apparatus (e.g., SYNPATEC HELOS-RODOS particle distribution measurement apparatus).

The dispersibility of pioglitazone or a pharmaceutically acceptable salt thereof having the above-mentioned desired median size is preferably as defined by particles of not more than 0.1 μm are contained at not more than 10% of the total amount, and particles of not less than 1000 μm are contained at not more than 10% of the total amount. The lower limit thereof is generally as defined by particles of not more than 0.1 μm are contained at not less than 0.1% of the total amount, and particles of not less than 1000 μm are contained at not less than 0.1% of the total amount.

While the content of pioglitazone or a pharmaceutically acceptable salt thereof in the coated preparation of the present invention varies depending on the dosage form, dose and the like of the coated preparation, it is generally 0.01-30 parts by weight, preferably 0.5-25 parts by weight, further preferably 0.5-20 parts by weight, per 100 parts by weight of the coated preparation.

In the coated preparation of the present invention, a weight ratio of pioglitazone and the aforementioned pharmaceutically acceptable organic acid is preferably 1:4-1:100, more preferably 1:4-1:20, more preferably 1:5-1:10. The weight of the pioglitazone means pioglitazone equivalent in a pharmaceutically acceptable salt of pioglitazone.

In the coated preparation of the present invention, the amount of the coating layer comprising pioglitazone or a salt thereof to be used is generally 5-205 parts by weight, preferably 10-100 parts by weight, more preferably 20-90 parts by weight, per 100 parts by weight of the core.

The coated preparation of the present invention preferably contains cellulose or a cellulose derivative in a coating layer. Of these, a cellulose derivative is preferable.

The cellulose derivative is a cellulose wherein a part of the cellulose molecule is substituted by other atoms or functional groups. Examples of the cellulose derivative include low-substituted hydroxypropylcellulose (L-HPC), hydroxypropylmethylcellulose, methylcellulose, hydroxypropylmethylcellulose phthalate, hydroxypropylmethylcellulose acetate succinate and the like. Of these, low-substituted hydroxypropylcellulose is preferable. More preferred is low-substituted hydroxypropylcellulose having a hydroxypropoxyl group content of 5-16 wt % (e.g., LH-11, LH-21, LH-31, LH-22, LH-32, LH-20, LH-30, LH-33 (trade names, manufactured by Shin-Etsu Chemical Co., Ltd.) etc.) and the like.

The content of the cellulose or cellulose derivative in the coating layer of the coated preparation of the present invention is generally 0.5-70 parts by weight, preferably about 2-about 50 parts by weight, more preferably about 2-about 30 parts by weight, per 100 parts by weight of the coating layer.

Since cellulose or a cellulose derivative (preferably cellulose derivative) is contained in the coating layer, the coated preparation of the present invention has a construct constituting a coating layer, which comprises cellulose or a cellulose derivative as a skeleton and is maintained in an aqueous solvent, wherein pioglitazone or a pharmaceutically acceptable salt thereof is dissolved in an organic acid (solution) in the construct to afford an aqueous solution. As a result, the coated preparation of the present invention can, as compared to conventional preparations, remarkably increase the maximum blood concentration and AUC of pioglitazone after administration, and remarkably decrease inter-individual relative standard deviation (RSD) in AUC.

In addition, since the coated preparation of the present invention has a construct constituting a coating layer, which comprises cellulose or a cellulose derivative as a skeleton and is maintained in an aqueous solvent, wherein pioglitazone or a pharmaceutically acceptable salt thereof is dissolved in an organic acid (solution) in the construct to afford an aqueous solution, it can enhance bioavailability as compared to conventional preparations. Specifically, the bioavailability of the coated preparation of the present invention exceeds 75% when the preparation is administered to dogs.

In the present specification, the bioavailability can be determined by, for example, dividing AUC at the time of non-intravenous administration of a given amount of pioglitazone by AUC at the time of intravenous administration of the same amount of pioglitazone. For example, when the bioavailability of a low dose pioglitazone immediate release drug product of the present invention is administered orally is to be calculated, the formula may be as the following:

$$\text{Bioavailability}(\%) = (\text{AUC of oral administration}/\text{AUC of intravenous administration}) \times 100.$$

When pioglitazone is dissolved in the construct to afford an aqueous solution, a similar effect as achieved by the administration of solution can be provided, which is expected to increase maximum blood concentration, AUC and bioavailability.

Here, the aqueous solvent in the present specification includes water, KCl—HCl buffer (e.g., KCl—HCl buffer at pH 2.0), McIlvaine buffer (e.g., McIlvaine buffer at pH 2.2, pH 2.5 or pH 3.0) and the like. The construct constituting a coating layer, which comprises a cellulose derivative as a skeleton and is maintained in an aqueous solvent specifically means, for example, that the construct is present for not less than 10 minutes preferably in KCl—HCl buffer (pH 2.0, 900 mL) under conditions of Paddle Method (50 rpm), more preferably in McIlvaine buffer (pH 2.2, 900 ml) under conditions of Paddle Method (50 rpm), still more preferably in McIlvaine buffer (pH 2.5, 900 ml) under conditions of Paddle Method (50 rpm), particularly preferably in McIlvaine buffer (pH 3.0, 900 mL) under conditions of Paddle Method (50 rpm).

The Paddle Method in the present specification means measurement according to the Japanese Pharmacopoeia 14th Edition, General Tests, Dissolution Test Method 2, unless particularly indicated.

The coated preparation of the present invention may contain additives conventionally used in the technical field of formulation of preparations. Examples of the additive include excipient, disintegrant, binder, lubricant, colorant, pH regulator, surfactant, stabilizer, corrigent, sweetener, flavor, glidant, antistatic agent, light shielding agent, antioxidant, reducing agent, chelating agent and the like. These additives are used in an amount conventionally employed in the technical field of formulation of preparations. In addition, these additives may be used in a mixture of two or more kinds thereof in an appropriate ratio.

Examples of the excipient include saccharides; crystalline cellulose; starches such as corn starch, potato starch, wheat starch, rice starch, partly pregelatinized starch, pregelatinized starch, porous starch, dextrin, carboxymethyl starch and the like; anhydrous calcium phosphate, precipitated calcium carbonate, calcium silicate, powder cellulose, gelatin, light anhydrous silicic acid, synthetic aluminum silicate, magnesium aluminometasilicate, magnesium oxide, calcium phosphate, calcium carbonate, calcium sulfate.

Examples of saccharides include sugar, starch sugar, lactose, honey and sugar alcohol. Two or more kinds of these saccharides may be used in a mixture in an appropriate ratio.

Examples of sugar include sucrose, white soft sugar, glycosyl sucrose [coupling sugar (trade name)], fructooligosaccharide and palatinose.

Examples of starch sugar include glucose, maltose, powdered starch syrup, starch syrup, fructose and trehalose.

Examples of lactose include lactose, isomerized lactose (lactulose) and hydrogenated lactose (lactitol).

Examples of honey include various kinds of honey generally used for eating.

Examples of sugar alcohol include sorbitol, mannitol (specifically, D-mannitol), maltitol, hydrogenated glucose syrup, xylitol, reduced paratinose and erythritol.

The saccharides are preferably sugar alcohol, starch sugar and sucrose, more preferably mannitol, trehalose and sucrose. Of these, mannitol and trehalose are preferable. From the aspect of suppressing color change of the preparation (specifically color change under preservation conditions), in the coated preparation of the present invention, the coating layer is preferably to contain mannitol or trehalose.

When saccharides are used for the coated preparation, the content thereof is for example, 5-90 parts by weight, preferably 5-40 parts by weight, per 100 parts by weight of the coated preparation.

Particularly, when the coated preparation of the present invention contains mannitol or trehalose, the content of mannitol or trehalose is preferably 5-40 parts by weight, more preferably 5-30 parts by weight, per 100 parts by weight of the coated preparation.

Examples of crystalline cellulose include CEOLUS KG801, KG802, PH101, PH102, PH301, PH302, PH-F20, RC-A591NF (trade names, manufactured by Asahi Kasei Chemicals Corporation), including one called microcrystalline cellulose.

Examples of disintegrants include carboxymethylcellulose, calcium carboxymethylcellulose (carmellose calcium), sodium carboxymethyl starch, carmellose sodium, croscarmellose sodium, crospovidone [preferably, Kollidon CL, CL-M, CL-F, CL-SF (trade name, BASF JAPAN LTD.); Polyplasdone XL, XL-10, INF-10 (trade name, ISP JAPAN LTD.)], low-substituted hydroxypropylcellulose [preferably low-substituted hydroxypropylcellulose having a hydroxypropoxyl group content of 5-16 wt %, such as LH-11, LH-21, LH-31, LH-22, LH-32, LH-20, LH-30, LH-33 (trade name, manufactured by Shin-Etsu Chemical Co., Ltd.) etc.], hydroxypropyl starch, cornstarch and partly pregelatinized starch.

When a disintegrant is used for the coated preparation of the present invention, the content of the disintegrant is, for example, 0.5-50 parts by weight, preferably 1-25 parts by weight, per 100 parts by weight of the coated preparation.

Examples of binders include hydroxypropylcellulose [preferably HPC-SSL, SL, L (trade name, NIPPON SODA CO., LTD.)], hydroxypropylmethylcellulose, povidone (polyvinylpyrrolidone), arabic gum powder, sucrose, gelatin, pullulan, methylcellulose, crystalline cellulose, low-substituted hydroxypropylcellulose [preferably low-substituted hydroxypropylcellulose having a hydroxypropoxyl group content of 5-16 wt %, such as LH-11, LH-21, LH-31, LH-22, LH-32, LH-20, LH-30, LH-33 (trade name, manufactured by Shin-Etsu Chemical Co., Ltd.) etc.], macrogol, dextran, polyvinyl alcohol and starch paste. Of these, hydroxypropylcellulose is preferable.

When a binder is used for the coated preparation of the present invention, the content of the binder is, for example, 0.01-50 parts by weight, preferably 0.1-10 parts by weight, per 100 parts by weight of the coated preparation.

Examples of lubricants include stearic acid, magnesium stearate, calcium stearate, talc, sucrose esters of fatty acids, sodium stearyl fumarate, waxes, DL-leucine, sodium lauryl sulfate, magnesium lauryl sulfate, macrogol and light anhydrous silicic acid (e.g., AEROSIL). Of these, magnesium stearate is preferable.

Examples of colorants include food colors such as Food Yellow No. 5 (Sunset Yellow, same as Food yellow No. 6 in the US), Food Red No. 2, Food Blue No. 2 and the like, food lake colors, yellow ferric oxide (yellow iron oxide), diiron trioxide (red iron oxide), riboflavin, riboflavin organic acid ester (e.g., riboflavin butyrate), riboflavin phosphate or alkali metal salt thereof or alkaline earth metal salt thereof, phenolphthalein, titanium oxide, lycopene, beta-carotene.

Examples of the pH regulator include citrate, phosphate, carbonate, tartrate, fumarate, acetate and amino acid salt.

Examples of the surfactant include sodium lauryl sulfate, polysorbate 80, polyoxyethylene (160) polyoxypropylene (30) glycol, polyoxyethylene (196) polyoxypropylene (67) glycol and polyoxyethylene hydrogenated castor oil 60.

Examples of the stabilizer include sodium ascorbate, tocopherol, tetrasodium edetate, nicotinamide, cyclodextrins; alkaline earth metal salts (e.g., calcium carbonate, calcium hydroxide, magnesium carbonate, magnesium hydroxide, magnesium silicate, magnesium aluminate) and butylhydroxyanisole.

Examples of the corrigent include ascorbic acid, (anhydrous) citric acid, tartaric acid and malic acid.

Examples of the sweetener include aspartame, acesulfame potassium, thaumatin, saccharin sodium and dipotassium glycyrrhizinate. Of these, aspartame is preferable.

Examples of the flavor include menthol, peppermint oil, lemon oil and vanillin.

Examples of the glidant include light anhydrous silicic acid and hydrated silicon dioxide. Here, the light anhydrous silicic acid may be any containing hydrated silicon dioxide ($SiO_2 \cdot nH_2O$) (n is an integer) as a main component and, as concrete examples thereof, Sylysia 320 (trade name, FUJI SILYSIA CHEMICAL LTD.), AEROSIL 200 (trade name, NIPPON AEROSIL CO., LTD.) and the like can be used.

Examples of the antistatic agent include talc and light anhydrous silicic acid.

Examples of the light shielding agent include titanium oxide.

Examples of the antioxidant include dibutylhydroxytoluene (BHT), tocopherol, tocopherol ester (e.g., tocopherol acetate), ascorbic acid or alkali metal salt thereof or alkaline earth metal salt thereof, lycopene, beta-carotene.

Examples of the reducing agent include cystine and cysteine.

Examples of the chelating agent include EDTA or alkali metal salt thereof or alkaline earth metal salt thereof.

The coated preparation of the present invention may have an intermediate layer formed between the core and the coating layer comprising pioglitazone or a salt thereof. Using such intermediate layer, an adverse effect (e.g., decomposition of pioglitazone) of the organic acid in the core on pioglitazone or a salt thereof in the coating layer can be prevented, and the durability of the coated preparation can be prolonged.

The dosage form of the coated preparation of the present invention is generally a solid preparation. Examples of the solid preparation include tablet, caplet, capsule, powder, granule and troche. Of these, granule, capsule and tablet are preferable. Semi-solid dosage forms, such as a gel containing the coated preparation, and liquid preparations containing a solution of pioglitazone of the appropriate dosage are also useable in accordance with the present invention.

The shape of the solid preparation is not particularly limited, and may be any of round, caplet, doughnut, oblong and the like.

The solid preparation may be coated with a coating agent, and may have a mark and letters for identification and further a score line for partition.

Examples of the coating base include sugar coating base, aqueous film coating base, enteric film coating base, sustained-release film coating base and the like.

As the sugar coating base, sucrose is used and one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trade name)], polyvinylpyrrolidone and the like; polysaccharides such as pullulan and the like; and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose, cellulose acetate and the like; acrylic acid polymers such as aminoalkyl methacrylate copolymer RS [Eudragit RS (trade name)], ethyl acrylate-methyl methacrylate copolymer suspension [Eudragit NE (trade name)] and the like; and the like.

Two or more kinds of the above-mentioned coating bases may be used in a mixture in an appropriate ratio. In addition, coating additives may also be used during coating.

Examples of the coating additive include light shielding agents and/or colorants such as titanium oxide, talc, ferric oxide and the like; plasticizers such as polyethylene glycol, triethyl citrate, castor oil, polysorbates and the like; and the like.

The coated preparation of the present invention can be produced by using the above-mentioned various additives according to a conventional method in the technical field of formulation of preparations.

For example, the coated preparation of the present invention can be produced by:

(1) mixing an organic acid with additives where necessary to give a core containing an organic acid, (2) forming a coating layer comprising pioglitazone or a salt thereof on the surface of the core by coating the core containing an organic acid with pioglitazone or a salt thereof and additives where necessary, and (3) drying and sieving the obtained coated product as necessary.

In addition, the coated preparation of the present invention can also be produced by mixing the coated product after drying and sieving with an additive as necessary, and compression molding or filling the mixture in a capsule.

Here, the mixing (including granulation, drying, milling and the like) is performed, for example, using a preparation forming machine such as a V-type mixer, a tumbler mixer, a high speed agitating granulator (FM-VG-10; POWREX CORPORATION), an all-round kneader (Hata Tekkosho, Co., Ltd.), a fluidized-bed dryer/granulator (LAB-1, FD-3S, FD-3SN; POWREX CORPORATION), a box vacuum dryer (Kusunoki Machinery Co., Ltd.), a screen mill (P-3; Showa Kagaku Kikai Kosakusho Co., Ltd.), centrifugal fluidized-bed granulator (CF-mini, CF-260, CF-360; Freund Corporation), dry granulator, spray drying granulator, rotating fluidized-bed granulator (MP10; POWREX CORPORATION) and the like.

For coating, for example, a preparation producing machine such as a centrifugal fluidized-bed granulator (CF-mini, CF-260, CF-360; Freund Corporation), a rolling granulator (MP10; POWREX CORPORATION), a general fluidized-bed coating apparatus, a wurster type coating apparatus and the like is used, and a centrifugal fluidized-bed granulator is preferably used.

The compression molding is performed, for example, by punching generally at a pressure of 0.3-35 kN/cm$^2$ using a single-punch tableting machine (KIKUSUI SEISAKUSHO LTD.), a rotary tableting machine (KIKUSUI SEISAKUSHO LTD.), Auto-graph (Shimadzu Corporation) and the like.

Examples of capsules which can be used for capsule filling include gelatin capsules (e.g., LICAPS®, CONI-SNAP® caps, PRESS-FIT® caps and XPRESS-FIT™ caps), hydroxypropylmethylcellulose (HPMC) capsules (e.g. VCAPS®), pullulan capsules and the like (preferably, hydroxypropylmethylcellulose (HPMC) capsules).

The above-mentioned core containing organic acid is coated by the following method or a method analogous thereto:

1) a method including spraying pioglitazone or a salt thereof together with additives as necessary (preferably, an excipient [preferably crystalline cellulose (which may be omitted), saccharides (preferably mannitol, trehalose, sucrose)], a disintegrant (preferably L-HPC)) onto the core containing an organic acid, while spraying a solution of a binder (preferably, hydroxypropylcellulose) in a solvent [e.g., one or more kinds selected from water, alcohol (e.g., methanol, ethanol, propanol, isopropanol), acetone and acetonitrile; preferably water or isopropanol] (the solution may be a dispersion);

2) a method including spraying a solution of a binder (preferably, hydroxypropylcellulose) containing pioglitazone or a salt thereof, and an additive as necessary (preferably, excipient [preferably crystalline cellulose (which may be omitted), saccharides (preferably, mannitol, trehalose, sucrose)], a disintegrant (preferably, L-HPC)) in a solvent [e.g., one or more kinds selected from water, alcohol (e.g., methanol, ethanol, propanol, isopropanol), acetone, acetonitrile; preferably water or isopropanol] (the solution may be dispersion) onto the core containing organic acid;

3) a method including spraying pioglitazone or a salt thereof together with an additive as necessary (preferably, excipient [preferably, crystalline cellulose (which may be omitted), saccharides (preferably, mannitol, trehalose, sucrose)], a disintegrant (preferably, L-HPC), and a binder (preferably, hydroxypropylcellulose)) onto the core containing organic acid, while, e.g., methanol, ethanol, propanol, isopropanol), acetone, acetonitrile; preferably water or isopropanol]; or 4) a method including spraying pioglitazone or a salt thereof together with cellulose or a cellulose derivative [preferably, cellulose derivative (more preferably L-HPC)], and an additive as necessary (preferably, excipient [preferably crystalline cellulose (which may be omitted), saccharides (preferably, mannitol, trehalose, sucrose)] onto the core containing organic acid, while spraying a solution of a binder (preferably, hydroxypropylcellulose) in a solvent [e.g., one or more kinds selected from water, alcohol (e.g., methanol, ethanol, propanol, isopropanol), acetone and acetonitrile; preferably water or isopropanol] (the solution may be dispersion).

The core of the coated preparation of the present invention preferably consists of at least one kind of organic acid selected from citric acid, tartaric acid, malic acid and ascorbic acid [preferably citric acid (particularly anhydrous citric acid)].

In addition, the coating layer comprising pioglitazone or a salt thereof in the coated preparation of the present invention preferably consists of pioglitazone or a salt thereof (preferably pioglitazone hydrochloride), an excipient [preferably crystalline cellulose (which may be omitted), saccharides (preferably mannitol, trehalose, sucrose; more preferably mannitol)], a disintegrant (preferably L-HPC) and a binder (preferably hydroxypropylcellulose), or it is a coating layer consisting of pioglitazone or a salt thereof (preferably pioglitazone hydrochloride), an excipient [preferably crystalline cellulose (which may be omitted), saccharides (preferably mannitol, trehalose, sucrose; more preferably mannitol)], cellulose or a cellulose derivative (preferably a cellulose derivative, more preferably L-HPC) and a binder (preferably hydroxypropylcellulose).

(b) Orally Disintegrating Tablet (ODT) Formulation

The invention provides for an orally disintegrating tablet wherein the active ingredient is pioglitazone or a pharmaceutically acceptable salt thereof (for example as described in U.S. Ser. No. 12/810,779, corresponding to US 2010-0278390, incorporated by reference in its entirety).

Using the production method of the present invention, an orally disintegrating tablet, which is rapidly disintegrated in an oral cavity, has desired appropriate hardness, and is superior in the storage stability since it shows only a small decrease in the hardness and a small increase in the tablet thickness even under high temperature and/or high humidity conditions without any packages, can be easily produced by simple steps. In addition, using the production method of the present invention, tableting troubles during tableting, such as capping and binding to a die inner wall and the like can be suppressed.

As used herein, an orally disintegrating tablet or ODT means a tablet that is rapidly disintegrated by saliva in an oral cavity.

The orally disintegrating tablet of the present invention may comprise (a) one or more saccharides or sugar alcohols selected from the group consisting of mannitol (particularly, D-mannitol), lactose (particularly, lactose hydrate), xylitol, sucrose, erythritol and glucose (to be also referred to as component (a) in the present specification) and (b) low substituted hydroxypropylcellulose (to be also referred to as component (b) in the present specification).

As component (a), mannitol and lactose are preferable.

The content of component (a) is preferably 50-95 wt %, more preferably 70-90 wt %, of the weight of the preparation. Component (a) can also be optionally dissolved in water and the like as mentioned below and used as a binding solution for agitation granulation. The content of the above-mentioned component (a) also includes the amount used as the binding solution. When used as the binding solution, the amount thereof is preferably less than 10 wt %, more preferably about 2-5 wt %, of the content of the above-mentioned component (a).

The average particle size of the saccharides and sugar alcohols of component (a) is preferably not more than 50 μm, more preferably 10-20 μm. When the average particle size exceeds 50 μm, the disintegration time tends to be extended.

The average particle size of the saccharides and sugar alcohols of the above-mentioned component (a) means their initial average particle size of the starting materials before being subjected to the agitation granulation and means that they have a particle size within the above-mentioned range, and the average particle size may change during the subsequent production processes and storage of the preparation.

The saccharides and sugar alcohols of component (a) having an average particle size within the above-mentioned range are commercially available. Alternatively, the commercially available products may be pulverized with a conventional method to adjust the particle size and thereafter used.

In one embodiment, the average particle size in the present specification shows a 50% accumulated particle size in the particle size distribution measured based on a dry method using an airflow-type disperser.

In the present invention, the low substituted hydroxypropylcellulose does not require a particular limitation on the grade and the like, and a commercially available product can be used. For example, low substituted hydroxypropylcellulose having a hydroxypropoxyl group content of about 7.0-12.9 wt % can be used.

The content of the low substituted hydroxypropylcellulose is preferably 3-20 wt %, more preferably 5-15 wt %, of the weight of the preparation.

The orally disintegrating tablet of the present invention preferably contains (c) one or more saccharides or sugar alcohols selected from the group consisting of powder hydrogenated maltose starch syrup, maltose, maltitol, sorbitol and trehalose (to be also referred to as component (c) in the present specification). The presence of component (c) further increases the tablet hardness.

As component (c), powder hydrogenated maltose starch syrup and maltose are preferable.

The content of component (c) is preferably 0.1-5 wt %, more preferably 0.1-1 wt %, of the weight of the preparation.

The orally disintegrating tablet of the present invention does not substantially contain a starch disintegrant (e.g., corn starch, sodium carboxymethyl starch, rice starch, wheat starch, pregelatinized starch, partly pregelatinized starch etc.).

Here, substantially free of in the present specification means absence of an amount that adversely influences the storage stability of preparations. Specifically, the content of the starch disintegrant is preferably not more than 5 wt %, more preferably not more than 3 wt %, still more preferably not more than 1 wt %, of the weight of the preparation.

The orally disintegrating tablet of the present invention preferably contains thaumatin. The content of thaumatin is preferably 0.1-5 wt %, more preferably 0.1-1 wt %, of the weight of the preparation. Thaumatin is a sweetener generally added for masking the bitterness of an active ingredient. In the present invention, the presence of thaumatin provides effects of improved moldability during production and increased hardness.

Besides the above-mentioned components, the orally disintegrating tablet of the present invention may contain additives generally used for solid preparations. The additive is, for example, excipient, disintegrant other than starch disintegrant, binder, lubricant, fluidizer, corrigent, sweetening agent, coating agent, colorant, flavor and the like. The content of these additives is not particularly limited and may be appropriately selected from an amount conventionally used in the pharmaceutical field. The total amount of the additives except for components (a) and (b) (when component (c) is contained, the total amount of the additives except for components (a)-(c)) is preferably not more than 50 wt %, more preferably not more than 25 wt %, of the weight of the preparation.

The orally disintegrating tablet of the present invention contains pioglitazone as an active ingredient. The content of the active ingredient may be appropriately determined based on the amount used for clinical application, and it is preferably not more than 50 wt %, more preferably not more than 25 wt %, of the weight of the preparation.

The orally disintegrating tablet of the present invention is characterized by production including steps of granulating a composition containing the above-mentioned components (a) and (b) (preferably the above-mentioned components (a), (b) and (c)) by an agitation granulation method, and compression-molding the obtained granulation product. It is considered that since the granulation product becomes spherical by agitation granulation, tableting troubles (particularly, binding to die inner wall) in the subsequent compression-molding step are prevented in the present invention.

The production method of the orally disintegrating tablet of the present invention is explained in detail in the following.

1. Granulation Step

The above-mentioned components (a) and (b) (preferably the above-mentioned components (a), (b) and (c)), an optional active ingredient and/or an optional additive are mixed. The additive is, for example, excipients (e.g., talc), disintegrants other than starch disintegrants (e.g., crospovidone), sweetening agents, colorants, flavors and the like. The active ingredient may be mixed with an excipient (e.g., talc) first and then coated with a coating agent (e.g., aqueous ethylcellulose dispersion, triacetine) for the purpose of masking bitterness and the like.

The above-mentioned mixture is granulated by an agitation granulation method. The agitation granulation method is also generally referred to as a high-speed agitation granulation method. Here, the (high-speed) agitation granulation method is a method including adding dropwise or spraying a binder solution on a mixed powder by rotating the main wings set on the bottom of a granulating machine to form large particles, and grinding the particles by a chopper on the side wall to give granules desired particle size (Yoshihisa SAGAWA, Pharmaceutical Product Preparation Technique, CMC Publishing CO., LTD., published in 2002, page 108).

The granulation by an agitation granulation method can be performed by using what is called an agitation granulator (also referred to as a high-speed agitation granulator) (e.g., high-speed mixer, LFS-GS-2J (manufactured by Fukae Powtec); VERTICAL GRANULATOR (manufactured by POWREX CORPORATION); NEW SPEED KNEADER (manufactured by OKADA SEIKO CO., LTD.) etc.). The rotation speed of the main wings and chopper is not particularly limited, and may be appropriately selected from the range generally used at agitation granulation. Specifically, a binding solution (e.g., water or, where necessary, other additives may be blended) is added to the above-mentioned mixture in the agitation granulator, and the mixture is granulated. When thaumatin is added in the present invention, though not particularly limited, it may be added to the binding solution.

2. Compression Molding Step

To the granulation product obtained in the granulation step is added an optional active ingredient and/or an optional additive (e.g., fluidizers (e.g., light anhydrous silicic acid), lubricants (e.g., magnesium stearate, sodium stearyl fumarate, calcium stearate), flavors), and the mixture is blended and compression-molded by a tableting machine and the like. The compression molding pressure (tableting pressure) may be appropriately selected from the range generally used at tablet production. While the pressure is not particularly limited, it is preferably not less than 200 kg.

The orally disintegrating tablet of the present invention produced as mentioned above has desired appropriate hardness, is rapidly disintegrated in an oral cavity, and shows superior storage stability, even though it can be easily produced without cumbersome steps of humidification and drying after tableting and a special facility of an external lubrication system.

The hardness of the orally disintegrating tablet of the present invention is generally about 3-6 kg when the tablet has a diameter of 6-7 mm and a thickness of about 3 mm. Here, the hardness of the tablet in the present specification is a value measured by a Schleuniger tablet hardness tester (Dr. Schleuniger Pharmatron AG).

While the disintegration time of the orally disintegrating tablet of the present invention in an oral cavity varies depending on the form of preparation, dose and the like, it is generally within 60 sec, preferably within 30 sec.

The orally disintegrating tablet of the present invention is not particularly limited as regards the size and form, and may be a scored tablet having a cleavage line.

The orally disintegrating tablet of the present invention can be ingested without water.

VI. Uses

The methods of the invention are used to delay onset of Alzheimer's disease or a phase or stage indicative of or associated with development of Alzheimer's disease in a patient at risk of developing Alzheimer's disease. The invention also provides for pharmaceuticals that can be used to delay onset of Alzheimer's disease, a symptom thereof, or a phase or stage indicative of or associated with development of Alzheimer's disease in a patient at risk of developing Alzheimer's disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Having now generally described the invention, the same will be more readily understood through reference to the following Examples which are provided by way of illustration, and are not intended to be limiting of the present invention, unless specified.

The following examples are put forth for illustrative purposes only and are not intended to limit the scope of what the inventors regard as their invention.

Example 1

Low Dose Pioglitazone Granules 1

Pioglitazone HCl (228.1 g), mannitol (ROQUETTE, 335.8 g) and L-HPC (LH-32 Shin-Etsu Chemical Co., Ltd., 115.0 g) are mixed to give a dusting powder. Hydroxypropylcellulose (HPC-SSL, NIPPON SODA CO., LTD., 9.2 g) is dissolved in purified water (194.6 g) to give a binding liquid. Anhydrous citric acid crystal (Jungbunzlauer, 1380 g) is fed into a centrifugal fluidized-bed granulator (CF-360, Freund Corporation) and coated with the dusting powder while spraying the binding liquid. The resulting granules are dried under reduced pressure at 40° C. for 18 hr, and sieves of 16 mesh and 42 mesh are used to give granules at the range of 16-42 mesh (aperture 0.355-1.00 mm). The granules (7193.6 g) are mixed with talc (Matsumurasangyo Co., Ltd., 3.2 g) and light anhydrous silicic acid (AEROSIL, NIPPON AEROSIL, 3.2 g) in a tumbler mixer (60 L, Showa Kagaku Kikai Kosakusho Co., Ltd.) to give pioglitazone hydrochloride granules having the following composition per 450 mg.

| | |
|---|---|
| anhydrous citric acid crystal | 300 mg |
| Pioglitazone HCl | 49.59 mg |
| mannitol | 73.01 mg |
| L-HPC | 25 mg |
| hydroxypropylcellulose | 2 mg |
| talc | 0.2 mg |
| light anhydrous silicic acid | 0.2 mg |
| total | 450 mg |

The resulting composition can be diluted in an appropriate excipient to give the desired dosage, including any of the dosages recited herein, for example, 0.5 mg, 1.5 mg, 4.5 mg and 9.0 mg. The desired dosages can then be formulated into oral dosage forms, such as capsules, tablets or caplets.

Example 2

Low Dose Pioglitazone Granules 2

Pioglitazone HCl (9.90 g), mannitol (ROQUETTE, 186.2 g) and L-HPC (LH-32 Shin-Etsu Chemical Co., Ltd., 39.96 g) are mixed to give a dusting powder. Hydroxypropylcellulose (HPC-SSL, NIPPON SODA CO., LTD., 12.00 g) is dissolved in purified water (340.2 g) to give a binding liquid. Anhydrous citric acid crystal (Jungbunzlauer, 400.0 g) is fed into a centrifugal fluidized-bed granulator (CF-260, Freund Corporation) and coated with the dusting powder while spraying the binding liquid. The resulting granules are dried under reduced pressure at 40° C. for 18 hrs, and sieves of 16 mesh and 42 mesh are used to give granules of pioglitazone hydrochloride at the range of 16-42 mesh (aperture 0.355-1.00 mm) having the following composition.

| | |
|---|---|
| anhydrous citric acid crystal | 53.33 mg |
| pioglitazone HCl | 1.102 mg |
| mannitol | 20.69 mg |
| L-HPC | 4.44 mg |
| hydroxypropylcellulose | 0.36 mg |
| total | 79.92 mg |

Example 3

Low Dose Pioglitazone Capsules

The low dose pioglitazone granules 2 formulated in Example 2 (39.96 g) are mixed with talc (Matsumurasangyo Co., Ltd., 0.02 g) and light anhydrous silicic acid (AEROSIL, NIPPON AEROSIL, 0.02 g) in a glass bottle to give pioglitazone hydrochloride granules having the following composition per 80 mg. The pioglitazone hydrochloride granules (80 mg) are filled in No. 4 hypromellose capsules (Qualicaps Co., Ltd.) to give capsules having the following composition.

| Component | amount added |
|---|---|
| granule obtained in Example 2 | 79.92 mg |
| talc | 0.04 mg |
| light anhydrous silicic acid | 0.04 mg |
| No. 4 hypromellose capsule | 1 capsule |

Example 3

Pioglitazone Liquid Formulation 1

A liquid formulation of pioglitazone is prepared using the materials as follows.
Materials:
Citric Acid, Sigma, C1857, lot 089K0057
Distilled Water, Ice Mountain
HPMC, USP, Sigma, H-3785, lot 122K0149
Pioglitazone HCl, Takeda, lot 345
Polyethylene Glycol 200, Sigma, P3015, lot 098K0056
Polysorbate 80, NF, Spectrum, P0138, lot XV0879
Propylene Glycol, USP/FCC, Fisher, P355, lot 080676
Sucrose, USP, Sigma, S3929, lot 086K0022
Syrup NF, Spectrum, SY105, lot XP0703
Approximately 0.01496 g of pioglitazone HCl is transferred into a 50-mL graduated cylinder. 0.69 g of polyethylene glycol 200 is added and mixed to wet the solids. 1.51 g of propylene glycol is added and the resulting mixture is swirled and is sonicated to mix and dissolve the solids. 1.48 g of polysorbate 80 is added and is swirled to mix. 0.50373 g of citric acid is added and is swirled to mix. Some citric acid solids remain undissolved. Approximately 10 mL of distilled water is added and is swirled to mix/dissolve the solids. The mixture is diluted to 50 mL with distilled water and is mixed well such that all solids are in solution to formulate a liquid having the following pioglitazone concentration of about 15 mg/50 mL or 0.3 mg/mL.

In practicing the methods of the present invention, a selected low dose pioglitazone can be administered to a subject using the pioglitazone liquid of this Example 4. For example, 5 mL or a teaspoonful will deliver a dose of about 1.5 mg pioglitazone HCl, whereas as 15 mL or a tablespoonful will deliver a dose of about 4.5 mg of pioglitazone HCl. Two tablespoonfuls or about 30 mL of the pioglitazone liquid of this Example 4 will deliver about 9 mg of pioglitazone HCl per dose.

Example 5

Pioglitazone Liquid Formulation 2

A liquid formulation of pioglitazone is prepared using the materials as follows.
Materials:
Citric Acid, Sigma, C1857, lot 089K0057
Distilled Water, Ice Mountain
HPMC, USP, Sigma, H-3785, lot 122K0149
Pioglitazone HCl, Takeda, lot 345
Polyethylene Glycol 200, Sigma, P3015, lot 098K0056
Polysorbate 80, NF, Spectrum, P0138, lot XV0879
Propylene Glycol, USP/FCC, Fisher, P355, lot 080676
Sucrose, USP, Sigma, S3929, lot 086K0022
Syrup NF, Spectrum, SY105, lot XP0703

Approximately 0.01613 g of pioglitazone HCl is added to a 50-mL volumetric flask. 1.0043 g of citric is acid is added. Approximately 25 mL of distilled water is added and the resulting mixture is swirled and is sonicated to wet the solids. The mixture is diluted to volume, i.e., about 50 mL, with distilled water, is mixed well and then is sonicated for 1-2 minutes such that all solids are in solution.

The liquid pioglitazone solution of this Example 5 will have the following pioglitazone concentration of about 16.13 mg/50 mL or 0.326 mg/mL.

In practicing the methods of the present invention using the liquid pioglitazone solution of this Example 5, a selected low dose pioglitazone can be administered to a subject. For example, 5 mL or a teaspoonful will deliver a dose of about 1.63 mg pioglitazone HCl, whereas as 15 mL or a tablespoonful will deliver a dose of about 4.89 mg of pioglitazone HCl. Two tablespoonfuls or about 30 mL of the pioglitazone liquid of this Example 5 will deliver about 9.78 mg of pioglitazone HCl per dose.

Example 6

Pioglitazone Suspension Formulation 1

A suspension formulation of pioglitazone is prepared as follows.
Preparation of Pioglitazone HCl Suspension A: Suspending Vehicle is Syrup NF (density of Syrup NF is 1.30 g/mL).
0.025 g of Pioglitazone HCl Drug Substance is transferred into a glass mortar and pestle. The Pioglitazone HCl is wetted with about 4 drops of the Suspending Vehicle and mixed/ground for about 1 minute to form a smooth uniform paste. The suspending vehicle is added until the total weight in the mortar and pestle is about 1 g. The resulting mixture is mixed/ground for 1 minute. More suspending vehicle is added until the total weight is about 8 g. The resulting mixture is mixed for 1 minute. More suspending vehicle is added until the total weight is about 48 g and then mixed for 1 minute. Suspending Vehicle is added until the total weight of the suspension is 130.04 g and mixed for 1 minute. The mixture from the mortar is poured into a 4 oz reagent bottle. The bottle is capped and the suspension is shaken by hand for about 1 minute.

The theoretical concentration of pioglitazone HCl is determined;
25.60 mg/130.04 g=0.1969 mg/g (as the HCl salt—not the free base)
25.60 mg/100 mL=0.2560 mg/mL (as the HCl salt—not the free base)

In practicing the methods of the present invention using the liquid pioglitazone suspension 1 of this Example 6, a selected low dose pioglitazone can be administered to a subject. For example, 5 mL or a teaspoonful will deliver a dose of about 1.28 mg pioglitazone HCl, whereas as 15 mL or a tablespoonful will deliver a dose of about 3.84 mg of pioglitazone HCl. Two tablespoonfuls or about 30 mL of the liquid pioglitazone suspension 1 of this Example 6 will deliver about 7.68 mg of pioglitazone HCl per dose.

Example 7

Pioglitazone Suspension Formulation 2

Preparation of Suspending Vehicle B: 0.6% HPMC+10% Sucrose
0.6% HPMC Solution:
1000 mL of distilled water is transferred into a 2-L Erlenmeyer flask. The water is heated to 60° C. with constant stirring. 6 g of HPMC is weighed and is dispersed uniformly into the heated water. Heating of the mixture is continued until it just reaches boiling. The mixture is removed from the heat and is placed in an ice bath with constant stirring. The mixture is stirred until it clarifies and cools to room temperature.
Suspending Vehicle: (0.6% HPMC with 10% Sucrose):
80 g of sucrose is added to a 1000-mL glass bottle. 50 mL of distilled water is added and the mixture is mixed by shaking such all of the solids are dissolved. 0.6% HPMC Solution is added until the total weight is 800 g. The mixture is shaken to dissolve the solids.
The density of the solution is 103.86 g/100 mL.
Preparation of Pioglitazone HCl Suspension B: Suspending Vehicle is 0.6% HPMC+10% Sucrose
0.025 g of Pioglitazone HCl Drug Substance is transferred into a glass mortar and pestle. The Pioglitazone HCl is wetted with about 4 drops of the Suspending Vehicle and is mixed/ground for about 1 minute to form a smooth uniform paste. Suspending vehicle is added until the total weight in the mortar and pestle is about 1 g. The mixture is mixed/ground for 1 minute. Additional suspending vehicle is added until the total weight is about 8 g and then mixed for 1 minute. Additional suspending vehicle is add until the total weight is about 20 g and then is mixed for 1 minute. Additional suspending vehicle is added until the total weight is about 40 g-50 g and then is mixed for 1 minute. Suspending Vehicle is added until the total weight of the suspension is 103.31 g and is mixed for 1 minute. The mixture is poured from the mortar into a 4 oz reagent bottle. The bottle is capped and the suspension is shaken by hand for about 1 minute.

The theoretical concentration of pioglitazone HCl is determined;

26.44 mg/103.31 g=0.25593 mg/g (as the HCl salt—not the free base)

26.44 mg/100 mL=0.2644 mg/mL (as the HCl salt—not the free base)

In practicing the methods of the present invention using the liquid pioglitazone suspension 2 of this Example 7, a selected low dose pioglitazone can be administered to a subject. For example, 5 mL or a teaspoonful will deliver a dose of about 1.322 mg pioglitazone HCl, whereas as 15 mL or a tablespoonful will deliver a dose of about 3.966 mg of pioglitazone HCl. Two tablespoonfuls or about 30 mL of the liquid pioglitazone suspension 2 of this Example 7 will deliver about 7.932 mg of pioglitazone HCl per dose.

Example 8

Heretofore there has not been an ability to predict which people are more likely to develop pathophysiological changes of the kind described herein that lead to cognitive impairment and ultimately Alzheimer's dementia. The TOMM40 rs10524523 genotype along with age and possibly other factors constitute a prognostic biomarker to determine which subjects are at risk for developing cognitive impairment of the Alzheimer's type in the next 5-7 years, and thus provide the opportunity for medical intervention in the early phase of this progressive and devastating disease. The clinical benefit of this intervention may be confirmed in a clinical study of the general form described below. In addition, a prospective clinical study of this nature would provide sufficient data to determine the positive predictive and negative predictive values of the prognostic biomarker, an understanding of which is needed prior to introduction of the biomarker into clinical practice.

OPAL Study rs10524523 (523) is a poly-T length polymorphism that occurs in linkage disequilibrium (LD) with APOE genotypes, and is inherited together with the APOE genotype on each strand in the LD region. Essentially a single intronic variant of TOMM40 varies by poly-T length, with the longer forms of the variant associated with approximately a 7 year difference in the age of onset compared to the shorter forms. Based on the presenting age of the normal subject, a determination of 'High risk' of onset of cognitive impairment and AD over the next 5-7 years, or 'Low risk' is determined.

This study provides a novel genetically-based model for the identification of subjects in large diverse community-based populations who are at higher risk of AD onset within 5-7 years by combining clinical risk assessments based on the presence of specific genotypes related to Alzheimer's disease onset and clinical expression. The study:

uses the TOMM40 rs10524523 (523) poly-T length polymorphisms in the TOMM40-APOE LD region, perhaps in conjunction with the APOE genotype, for predicting the age of onset of cognitive impairment and Alzheimer's disease. Specifically, to determine if a discrete Alzheimer's disease diagnostic test can separate subjects into 'High-risk' and 'Low-risk' groups for Alzheimer's disease; and uses a low dose PPARγ Agonist daily for 60 months (5 years) versus placebo in pre-symptomatic subjects who are at High risk as defined by their TOMM40-APOE genotype of Alzheimer's disease, to delay the onset of Alzheimer's disease related dementia symptoms.

Cognitively normal subjects between the ages of 62-87 are evaluated for susceptibility to AD within the next 5-7 years and are tested for effects of pioglitazone on onset of AD. The definition cognitively normal is calculated as within 1.5 standard deviations (SD) of the population mean taking into account the age of the subject and the level of education for the assessments listed below. Scores below this cut off are considered cognitively impaired. The following cognitive assessments are used to assess cognitive function at enrollment and throughout the course of the study.

The cognitive assessment scales are chosen to be sensitive to early deficits in Alzheimer's disease. These assessment scales are used in the ADAPT study (1), which is a prevention study for Alzheimer's disease using NSAID therapy carried out in 2004. The Mini Mental examination (2MS-E) is used in the Women's Health Initiative Study for hormone replacement therapy (2) for the prevention of AD. Thus, the cognitive assessments include:

Modified Mini Mental State Examination (3MS-E)
Brief Visuospatial Memory Test (Revised) (BVMT-R)
Hopkins Verbal Learning Test (Revised) (HVLT-R)
Rivermead Behavioural Memory Test (RBMT)
Generative Verbal Fluency Test (GVFT)
Digit Span Test (DST)

Enrollment into the study is based solely on the scores from these assessments. For randomization into the study, the individuals in addition are given a DNA test consisting of APOE genotyping and measurement of the 523 poly-T repeat lengths to assess their risk status as 'High risk' or 'Low risk' of developing cognitive impairment or AD over the next 5-7 years. The following designs describe the study procedure Study Design Assumptions The end points are 1) change in a measure of cognition from baseline based on the scores from the neuropsychological assessments and 2) diagnosis of Alzheimer's disease in accordance with NINCDS-ADRDA criteria (National Institute of Neurological and Communicative Disorders and Stroke (NINCDS) and Alzheimer's Disease and Related Disorders Association (ADRDA). These are either taken as two primary end points or a combined event end point.

Sample Size Calculations

The sample size calculation is determined for a log-rank test of time to event data based on the above end points. It is assumed that the conversion rate for the 'High risk' group will be 20% at the end of 5 years follow-up based on data from previous prevention studies (3,4). A sample size of 374/group is required to detect a 50% improvement in this conversion rate (i.e. from 20% to 10%) at the 5% level of significance and with 90% power. A drop out rate of 20% for both placebo and treatment groups over the five year period is built into this calculation. This sample size is not adjusted for multiple comparisons.

A further assumption is made that the 'Low risk' group has a conversion rate of 10% based on incidence rates of Alzheimer's disease in the general population (4). The sample size required to compare this group with the 'High risk' placebo group is again 374/group with 90% power and a 5% significance level.

Study Designs

The diagnostic test defines which patients are at 'High risk' of conversion to Alzheimer's disease or cognitive impairment, (High risk) and which patients are at 'Low risk' of conversion (Low risk). The investigators are blinded to the results of the diagnostic test and central randomization is used to maintain this blind. The main objectives for any design are:

to determine whether the diagnostic test can discriminate between 'High' and 'Low risk' subjects, and to evaluate the effect of treatment on the conversion rate of 'High risk' patients.

All subjects recruited for these studies will be cognitively normal as defined previously.

Preferred Study Design

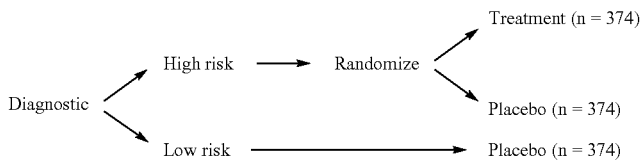

In this design, only the 'High risk' group is randomized to receive placebo or treatment. This is a simple design that, for example, utilizes a total sample size of 1122 subjects. This design allows two hypotheses to be investigated: the first relates to the ability of the diagnostic to define the 'High' and 'Low risk' groups by comparing the data from the placebo treated subjects; the second relates to whether the treatment can improve the conversation rate by comparing the data from the treatment and placebo groups of the 'High risk' arm.

Alternative Design 1

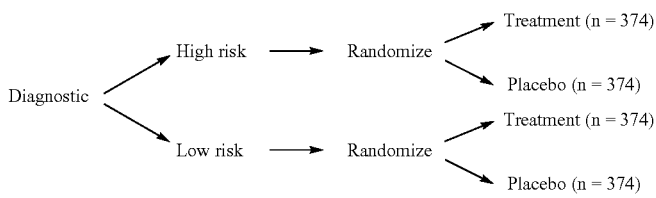

In this design a fourth group is added to allow the effect of treatment to be evaluated in the 'Low risk' group. This design may increase the total sample size to 1496 patients.

This design may provide useful information if the 'Low risk' group has a higher than expected conversion rate. However, there are potential concerns with this design in terms of risk/benefit to the 'Low risk' group. Subjects in the 'Low risk' group might be at risk of experiencing side effects with treatment with no expected benefit to their conversion rate.

Alternative Design 2

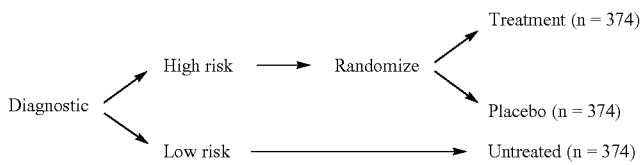

This design is the same as the preferred design except that the 'Low risk' group remains untreated and serves as an observational group. This design will be able to meet the objectives of the study but there are a number of potential pitfalls:

unable to blind the untreated arm so results of the diagnostic test will not be blinded, possibly higher drop out rate in the 'Low risk' group if subjects feel that being observed but not 'treated' is without benefit.

will not be comparing like with like which could be an issue if there is a 'placebo' effect (unlikely for time to event but possible for cognitive testing).

The sample size calculations are based on detecting a difference of 10 percentage points between conversion rates at the end of 5 years. An increase in numbers allows a signal to be detected earlier with a smaller difference. If it is assumed that the conversion rate in the 'High risk' group is 5%/year then after three years approximately 15% of the subjects may have converted to Alzheimer's disease or show cognitive impairment. Assuming that treatment can improve this rate by 50% then the expected conversion rate in the treated group will be 7.5%. In order to detect the difference with 90% power an the 5% significance, 559 subjects per group will be required resulting in a total sample size for the preferred design of 1677. This increase in subject numbers permits investigation of a family of age of onset curves associated with each TOMM40-APOE haplotype. An exploratory analysis is used to investigate the effects of age by including age as a covariate in a Cox's proportional hazards time to event analysis, which allows the investigation of covariates. A certain percentage of subjects are defined as having mild cognitive impairment (MCI) based on the neuropsychological assessments at screening. The study will only recruit those subjects who are defined as cognitively normal based on the neuropsychological assessments.

References

1) ADAPT Research Group: Cognitive Function Over Time in the Alzheimer's Disease Anti-inflammatory Prevention Trial (ADAPT) Results of a Randomized, Controlled Trial of Naproxen and Celecoxib: Archives of Neurology, Vol 65 (No 7), July 2008
2) Stephen R. Rapp; Mark A. Espeland; Sally A. Shumaker et al: Effect of Estrogen Plus Progestin on Global Cognitive Function in Postmenopausal Women, The Women's Health Initiative Memory Study: 2003; 289(20):2663-2672 *JAMA*
3) Curtis L. Meinert, John C. S. Breitner: Chronic disease long-term drug prevention trials: Lessons from the Alzheimer's Disease Anti-inflammatory Prevention Trial (ADAPT): Alzheimer's & Dementia 4 (2008) S7-S14
4) Stephen Salloway, Stephan Correia: Alzheimer disease: Time to improve its diagnosis and treatment: Cleveland Clinic Journal Of Medicine Volume 76, Number 1 January 2009
5) ADAPT Research Group: Cognitive Function Over Time in the Alzheimer's Disease Anti-inflammatory Prevention Trial (ADAPT) Results of a Randomized, Controlled Trial of Naproxen and Celecoxib: Archives of Neurology, Vol 65 (No 7), July 2008
6) Stephen R. Rapp; Mark A. Espeland; Sally A. Shumaker et al: Effect of Estrogen Plus Progestin on Global Cognitive Function in Postmenopausal Women, The Women's Health Initiative Memory Study: 2003; 289(20):2663-2672 *JAMA*
7) Curtis L. Meinert, John C. S. Breitner: Chronic disease long-term drug prevention trials: Lessons from the Alzheimer's Disease Anti-inflammatory Prevention Trial (ADAPT): Alzheimer's & Dementia 4 (2008) S7-S14
8) Stephen Salloway, Stephan Correia: Alzheimer disease: Time to improve its diagnosis and treatment: Cleveland Clinic Journal Of Medicine Volume 76, Number 1 January 2009

Example 9

BOLD Study

The invention provides for the following exemplary dose finding analysis.

The invention provides for measuring pharmacodynamic changes in response to different low doses of pioglitazone. The pharmacodynamic measure that is relevant is a change in regional blood oxygenation coupled to neuronal activity as measured by blood oxygen level dependent functional magnetic resonance imaging (BOLD fMRI).

Neuroprotection and mitochondrial biogenesis are among the physiological effects of thiazolidinediones. In one embodiment, pioglitazone treatment of subjects may increase the metabolic capacity of active regions of the brain. This change in metabolic capacity may be observable using BOLD fMRI.

BOLD fMRI is a widely used technology for non-invasive whole brain imaging. This technique measures a change in regional blood oxygenation coupled to neuronal activity.

BOLD fMRI measures the relative change in the ratio of oxy- to deoxyhemoglobin in the brain that occurs as a result of neuronal activity. As neurons become active, there is a concomitant increase in cell metabolism, and blood flow increases to regions of increased neuronal activity to meet these metabolic demands. The result of this hemodynamic response is a measurable change in the local ratio of oxy-to deoxyhemoglobin. Oxyhemoglobin is diamagnetic and deoxyhemoglobin is paramagnetic and this difference in magnetism is detected by BOLD fMRI.

BOLD signals reflect complex and incompletely understood changes in cerebral blood flow (CBF), cerebral blood volume (CBV) and cerebral metabolic rate of oxygen consumption ($CMRO_2$) following neuronal activity. Candidate circuit elements for triggering various kinds of BOLD signals include excitatory neurons, mixed neuronal populations, astroglia, and axonal tracts or fibres of passage (described in detail in Lee et al., 2010 Nature 465: 788-792; Logothetis 2008 Nature 453: 869-878; Logothetis et al. 2001 Nature 412: 150-1571; Raichle 2010 Cell 14: 180-190, each of which is incorporated herein by reference in its entirety).

The study will utilize healthy, cognitively normal, older subjects of the age of interest, e.g., between 62 and 87. BOLD fMRI scanning will be performed using a scanner optimized for high-resolution structural and functional brain imaging (for example a state-of-the-art GE 3 Tesla scanner).

In one embodiment, the study is a double-blinded study using multiple cohorts, with each cohort receiving a different pioglitazone dose. In another embodiment, the study is of a serial design wherein the same cohort receives multiple different drug doses. The pharmacodynamic marker used to indicate changes in neuronal activity as a result of exposure to pioglitazone is a change in BOLD signal, especially in the dorsolateral prefrontal cortex and hippocampus which are associated with the higher cognitive functions that are impaired in Alzheimer's disease.

Each participant will undergo MRI scanning on at least three occasions:

1. pre-dose (to obtain a baseline or control value for each subject);
2. soon after receipt of the first dose (either at 2 hours or the approximate time of Cmax) to measure the result of acute exposure to drug; and
3. following 7 days of drug exposure (when pioglitazone serum concentration should each steady state and physiological effect of drug on mitochondrial function should have occurred).

Pioglitazone will be given every day for 7 days.

45 mg of pioglitazone (the marketed formulation for the treatment of type 2 diabetes) results in a Cmax of approximately 3 mM in serum (see Ghosh et al. 2007 Mol. Pharmacol 71: 1695-1702).

The test doses include:
a) 0.5 mg dose-approximately 33.3 nM serum and approximately 6.7 nM brain
b) 1.5 mg dose-approximately 100 nM serum and approximately 20 nM brain;
c) 4.5 mg dose-approximately 300 nM serum and approximately 50 nM brain;
d) 9 mg dose-approximately 600 nM serum and approximately 120 nM brain.

Magnetic Resonance Imaging Protocol Summary

General Participant Screening Procedure

Participants will be screened for ferrous metal implants that would preclude scanning prior to selection. Participants will be instructed to fast and abstain from caffeine, tobacco products and exercise for two hours prior to the scan session, and refrain from drinking alcohol and taking non-essential medication for twelve hours prior to scanning. Participants taking stimulant medications will be asked not to take them for at least 24 hours with physician approval. Two breath samples will be obtained to measure alcohol levels. Urine samples will be obtained to test for 5 drug metabolites (psychostimulants, cannabis, opiates and sedatives). Female participants will be given a urine pregnancy test, which must be negative for the participant to undergo scanning.

General Scanning Protocol

Subjects will be provided the opportunity to enter an MRI simulator to assess their comfort level for participating in the MRI session. Participants will then be instrumented for heart rate (photoplethysmograph) and blood pressure monitoring and will be positioned in the scanner. Head movement will be minimized using a combination of pillows and tape. After acquiring localizer scans, the protocols will be presented in the following fixed order, with a total scan time of approximately 60 minutes.

Structural MRI.

Measures of total and regional gray and white matter as well as CSF will be collected using high resolution MRI.

Technical Details: T1-weighted images with 1 mm isometric voxels will be acquired using the Array Spatial Sensitivity Encoding Techniques (ASSET) with fast spoiled gradient-recall (FSPGR). Image parameters will be optimized for contrast between white matter, gray matter and CSF (TR/TE/flip angle=7.484 ms/2.984 ms/12°, 256 mm FOV, 1 mm slice, 166 slices, 256×256 matrix, 1 Nex).

Perfusion MRI.

Measures of total and regional resting cerebral blood flow will be collected using Pulsed Arterial Spin Labeling (PASL).

Technical Details: Interleaved images with and without labeling will be acquired using a gradient echo-planar imaging (EPI) sequence. Acquisition parameters consist of the following: field of view (FOV)=22 cm, matrix=64×64, repetition time (TR)=3 sec, echo time (TE)=17 msec, label time=1.6 sec, delay time=0.8 sec, flip angle=90°. The resting perfusion scanning protocol takes approximately 6 minutes during which subjects will be instructed to lie still ad let their minds go blank, but keep their eyes open and stay awake. Data corresponding to fourteen slices (8 mm thickness with 2 mm gap) will be acquired in sequential order from inferior to superior.

Functional MRI (fMRI).

Archival working and episodic memory stimulation paradigms will be administered to measure patterns of neural activation, especially in the dorsolateral prefrontal cortex and hippocampus, associated with higher cognitive functions impaired in Alzheimer's disease using blood oxygen level-dependent (BOLD) fMRI.

Technical Details: A series of 34 interleaved axial functional slices will be acquired for full-brain coverage (TR/TE/flip=2000/31/60; FOV=240 mm; 3.75×3.75×3.8 mm voxels; interslice skip=0) using an inverse-spiral pulse sequence to reduce susceptibility artifact. High-resolution three-dimensional spin-echo co-planar structural images will be acquired in 68 axial slices (TR/TE/flip=12.2/5.3/20, voxel size=1×1×1.9 mm, FOV=240 mm, interslice skip=0) for normalization and subject averaging.

fMRI Stimulation Paradigms Working Memory; See Mattay et al., PNAS 2003 for details. Episodic Memory: See Bookheimer et al. New England Journal of Medicine 2000 for details.

Example 10

Rat BOLD Study

Low dose pioglitazone penetrates the blood brain barrier and induces changes in brain physiology.

It was determined whether low doses of pioglitazone HCl penetrate the blood brain barrier in sufficient concentrations to elicit functional or molecular changes in the brain. BOLD fMRI was used to measure drug-related changes in resting state functional connectivity across the whole brain.

Adult male Wistar rats (275±25 g) were housed separately and maintained on a 12-h light, 12-h dark schedule. Food and water was provided ad libitum. Animals were cared for in accordance with the guidelines published in the *Guide for the Care and Use of Laboratory Animals* (National Institutes of Health Publications No. 85-23, Revised 1985). Animal body weights were measured approximately 24 hours before Day-3, and on Study Days 3 and 6.

Pioglitazone HCl (PIO) was dissolved in 0.5 mol/L citric acid (CA) to yield a stock solution at a concentration of 0.32 mg/10 mL/kg. Other dosages were prepared by appropriate dilution of the stock solution with 0.5 mol/L CA to yield dose volumes of 10 mL/kg. Control rats received the vehicle at 10 mL/kg. Dose concentrations were based on the weight of the test article as supplied (i.e., as the HCl salt), with the dose adjusted to the most recent body weight of the animal. Daily dosing with PIO in solution was by oral gavage at approximately the same time every day. Animals were anesthetized lightly with isoflurane immediately beforehand to facilitate dosing.

All animals used in the imaging studies were acclimated to the MRI holding device by being placed in it for 15-90 minutes daily for at least 7 days, as previously described (Zhang et al. 2010 J Neurosci Methods 189: 186-196; Liang et al. 2011 J Neurosci 31: 3776-3783).

After the acclimation period, animals were assigned to 1 of 7 treatment arms matched for mean body weights (see Table 1). Dosing occurred once daily, at approximately the same time every day. All animals were imaged at Baseline (Study Day-3), approximately 2.5 to 3 h after dosing with vehicle. Dosing began 3 days later (Study Day 1). On this day, all animals were administered either vehicle (CA) or PIO depending on their group assignment. On Study Day 2, one vehicle group and one group treated with PIO at 0.08 mg/kg/day (Acute Arm) were imaged approximately 2.5 to 3 h after dosing. For all groups, dosing continued for seven days total. On Study Day 7, all rats were imaged approximately 2.5 to 3 h after administration of the final dose.

TABLE 1

Treatment Arms, Daily PIO Dose and Imaging Time Points

| Treatment Arm | Daily Dose (mg/kg) (N = 5/group) | Study Day −3 (Baseline) | Study Day 2 | Study Day 7 |
|---|---|---|---|---|
| Acute | 0, 0.08 | ✓ | ✓ | ✓ |
| Sub-chronic | 0, 0.04, 0.08, 0.16, 0.32 | ✓ | No imaging | ✓ |

Extrapolation to the corresponding dosage in humans was achieved while adjusting for the relative AUC for each. In humans, a dose of 7.5 mg is associated with an AUC of 2.8 μg·h/mL. In rats, a dose of 0.50 mg/kg/day PIO HCl is associated with an AUC of 7.11 μg·h/mL. Results of these calculations are presented in Table 2.

TABLE 2

Rat and Human-Equivalent Doses, Based on Extrapolated Exposures

| Parameter | Human Dose (mg total/day) | | | |
|---|---|---|---|---|
| | 1.5 | 3 | 6 | 12 |
| Rat Dose (mg/kg/day) | 0.04 | 0.08 | 0.16 | 0.32 |
| Targeted AUC (µg · h/mL) | 0.57 | 1.14 | 2.28 | 4.55 |

Animal preparation activities related to imaging were initiated to insure that the imaging itself occurred approximately 2.5 to 3 h after dosing. The animals were prepared for positioning in the restraint under isoflurane anesthesia as previously described (Zhang et al. 2010, supra). This procedure took approximately 10-15 minutes, by which time animals were usually fully conscious. Imaging was conducted on awake animals.

All MR experiments were conducted using a 4.7 T/40 cm horizontal magnet (Oxford, UK) interfaced with a BiospecBruker console (Bruker, Germany) and equipped with a 20 G/cm magnetic field gradient. A dual $^1$H radiofrequency (RF) coil configuration (Insight NeuroImaging Systems, Worcester, Mass.) consisting of a volume coil for exciting the water proton spins and a surface coil for receiving MRI signal was used; the volume and surface coils were actively tuned and detuned to prevent mutual coil coupling. This dual-coil configuration allowed for sufficient RF field homogeneity in the rat brain for RF transmission, while preserving the advantage of higher signal-to-noise ratio (SNR) provided by the smaller reception coil.

Anatomical images were acquired first using a multi-slice fast spin-echo sequence (RARE) with the parameters: repetition time (TR)=2125 ms; RARE factor=8; effective echo time (TE)=50 ms; matrix size=256×256; field of view (FOV)=3.2×3.2 cm$^2$; slice number=18; slice thickness=1 mm; n=8. Based on the geometry of anatomical images, multi-slice gradient-echo images covering the whole brain were acquired using echo-planar imaging (EPI) with the parameters: TR=1 s; Flip Angle=60°; TE=30 ms; matrix size=64×64; FOV=3.2×3.2 cm$^2$; slice number=18; slice thickness=1 mm. Rats were at rest during image acquisition. 200 volumes were acquired for each run; 9 runs were obtained for each rat.

Analysis of all fMRI data was conducted using Medical Image Visualization and Analysis (MIVA), Statistical Parametric Mapping (SPM8) software (Wellcome Department of Cognitive Neurology, London, UK) and Matlab (The Mathworks Inc., Natick, Mass., USA). The data was initially corrected for motion (threshold of 0.25 mm). Further preprocessing of the data included (a) slice scan time correction, (b) spatial smoothing using a 3D Gaussian filter (1-mm FWHM) to account for small variations in signal due to movement and vascular effects, and (c) voxel-wise linear detrending and high-pass filtering of frequencies (3 cycles per time course) to adjust for scanner drift between runs. Structural and functional data of each animal was then transformed to standard stereotaxic space embedded in MIVA to facilitate group analysis of functional data.

Correlational functional connectivity analysis was used to analyze resting-state functional connectivity. First, each animal was aligned and co-registered, based on anatomical images, to a fully segmented rat brain atlas. The co-registration procedure will provide the coordinates of each seed region of interest (ROI) in the image space. After co-registration and alignment, fMRI time courses for individual voxels in a seed ROI were obtained according to their corresponding coordinates. A time course for each seed region was created by regionally averaging time courses from all pixels inside the seed ROI. All ROI time courses were 0.002-0.08 Hz band-pass filtered. After filtering, the Pearson cross-correlation (CC) coefficient between ROI time courses was calculated and used to quantify the strength of functional connectivity.

To evaluate the effects of PIO on functional connectivity across the whole brain, we divided the whole rat brain into 57 ROIs. The strength of functional connectivity between each pair of ROIs was evaluated using the cross-correlation coefficient between the two ROI time courses. In total 57×56/2=1596 functional connections were assessed for each rsfMRI runs. This procedure was repeated for all 9 runs of each fMRI session and the connectivity strength of the corresponding connection was then averaged across 9 runs. As a result, the connectivity strength of 1596 connections was obtained for each rsfMRI scan session.

For each connection (i.e. a connection between each pair of ROIs), repeated measure ANOVA with the factors of imaging day, dosage and interaction were then calculated. Statistical significance level was set at P<0.005, uncorrected.

To evaluate the effects of PIO on the individual neural circuitries, seed-based correlational analysis was used (Zhang et al. 2010, supra). The CA1 of the hippocampus was selected as the seed ROI. The spatial pattern of brain regions that are functionally connected with the seed ROI was calculated in a voxel-by-voxel manner. First, the regionally averaged time course of the seed ROI was obtained as a reference. Cross-correlation coefficient between the time course of each voxel and the reference time course was then calculated. The correlation coefficient represented the functional connectivity strength between this voxel and the seed. A connectivity map for the seed ROI was created for each fMRI run and maps across nine runs were then averaged to create the connectivity map for each scan session. At last, a composite connectivity map was generated by averaging connectivity maps across rats of the same group that were imaged on the same day in the protocol (Zhang et al. 2010, supra).

FIG. 1 provides an example of the fMRI data and demonstrates that even the lowest doses of orally-administered, immediate release pioglitazone produce a change in metabolism in the central region of the deep cortical structures of the brain. This is consistent with an intracellular mitochondrial effect Conclusions 1. Relative to vehicle control, there is evidence that PIO treatment at doses as low as 0.04 mg/kg/day induces changes in multiple brain regions in the rat. This result indicates that low-dose PIO, administered orally, penetrates the blood brain barrier.
2. PIO, at doses as low as 0.08 mg/kg/day, induced functional changes as early as 24 hours, which was the earliest time point assayed after initiation of treatment.

As seen in FIG. 1, there appears to be a diminished signal at the 0.32 mg/kg/day dosage based on the appearance of these data. However, further testing will be done in order to confirm whether or not there is an actual diminished effect at this dosage relative to the lower dosages, and not simply reflecting intrinsic biological variability between the animal subjects.

Example 11

Exemplary Risk Determination

In order to identify subjects having normal cognition who are at high risk of developing cognitive impairment of the Alzheimer type (also termed hippocampal type) in the next 5 years based on TOMM40 rs1054523 (523) genotype, age, and possibly APOE genotype, age-of-onset data were studied from a cohort of 438 prospectively followed individuals from the Duke Bryan ADRC Memory Health and Aging study.

Table 3 summarizes an exemplary risk categorization based on 523 and APOE genotypes and age. Note that there appears to be a subset of VL/VL, APOE ε3/ε3 subjects who succumb to the onset of Alzheimer's disease between the ages of 51 and 59. These subjects are not considered in Table 3, which presents only the low risk subset of VL/VL carriers who are cognitively normal after age 62. An expanded risk categorization that includes the younger 'high risk' VL/VL APOE ε3/ε3 subjects is also contemplated.

TABLE 3

Exemplary Age Thresholds That Define High Risk for 523 Genotypes at Ages 62-83

| 523 or APOE Genotype | Age defining high risk |
|---|---|
| 523 L, L | All high risk |
| 523 L, VL | All high risk |
| 523 S, L | 74 |
| 523 S, S | 77 |
| 523 S, VL | 76 |
| 523 VL, VL | All low risk |
| APOE ε2/ε2 | All low risk |
| APOE ε2/ε3 | All low risk |
| APOE ε2/ε4 | All low risk |

An exemplary use of these assignments is straightforward. Table 3 is used to make assignments of individuals into the high- or low-risk groups (which may be irrespective of ethnicity) as follows:
1) individuals with a 523 genotype of (L,L) or (L,VL) are assigned to the high-risk group,
2) individuals with a 523 genotype of (VL,VL) (>62 years) or APOE genotype of (ε2/ε2) or (ε2/ε3) are assigned to the low-risk group,
3) for individuals with a 523 genotype of (S,S), (S,VL) or (S,L), an individual's current age is compared to the age in Table 2 to make the risk assignment.

For each 523 genotype, the corresponding age-of-onset curve for cognitive impairment is examined to identify the age where the slope of the curve indicates high risk of development of cognitive impairment in a 5-year window. The steep portion of the curve follows a relatively flat asymptote and has a characteristic time point (age) where a rapid increase in the proportion of individuals with cognitive impairment is observed (see FIG. 2 and FIG. 3).

Figure 3:
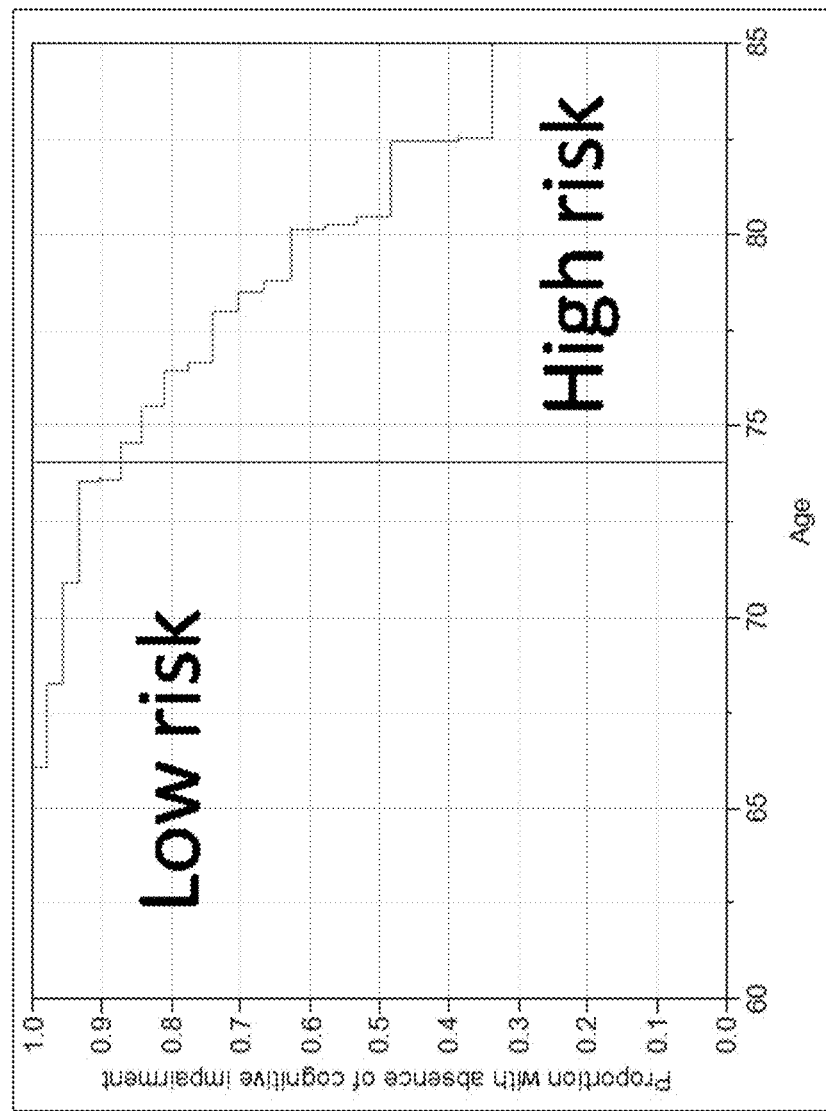
FIG. 3 presents the curve showing the age at onset of cognitive impairment of the Alzheimer type for individuals possessing the S,L 523 genotype. The Y axis shows the percent survival without cognitive impairment, while the X axis represents age. The curve shows a steep slope beginning at age 74 (vertical line). Individuals entering the trial at or above age 74 who possess the S,L 523 genotype are at high risk of developing cognitive impairment during the next 5 years. Data is obtained from the Duke Bryan ADRC cohort, N=72 subjects, 23 diagnosed with cognitive impairment, 49 cognitively normal.
Figure 4:
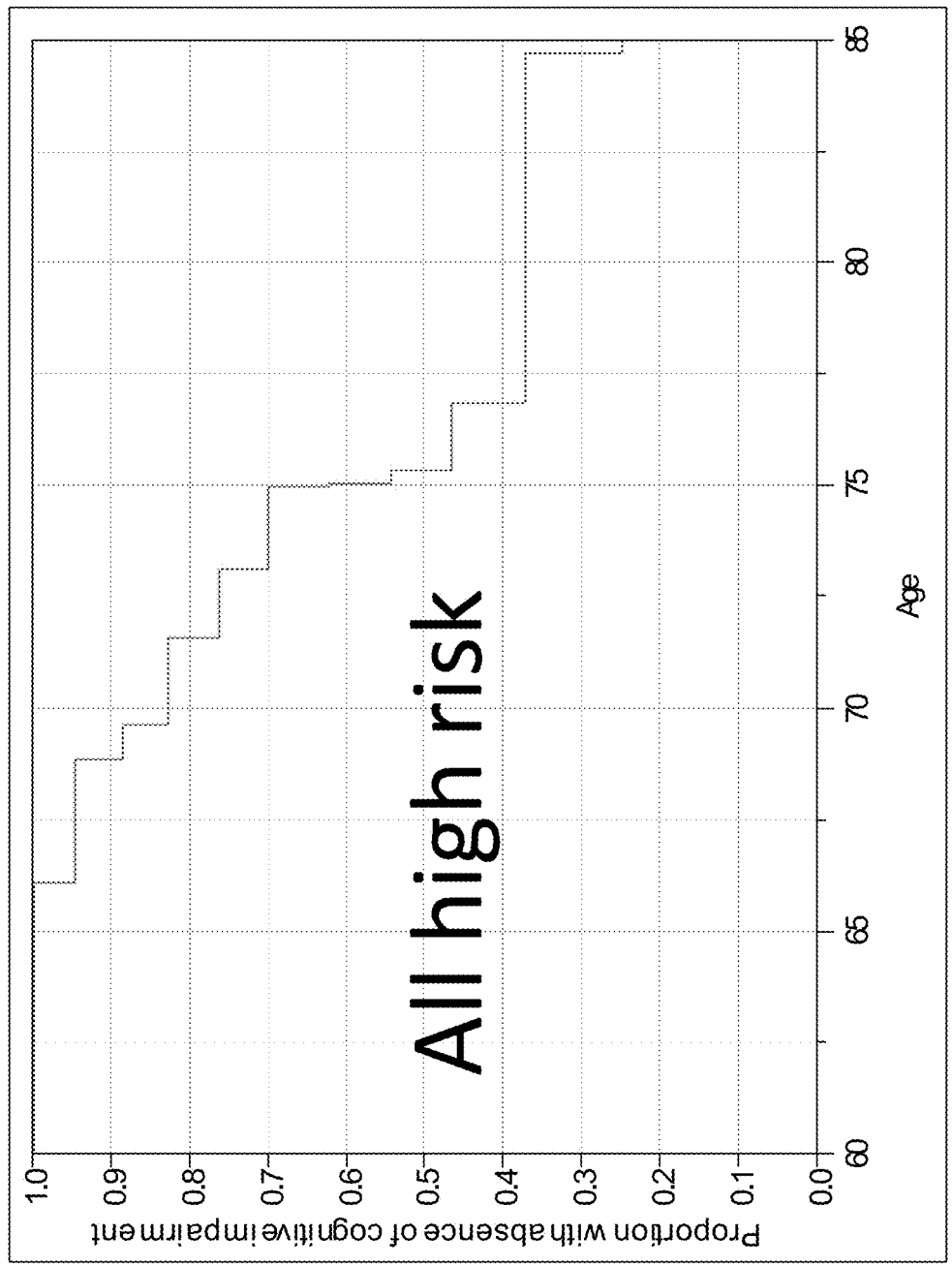
FIG. 4 presents the curve showing the age at onset of cognitive impairment of the Alzheimer's type for 523 L,L genotype. The Y axis shows the percent survival without CI, while the X axis represents age. Data obtained from the Duke Bryan ADRC cohort N=23 subjects, 11 diagnosed with CI, 12 cognitively normal.
Figure 5:
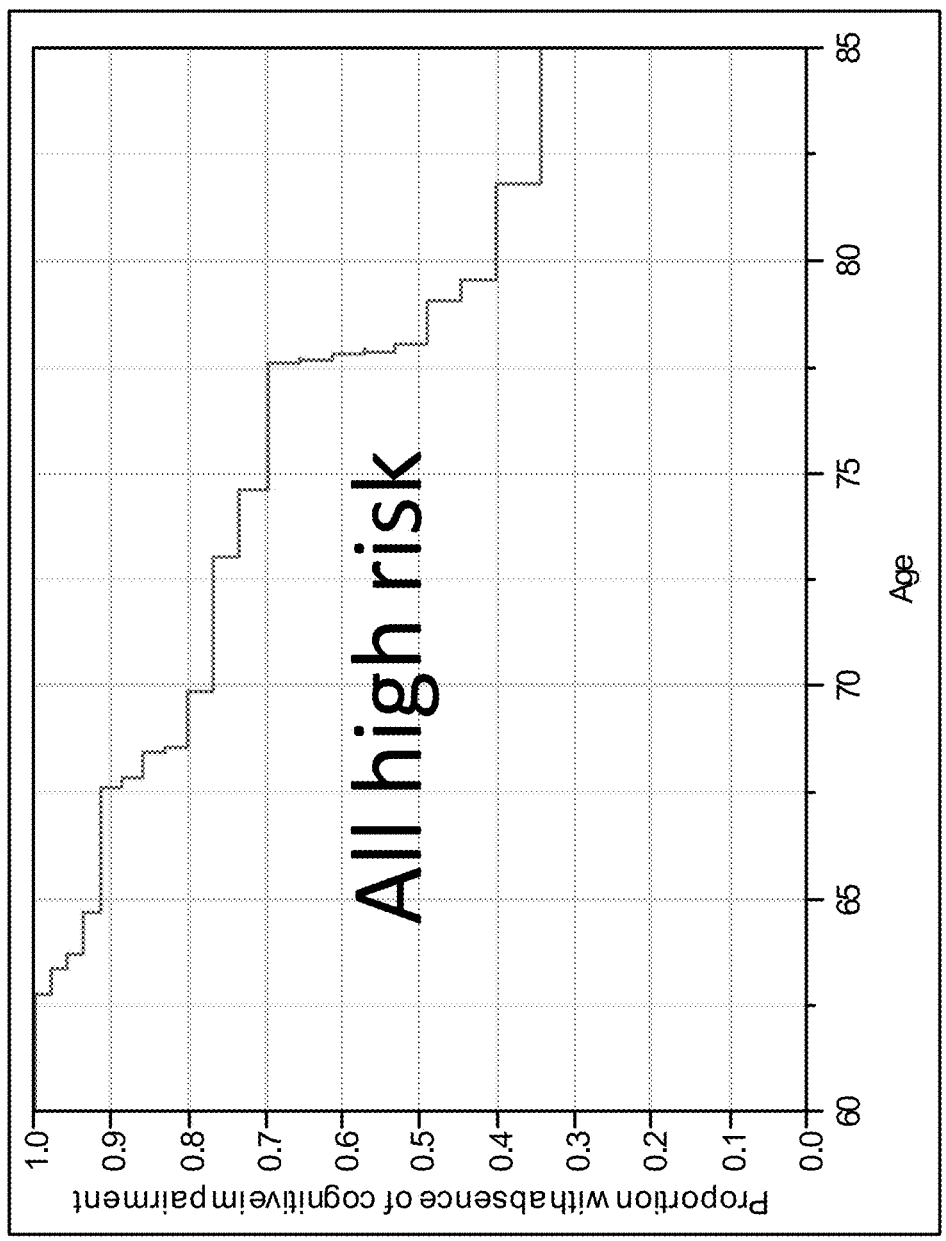
FIG. 5 presents the curve showing age at onset of cognitive impairment of the Alzheimer's type for 523 L,VL genotype. The Y axis shows the percent survival without CI, while the X axis represents age. Data obtained from the Duke Bryan ADRC cohort N=54 subjects, 24 diagnosed with CI, 30 cognitively normal.
Figure 6:
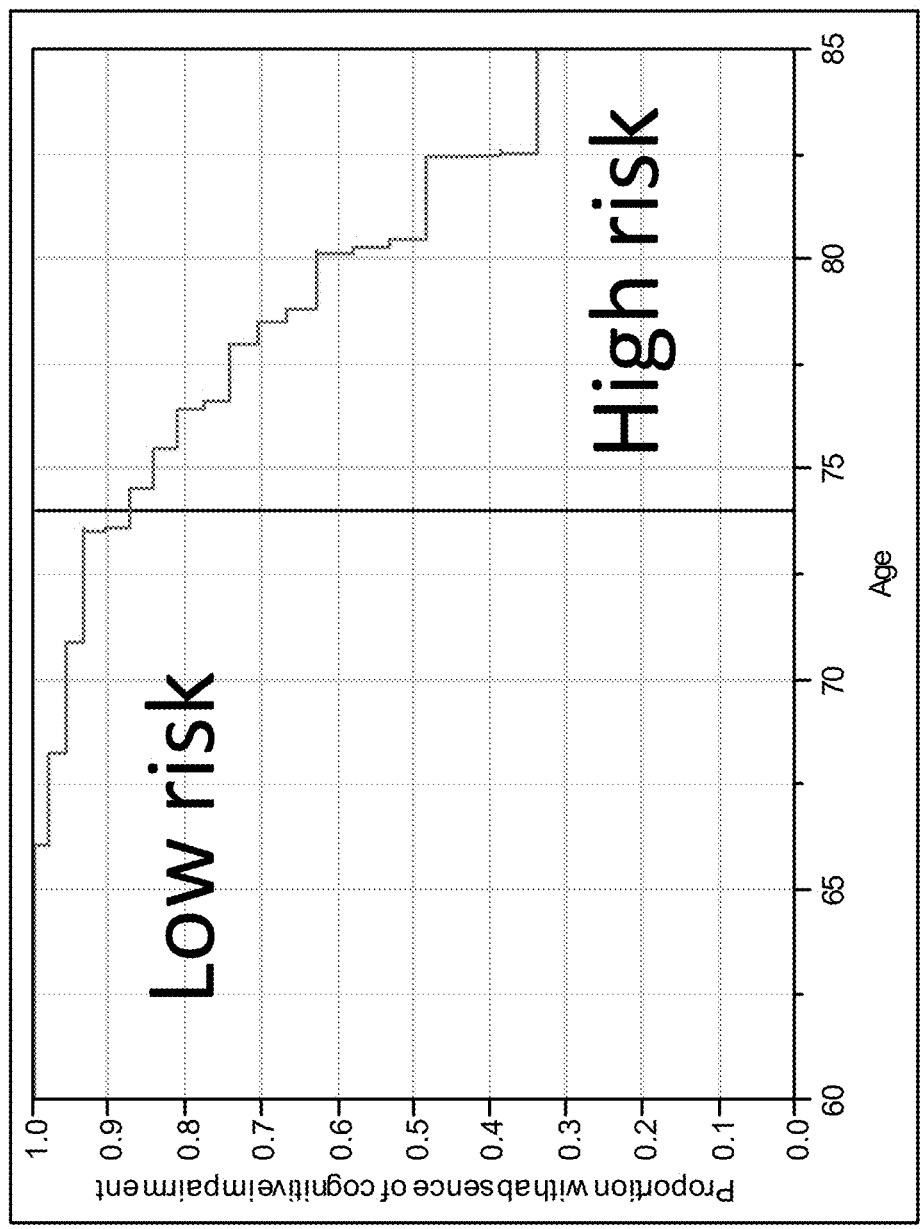
FIG. 6 presents the curve showing age at onset of cognitive impairment of the Alzheimer's type for 523 S,L genotype. The Y axis shows the percent survival without CI, while the X axis represents age. Data obtained from the Duke Bryan ADRC cohort N=72 subjects, 23 diagnosed with CI, 49 cognitively normal.
Figure 7:
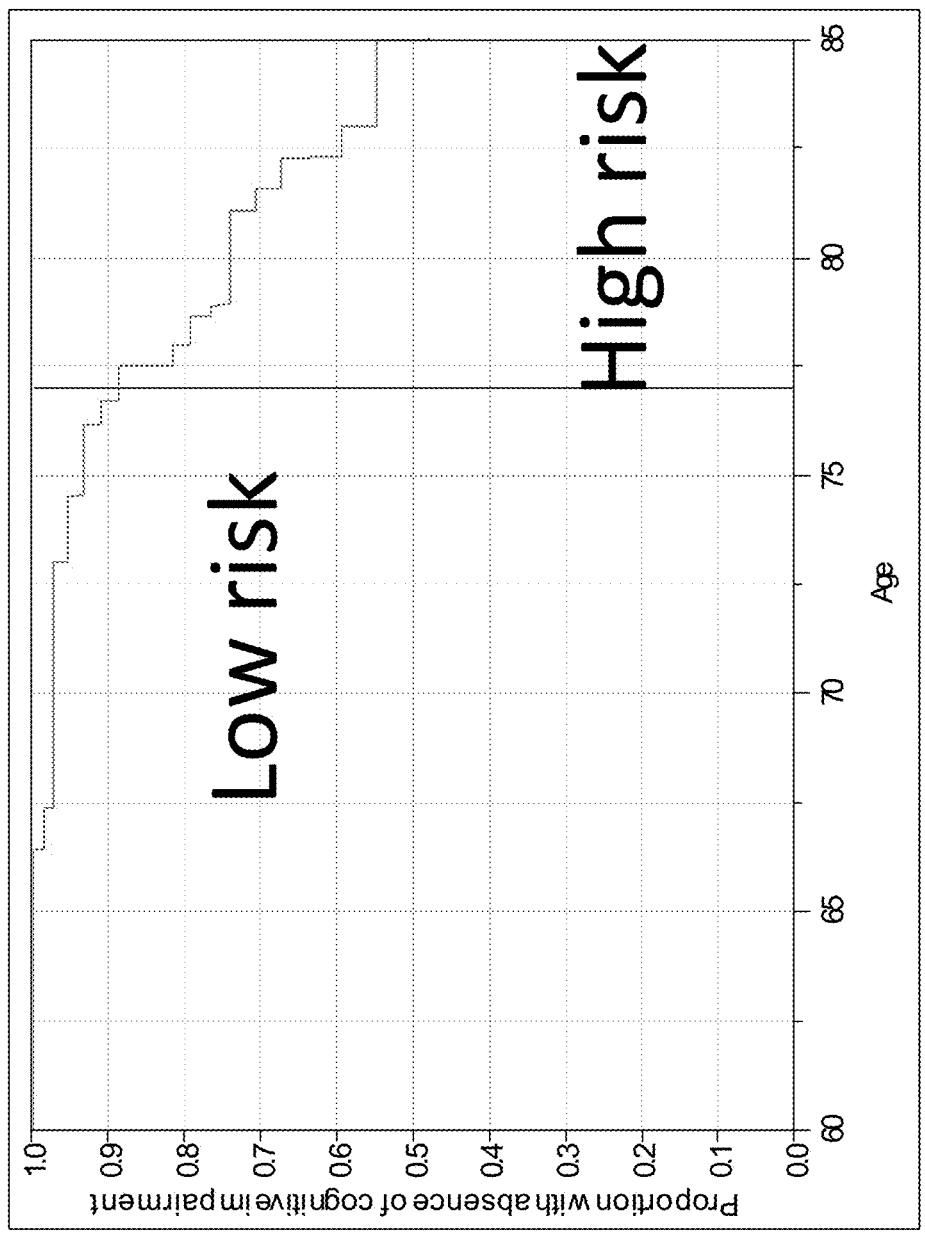
FIG. 7 presents the curve showing age at onset of cognitive impairment of the Alzheimer's type for 523 S,S genotype. The Y axis shows the percent survival without CI, while the X axis represents age. Data obtained from the Duke Bryan ADRC cohort N=100 subjects, 20 diagnosed with CI, 80 cognitively normal.
Figure 8:
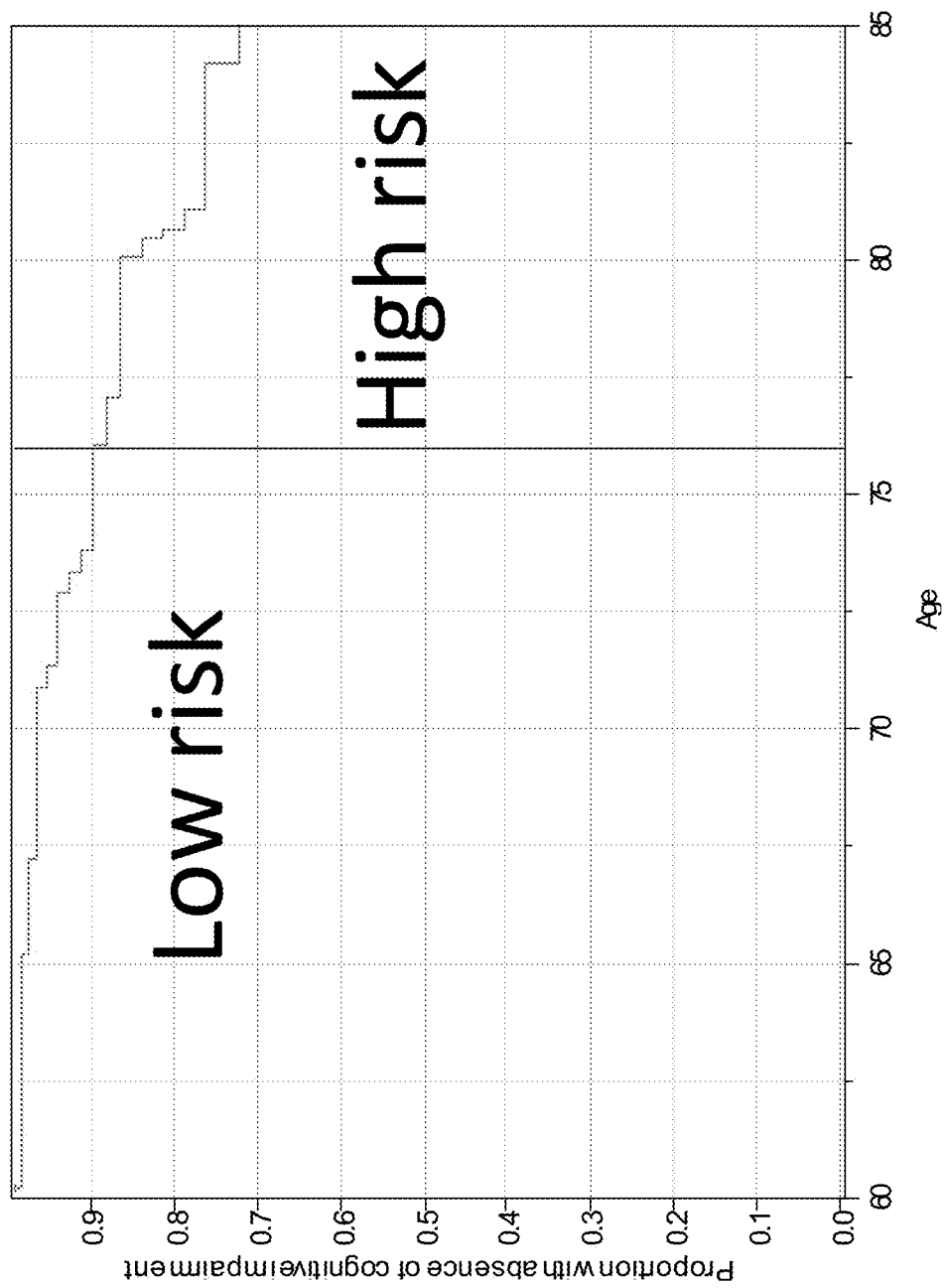
FIG. 8 presents the curve showing age at onset of cognitive impairment of the Alzheimer's type for 523 S,VL genotype. The Y axis shows the percent survival without CI, while the X axis represents age. Data obtained from the Duke Bryan ADRC cohort N=138 subjects, 22 diagnosed with CI, 116 cognitively normal.
Figure 9:
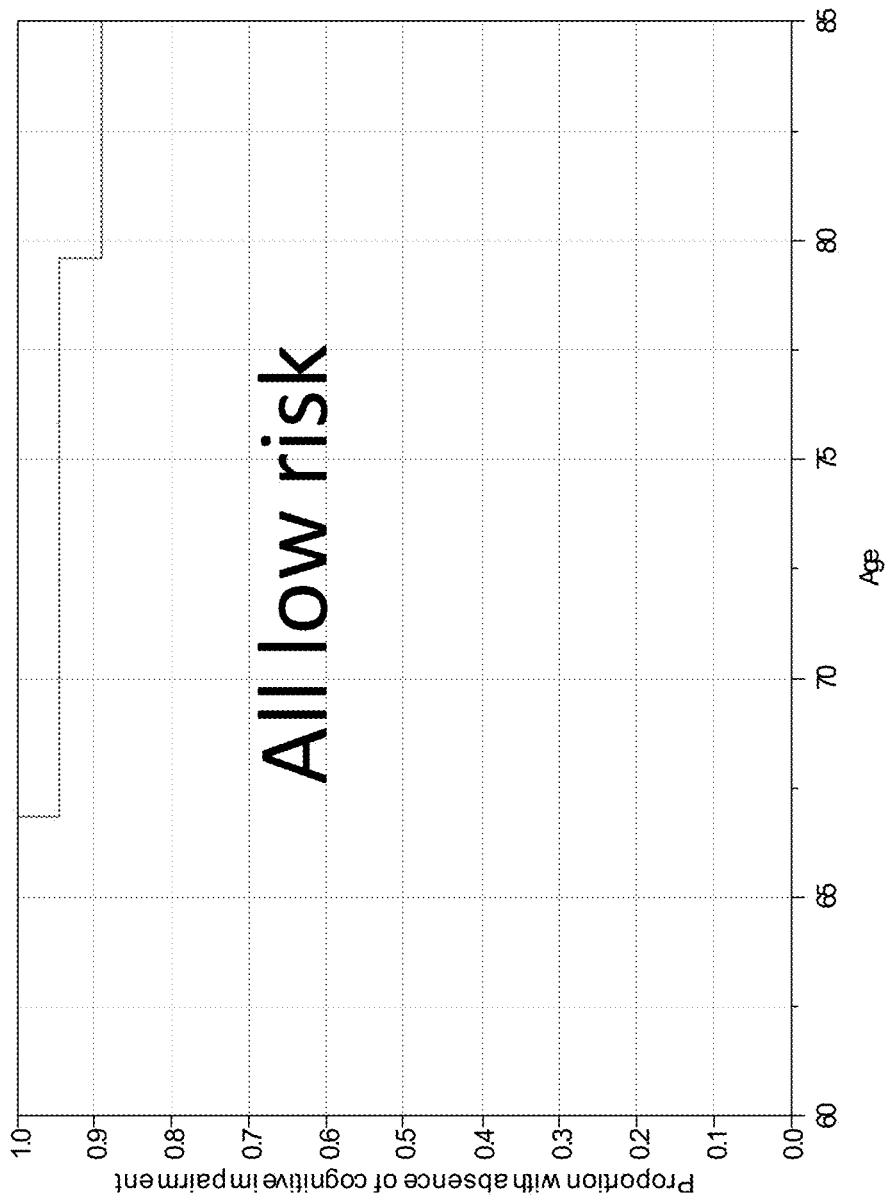
FIG. 9 presents the curve showing age at onset of cognitive impairment of the Alzheimer's type for 523 VL,VL genotype. The Y axis shows the percent survival without CI, while the X axis represents age. Data obtained from the Duke Bryan ADRC cohort N=51 subjects, 6 diagnosed with CI, 45 cognitively normal.

FIG. 3 illustrates determination of an age used to distinguish high- and low-risk classification for the (S,L) 523 genotype. The steep part of the curve can be identified as starting at about age 74, which corresponds to the age associated with a level of 90% of individuals with this genotype not presenting with cognitive impairment. Therefore, individuals aged 74 or older may be assigned to the high-risk group for the study, whereas individuals younger than 74 are assigned to the low-risk group. Exemplary age-of-onset curves for cognitive impairment for the remaining 523 genotypes are provided in FIGS. 4-9, which are reflected in the assignments in Table 2 presented above.

It should be understood that, while the graphs presented herein are interpreted to give a specific age where the slope change occurs, these graphs may be updated as additional data are collected to modify and/or optimize the age designations without departing from the general teachings of this method.

The disclosures of the patents, patent documents, articles, abstracts and other publications cited herein are incorporated by reference herein in their entireties as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

Having described our invention, we claim:

1. A method of treating cognitive impairment of the Alzheimer's type in a human subject in need thereof, comprising administering to said subject about 0.5 milligrams to about 9 milligrams of pioglitazone, wherein the pioglitazone comprises a pharmaceutically acceptable salt of pioglitazone.

2. The method of claim 1, wherein said treating comprises delaying the onset of cognitive impairment of the Alzheimer's type.

3. The method of claim 1, wherein said treating comprises delaying the onset of cognitive impairment of the Alzheimer's type in a human subject at increased risk of developing cognitive impairment of the Alzheimer's type within the next 5-7 years, said risk based upon the subject's age and rs10524523 genotype.

4. The method of claim 1, wherein pioglitazone is administered in unit dosage form.

5. The method of claim 4, wherein the unit dosage form comprises from 0.5 to 9 milligrams of pioglitazone.

6. The method of claim 4, wherein the unit dosage form comprises from 0.5 to 6 milligrams of pioglitazone.

7. The method of claim 4, wherein said unit dosage form comprises from 0.5 to 1.5 milligrams of pioglitazone.

8. The method of claim 1, wherein said administering is once daily.

9. The method of claim 1, wherein
   (i) the subject is about age 62 or more and has an L,L or L,VL genotype;
   (ii) the subject is about age 74 or more and has an S,L genotype;
   (iii) the subject is about age 76 or more and has an S,VL genotype; or
   (iv) the subject is about age 77 or more and has an S,S genotype; and
   wherein the genotype is based on a length of poly-T residues at each allele at rs10524523 in the TOMM40 gene, and wherein
   (a) S is the short poly-T length having less than 19 T residues;
   (b) L is the long poly-T length having 19-29 T residues; and
   (c) VL is the very long poly-T length having 30 or more T residues.

10. The method of claim 9, wherein the subject is age 62 or more and has the L,L or L,VL genotype.

11. The method of claim 9, wherein the subject is age 74 or more and has the S,L genotype.

12. The method of claim 9, wherein the subject is age 76 or more and has the S,VL genotype.

13. The method of claim 9, wherein the subject is age 77 or more and has the S,S genotype.

14. The method of 9, wherein said subject further does not have an ApoE genotype of ε2/ε2 or ε2/ε3.

15. The method of claim 9, wherein 0.5 to 9 milligrams of pioglitazone is administered to said subject.

16. The method of claim 9, wherein 0.5 to 6 milligrams of pioglitazone is administered to said subject.

17. The method of claim 9, wherein 0.5 to 1.5 milligrams of pioglitazone is administered to said subject.

18. The method of claim 9, wherein said treating comprises delaying the onset of cognitive impairment of the Alzheimer's type.

19. The method of claim 18, wherein said subject has normal cognition.

20. The method of claim 19, wherein 0.5 to 9 milligrams of pioglitazone is administered to said subject.

21. The method of claim 19, wherein 0.5 to 6 milligrams of pioglitazone is administered to said subject.

22. The method of claim 19, wherein 0.5 to 1.5 milligrams of pioglitazone is administered to said subject.

23. The method of claim 1, wherein the pioglitazone is in an oral modified release formulation, controlled release formulation, or extended release formulation.

24. The method of claim 1, wherein the subject has one or more symptoms of cognitive impairment of the Alzheimer's type.

25. The method of claim 1, wherein the pioglitazone consists of a pharmaceutically acceptable salt of pioglitazone.

26. The method of claim 1, wherein the pharmaceutically acceptable salt of pioglitazone comprises pioglitazone hydrochloride.

27. The method of claim 25, wherein the pharmaceutically acceptable salt of pioglitazone comprises pioglitazone hydrochloride.

* * * * *